(12) United States Patent
Yaghi et al.

(10) Patent No.: US 10,087,205 B2
(45) Date of Patent: Oct. 2, 2018

(54) METAL ORGANIC FRAMEWORKS COMPRISING A PLURALITY OF SBUS WITH DIFFERENT METAL IONS AND/OR A PLURALITY OF ORGANIC LINKING LIGANDS WITH DIFFERENT FUNCTIONAL GROUPS

(71) Applicant: The Regents of the University of California, Oakland, CA (US)

(72) Inventors: Omar M. Yaghi, Berkeley, CA (US); Mitsuharu Suzuki, Albany, CA (US); Hexiang Deng, Berkeley, CA (US); Lisa Wang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/128,225

(22) PCT Filed: Mar. 27, 2015

(86) PCT No.: PCT/US2015/023173
§ 371 (c)(1),
(2) Date: Sep. 22, 2016

(87) PCT Pub. No.: WO2015/195179
PCT Pub. Date: Dec. 23, 2015

(65) Prior Publication Data
US 2017/0101429 A1 Apr. 13, 2017

Related U.S. Application Data

(60) Provisional application No. 61/972,124, filed on Mar. 28, 2014.

(51) Int. Cl.
*B01J 31/16* (2006.01)
*B01J 20/22* (2006.01)
(Continued)

(52) U.S. Cl.
CPC ............ *C07F 19/005* (2013.01); *B01D 53/02* (2013.01); *B01J 20/226* (2013.01);
(Continued)

(58) Field of Classification Search
None
See application file for complete search history.

(56) References Cited

U.S. PATENT DOCUMENTS 2,684,967 A 7/1954 Berg
4,532,225 A 7/1985 Tsao
(Continued)

FOREIGN PATENT DOCUMENTS

EP 1070538 A2 1/2001
WO 9905151 A1 2/1999
(Continued)

OTHER PUBLICATIONS

Deng et al., "Large-Pore Apertures in a Series of Metal-Organic Frameworks." Science, vol. 336, May 25, 2012, pp. 1018-1023.*
(Continued)

*Primary Examiner* — Daniel Berns
(74) *Attorney, Agent, or Firm* — Gavrilovich, Dodd & Lindsey LLP

(57) ABSTRACT

The disclosure provides for metal organic frameworks (MOFs) which comprise a plurality of SBUs comprising different metals or metal ions and/or a plurality of organic linking moieties comprising different functional groups.

15 Claims, 19 Drawing Sheets

(51) Int. Cl.
  *C07F 19/00* (2006.01)
  *C07F 3/02* (2006.01)
  *C07F 3/04* (2006.01)
  *C07F 3/06* (2006.01)
  *C07F 3/08* (2006.01)
  *C07F 3/10* (2006.01)
  *C07F 5/00* (2006.01)
  *C07F 7/00* (2006.01)
  *C07F 13/00* (2006.01)
  *C07F 15/02* (2006.01)
  *C07F 15/04* (2006.01)
  *C07F 15/06* (2006.01)
  *B01D 53/02* (2006.01)
  *F17C 11/00* (2006.01)

(52) U.S. Cl.
  CPC ............ *B01J 31/1691* (2013.01); *C07F 3/02* (2013.01); *F17C 11/005* (2013.01); *F17C 11/007* (2013.01); *B01D 2253/204* (2013.01); *B01D 2257/108* (2013.01); *B01D 2257/504* (2013.01); *B01D 2257/7025* (2013.01); *B01J 2531/22* (2013.01); *B01J 2531/23* (2013.01); *B01J 2531/24* (2013.01); *B01J 2531/25* (2013.01); *B01J 2531/26* (2013.01); *B01J 2531/27* (2013.01); *B01J 2531/72* (2013.01); *B01J 2531/842* (2013.01); *B01J 2531/845* (2013.01); *B01J 2531/847* (2013.01); *F17C 2221/012* (2013.01); *F17C 2221/013* (2013.01); *F17C 2221/033* (2013.01)

(56) References Cited

U.S. PATENT DOCUMENTS

| | | | |
|---|---|---|---|
| 5,064,804 A | 11/1991 | Soo | |
| 5,160,500 A | 11/1992 | Chu | |
| 5,208,335 A | 5/1993 | Ramprasad | |
| 5,617,467 A | 4/1997 | Bacher et al. | |
| 5,648,508 A | 7/1997 | Yaghi | |
| 5,733,505 A | 3/1998 | Goldstein | |
| 5,779,904 A | 7/1998 | Ruderman | |
| 6,479,447 B2 | 11/2002 | Bijl | |
| 6,501,000 B1 | 12/2002 | Stibrany | |
| 6,617,467 B1 | 9/2003 | Mueller | |
| 6,624,318 B1 | 9/2003 | Mueller | |
| 6,686,428 B2 | 2/2004 | Zhang | |
| 6,893,564 B2 | 5/2005 | Mueller | |
| 6,929,679 B2 | 8/2005 | Mueller | |
| 6,930,193 B2 * | 8/2005 | Yaghi | B01J 20/226 534/15 |
| 7,196,210 B2 * | 3/2007 | Yaghi | B01J 20/226 534/15 |
| 7,202,385 B2 | 4/2007 | Mueller | |
| 7,229,943 B2 | 6/2007 | Gibson | |
| 7,279,517 B2 | 10/2007 | Mueller | |
| 7,309,380 B2 | 12/2007 | Mueller | |
| 7,343,747 B2 | 3/2008 | Mueller | |
| 7,411,081 B2 | 8/2008 | Mueller | |
| 7,524,444 B2 | 4/2009 | Hesse | |
| 7,582,798 B2 | 9/2009 | Yaghi | |
| 7,637,983 B1 | 12/2009 | Liu | |
| 7,652,132 B2 | 1/2010 | Yaghi | |
| 7,662,746 B2 | 2/2010 | Yaghi | |
| 7,799,120 B2 | 9/2010 | Yaghi | |
| 7,815,716 B2 | 10/2010 | Mueller | |
| 8,343,260 B2 | 1/2013 | Omary | |
| 8,480,955 B2 | 7/2013 | Yaghi | |
| 8,501,150 B2 | 8/2013 | Schubert | |
| 8,518,264 B2 | 8/2013 | Kiener | |
| 8,524,932 B2 | 9/2013 | Leung | |
| 8,709,134 B2 | 4/2014 | Yaghi | |
| 8,735,161 B2 | 5/2014 | Yaghi | |
| 8,742,152 B2 | 6/2014 | Yaghi | |
| 9,078,922 B2 | 7/2015 | Yaghi | |
| 2003/0004364 A1 | 1/2003 | Yaghi | |
| 2003/0078311 A1 | 4/2003 | Muller | |
| 2003/0148165 A1 | 8/2003 | Muller | |
| 2003/0222023 A1 | 12/2003 | Mueller | |
| 2004/0081611 A1 | 4/2004 | Muller | |
| 2004/0225134 A1 | 11/2004 | Yaghi | |
| 2004/0249189 A1 | 12/2004 | Mueller | |
| 2004/0265670 A1 | 12/2004 | Muller | |
| 2005/0004404 A1 | 1/2005 | Muller | |
| 2005/0014371 A1 | 1/2005 | Tsapatsis | |
| 2005/0124819 A1 | 6/2005 | Yaghi | |
| 2005/0154222 A1 | 7/2005 | Muller | |
| 2005/0192175 A1 | 9/2005 | Yaghi | |
| 2006/0057057 A1 | 3/2006 | Muller | |
| 2006/0135824 A1 | 6/2006 | Mueller | |
| 2006/0154807 A1 | 7/2006 | Yaghi | |
| 2006/0185388 A1 | 8/2006 | Muller | |
| 2006/0252641 A1 | 11/2006 | Yaghi | |
| 2006/0252972 A1 | 11/2006 | Pilliod | |
| 2006/0287190 A1 | 12/2006 | Eddaoudi | |
| 2007/0068389 A1 | 3/2007 | Yaghi | |
| 2007/0202038 A1 | 8/2007 | Yaghi | |
| 2007/0217982 A1 | 9/2007 | Wright | |
| 2007/0248575 A1 | 10/2007 | Connor | |
| 2008/0017036 A1 | 1/2008 | Schultink | |
| 2008/0184883 A1 | 8/2008 | Zhou | |
| 2008/0190289 A1 | 8/2008 | Muller | |
| 2009/0155588 A1 | 6/2009 | Hesse | |
| 2009/0183996 A1 | 7/2009 | Richter | |
| 2009/0216059 A1 | 8/2009 | Reyes | |
| 2009/0247654 A1 | 10/2009 | Rajendran | |
| 2010/0069234 A1 | 3/2010 | Willis | |
| 2010/0132549 A1 | 6/2010 | Yaghi | |
| 2010/0143693 A1 | 6/2010 | Yaghi | |
| 2010/0186588 A1 | 7/2010 | Yaghi | |
| 2010/0286022 A1 | 11/2010 | Yaghi | |
| 2011/0015388 A1 | 1/2011 | Youngblood | |
| 2011/0137025 A1 | 6/2011 | Yaghi | |
| 2011/0282067 A1 | 11/2011 | Li | |
| 2011/0282071 A1 | 11/2011 | Shi | |
| 2012/0028846 A1 | 2/2012 | Yaghi | |
| 2012/0031268 A1 | 2/2012 | Yaghi | |
| 2012/0130113 A1 | 5/2012 | Yaghi | |
| 2012/0133939 A1 | 5/2012 | Yaghi | |
| 2013/0047849 A1 | 2/2013 | Zhang | |
| 2013/0096210 A1 | 4/2013 | Yaghi et al. | |
| 2014/0037944 A1 | 2/2014 | Dichtel | |
| 2014/0148596 A1 | 5/2014 | Dichtel | |

FOREIGN PATENT DOCUMENTS

| | | |
|---|---|---|
| WO | 03035717 A1 | 5/2003 |
| WO | 2004101575 A2 | 11/2004 |
| WO | 2006047423 A2 | 5/2006 |
| WO | 2006072573 A2 | 7/2006 |
| WO | 2006110740 A2 | 10/2006 |
| WO | 2006116340 A1 | 11/2006 |
| WO | 2006122920 A1 | 11/2006 |
| WO | 2006125761 A2 | 11/2006 |
| WO | 2007007113 A2 | 1/2007 |
| WO | 2007054581 A2 | 5/2007 |
| WO | 2007098263 A2 | 8/2007 |
| WO | 2007101241 A2 | 9/2007 |
| WO | 2007111739 A2 | 10/2007 |
| WO | 2007118843 A1 | 10/2007 |
| WO | 2008091976 A1 | 7/2008 |
| WO | 2008138989 A1 | 11/2008 |
| WO | 2008140788 A1 | 11/2008 |
| WO | 200920745 A2 | 2/2009 |
| WO | 2009042802 A1 | 4/2009 |
| WO | 2009056184 A1 | 5/2009 |
| WO | 2009073739 A1 | 6/2009 |
| WO | 2009149381 A2 | 12/2009 |
| WO | 2010056092 A2 | 5/2010 |
| WO | 2010078337 A1 | 7/2010 |
| WO | 2010080618 A2 | 7/2010 |
| WO | 2010083418 A1 | 7/2010 |

(56) References Cited

FOREIGN PATENT DOCUMENTS

| WO | 2010088629 A1 | 8/2010 |
|---|---|---|
| WO | 2010090683 A1 | 8/2010 |
| WO | 2010148276 A2 | 12/2010 |
| WO | 2010148296 A2 | 12/2010 |
| WO | 2010148374 A2 | 12/2010 |
| WO | 2011014503 A1 | 2/2011 |
| WO | 2011038208 A2 | 3/2011 |
| WO | 2011127301 A | 10/2011 |
| WO | 2011146155 A2 | 11/2011 |
| WO | 2012012495 A2 | 1/2012 |
| WO | 2012082213 A2 | 6/2012 |
| WO | 2012100224 A2 | 7/2012 |
| WO | 2012106451 A2 | 8/2012 |

OTHER PUBLICATIONS

Lun et al., "A General Thermolabile Protecting Group Strategy for Organocatalytic Metal-Organic Frameworks." J. Am. Chem. Soc., 2011, vol. 133, pp. 5806-5809 (published online Mar. 28, 2011).*
Nickitas-Etienne, Athina, International Preliminary Report on Patentability and Written Opinion, PCT/US2015/023173, The International Bureau of WIPO, dated Oct. 13, 2016.
Burrows, Andrew D., "Mixed-component metal-organic frameworks (MC-MOFs): enhancing functionality through solid solution formation and surface modifications", Crystengcomm, vol. 13, No. 11, Jan. 1, 2011, pp. 3623-3642.
Deng et al., "Multiple Functional Groups of Varying Ratios in Metal-Organic Frameworks", Science, vol. 327, No. 5967, Feb. 12, 2010, pp. 846-850.
Fracaroli, A.M. et al., "Metal-Organic Frameworks with Precisely Designed Interior for Carbon Dioxide Capture in be Presence of Water", J. Am. Chem. Soc., Jun. 25, 2014, vol. 136, No. 25, pp. 8863-8866.
Hurenkamp, Jaap, International Search Report and Written Opinion, PCT/US2015/023173, European Patent Office, dated Apr. 11, 2016.
Kong et al., "Mapping of Functional Groups in Metal-Organic Frameworks", Science, vol. 341, No. 6148, Jul. 25, 2013, pp. 882-885.
Jones, Christopher. Nonfinal Office Action for U.S. Appl. No. 12/598,855, dated Oct. 12, 2012.
Jones, Christopher. Nonfinal Office Action for U.S. Appl. No. 12/598,855, dated Jun. 14, 2012.
Kandiah et al., 'Post-synthetic modification of the metal-organic framework compound UiO-66,' J. of Mater. Chem., vol. 20, No. 44, pp. 9848-9851, 2010.
Kaye et al., 'Impact of Preparation and Handling on the Hydrogen Storage Properties of Zn4O(1,4-benzenedicarboxylate)3 (MOF-5),' J. Am. Chem. Soc. 129:14176-14177 (2007).
Kim et al., 'Assembly of Metal-Organic Frameworks from Large organic and Inorganic Secondary Building Units: New Examples and Simplifying Principles for Complex Structures,' J. Am. Chem. Soc, 2001, 123, 8239-8247.
Kim et al., "Isoreticular MOFs based on a rhombic dodecahedral mop as a tertiary building unit", CrystEngComm, Mar. 3, 2014, vol. 16, pp. 6391-6397.
Kim, Su Mi, International Search Report and Written Opinion for PCT/US2009/068731, dated Aug. 19, 2010.
Kim, Su Mi, International Search Report and Written Opinion, Application No. PCT/US09/046463, dated Feb. 24, 2010.
Kim, Su Mi, International Search Report and Written Opinion, PCT/US2010/039154, Korean Intellectual Property Office, dated Feb. 23, 2011.
Kim, Su Mi. International Search Report for PCT/US2010/039154, dated Feb. 23, 2011.
Kirai et al., 'Homocoupling of arylboronic acids catalyzed by 1,10-phenanthroline—ligated copper complexes in air,' European Journal of Organic Chemistry 12:1864-1867 (2009).
Klaes, Daphane, International Search Report and Written Opinion for PCT/US2010/021201, European Patent Office, dated Apr. 27, 2010.
Klaes, Daphne. International Search Report and Written Opinion for PCT/US2010/021201, dated Apr. 27, 2010.
Klein et al., 'Combinatorial Material Libraries on the Microgram Scale with an Example of Hydrothermal Synthesis,' Angew. Chemie 37(24):3369-3372 (1998).
Klemperer et al., "New Directions in Polyvanadate Chemistry: From Cages and Clusters to Baskets, Belts, Bowls, and Barrels", Angew. Chem. Int. Ed. Engl. 31 (1992) No. 1, pp. 49-51.
Koh et al., 'A Crystalline Mesoporous Coordination Copolymer with High Microporosity,' Angew Chem Inn, 2008, pp. 677-680, vol. 47.
Koh et al., "A Crystalline Mesoporous Coordination Copolymer with High Microporosity", Angew. Chem. Int. Ed. 2008, 120, pp. 689-692.
Koh, Kyoungmoo, et al., "A Crystalline Mesoporous Coordination Copolymer with High Microporosity", Angewandte Chemie International Edition, (Jan. 11, 2008), vol. 47, No. Issue, pp. 689-692, XP008150670.
Kokubo, Atsuki, Office Action, Japanese Patent Application No. 2012-553065, dated Feb. 3, 2015.
Koza et al., 'An efficient High Yielding Approach for the Homocoupling of Aryl Boronic Acids,' Synthesis 15:2183-2186 (2002).
Kyoungmoo et al., 'A Crystalline Mesoporous Coordination Copolymer with High Microporosity,' Angew. Chem. Int. Ed. 17(4):677-680 (2008).
Kyoungmoo et al., "A Crystalline Mesoporous Coordination Copolymer with High Microporosity," Angew. Chem. Int. Ed. 47(4):689-92 (2008).
Lange Tim, International Search Report, Application No. PCT/US2015/021090, dated Sep. 21, 2015.
Lawrence, Frank M. Nonfinal Office Action for U.S. Appl. No. 12/699,616, dated Apr. 10, 2012.
Lawrence, Frank M., Non-Final Office Action for U.S. Appl. No. 12/699,616, United States Patent and Trademark Office, dated Aug. 3, 2012.
Lee et al., 'Synthesis and Gas Sorption Properties of a Metal-Azolium Framework (MAF) Material,' Inorganic Chemistry, Nov. 2, 2009, pp. 9971-9973, vol. 48, No. 21.
Lee, Ji Min, International Search Report and Written Opinion, Application No. PCT/US2010/039284, dated Feb. 23, 2011.
Leus et al., "The remarkable catalytic activity of the saturated metal organic framework V-MIL-47 in the cyclohexene oxidation", Chem. Comm., Jun. 18, 2010, 46, 5085-5087.
Li et al., '[Cd16In64S134]44-: 31-A Tetrahedron with a Large Cavity,' Angew. Chem. Int. Ed., 42:1819-1821 (2003).
Li et al., '20 A [Cd4In16S35]14-Supertetrahedral T4 Clusters as Building Units in Decorated Cristobalite Frameworks,' J. Am. Chem. Soc, 2001, 123, 4867-4868.
Li et al., 'A Catenated Strut in a Catenated Metal-Organic Framework,' Angew. Chem. Int. Ed. 49:6751-6755 (2010).
Li et al., 'A metal-organic framework replete with ordered donor-acceptor catenanes,' Chem. Commun. 46:380-382 (2010).
Li et al., 'An Open-Framework Germanate with Polycubane-Like Topology,' Angew. Chem. Int. Ed., 38:653-655 (1999).
Li et al., 'Coordinatively Unsaturated Metal Centers in the Extended Porous Framework of Zn3(BDC)36CH30H (BDG =1,4-Benzenedicarboxylate),' J. Am. Chem. Soc, 1998, 120, 2186-2187.
Li et al., 'Design and Synthesis of an Exceptionally Stable and Highly Porous Metal-Organic Framework,' Nature, 1999, 402, 276-279: Featured in (1) Chemical and Engineering News, Nov. 22, 1999, and (2) Science News, Nov. 20, 1999.
Li et al., 'Docking in Metal-Organic Frameworks', Science, 325, 855 (2009).
Li et al., 'Establishing Microporosity in Open Metal-Organic Frameworks: Gas Sorption Isotherms for Zn(BDC) (BDC=1,4-Benzenedicarboxylate),' J. Am. Chem. Soc, 1998, 120, 8571-8572.
Li et al., 'Ge2Zr06F2 (H2DAB)H20: A 4-Connected Microporous Material with 'Bow Tie' Building Units and an Exceptional Proportion of 3-Rings,' J. Am. Chem. Soc, 2000, 122, 12409-12410.

(56) References Cited

OTHER PUBLICATIONS

Li et al., 'Non-interpenetrating Indium Sulfide with a Supertetrahedral Cristobalite Framework,' J. Am. Chem. Soc, 1999, 121,6096-6097.
Li et al., 'Supertetrahedral Sulfide Crystals with Giant Cavities and Channels,' Science, 1999, 283, 1145-1147.
Li et al., 'Synthesis and Structural Characterization of a New 3D Lead Coordination Polymer with a Tetrazole-1-acetate Ligand,' Chinese J. Struct. Chem. 30(7): 1049-1053 (2011).
Li et al., 'Transformation of Germanium Dioxide to 4-Connected Porous Germanate Net,' J. Am. Chem. Soc, 1998, 120, 10569-10570.
Li Hailian, et al., 'Porous Germanates: Synthesis, Structure and Inclusion Properties of Ge7014.5F2[(CH3)2NH2]3(H20) 0.86,' J. Am. Chem. Soc, 1998, 120, 8567-8568.
Li, Y. et al., 'Hydrogen Storage in Metal-Organic and Covalent-Organic Frameworks by Spillover,' AlChe Journal 54 (1):269-279 (2008).
Linder, Nora, International Preliminary Report on Patentability and Written Opinion, Application No. PCT/US2010/022777, dated Aug. 2, 2011.
Lindner, Nora, International Preliminary Report on Patentability and Written Opinion, The International Bureau of WIPO, PCT/US2011/044625, dated Jan. 31, 2013.
Lindner, Nora, International Preliminary Report on Patentability, PCT/US2011/053423, The International Bureau of WIPO, dated Apr. 2, 2013.
Ling et al., 'A zinc(II) metal-organic framework based on triazole and dicarboxylate ligands for selective adsorption of hexane isomers,' Chem. Comm. 47:7197-7199 (2011).
Liu, Lei, First Office Action, Chinese Patent Application No. 201180009370.6,The State Intellectual Property Office of the People's Republic of China, dated Mar. 3, 2014.
Liu., Y., "Dynamic Chirality in Donor-Acceptor Pretzelanes", Journal of Organic Chemistry, 2005, 70, 9334-9344.
Patteux, Claudine. International Search Report for PCT/US2010/043373, dated Oct. 10, 2010.
Pawsey et al., 'Hyperpolarized 129Xe Nuclear Magnetic Resonance Studies of Isoreticular Metal-Organic Frameworks,' Phys. Chem. 111:6060-6067 (2007).
Peng et al., 'Methane Storage in Metal-Organic Frameworks: Current Records, Surprise Findings, and Challenges', Journal of the American Chemical Society, vol. 135, No. 2, Aug. 14, 2013, pp. 11887-11894.
Peterson et al., 'Ammonia Vapor Removal by Cu3(BTC)2 and Its Characterization by MAS NMR,' J. Phys. Chem. C. 113(32):13906-13917 (2009).
Phan et al., 'Metal-Organic Frameworks of Vanadium as Catalysts for Conversion of Methane to Acetic Acid,' Inorg. Chem. 50:7388-7390 (2011).
Phan et al., 'Synthesis, Structure, and Carbon Dioxide Capture Properties of Zeolitic Imidazolate Frameworks,' Am. Chem. Res 43:58-67 (2009).
Plevert et al., 'A Flexible Germanate Structure Containing 24-Ring Channels With Very Low Framework Density,' J. Am. Chem. Soc, 2001, 123, 12706-12707.
Plevert et al., 'Layered Structures Constructed from New Linkages of Ge7(0,OH,F)19 Clusters,' Chem. Mater. 15:714-718(2003).
Plevert et al., 'Synthesis and Characterization of Zirconogermanates,' Inorg. Chem., 42:5954-5959 (2003).
Prajapati et al., "Metal-organic frameworks (MOFs) constructed from ZnII/CdII-2,2'-bipyridines and polycarboxylic acids: Synthesis, characterization and microstructural studies", Polyhedron 28 (2009) 600-608.
Qiu, Xiaowei, Chinese Application No. 201180056905.5, Second Office Action, dated Feb. 3, 2015.
Qiu, Xiaowei, Chinese Patent Application No. 201180056905.5, First Office Action, dated Jul. 18, 2014.
Queen et al., 'Site-Specific C02 Adsorption and Zero Thermal Expansion in an Anisotropic Pore Network,' J. Phys. Chem. C, 115:24915-24919 (Nov. 8, 2011).

Reineke et al., 'A Microporosity of Lanthanide-Organic Frameworks,' Angew. Chem. Int. Ed. 38:2590-2594 (1999).
Reineke et al., 'From Condensed lanthanide Coordination Solids to Microporous Frameworks having Accessible Metal Sites,' J. Am. Chem. Soc, 1999, 121, 1651-1657.
Reineke et al., 'Large Free Volume in Interpenetrating Networks: The Role of Secondary Building Units Exemplified by Tb2(ADB)3[(CH3)2SO]4-16[(CH3)2SO],' J. Am. Chem. Soc, 2000, 122, 4843-4844: Featured in Science Magazine, Editors Choice, Nov. 2000.
Ren Shi-Bin et al, "The variety of conformational isomerism of a flexible organic linker induced by the position and amounts of aromatic carboxylic groups", Polyhedron, (Jun. 4, 2014), vol. 83, doi:10.1016/JPOLY.2014.05.069, ISSN 3277-5387, pp. 130-136, XP029030831.
Richter, Herbert, Supplementary European Search Report, European Patent Application No. 11848340.3, European Patent Office, dated Feb. 6, 2014.
Rinkel, Bert. Extended European Search Report for European Patent Application EP08713961, dated Jan. 2, 2012.
Rosi et al., 'Advances in the Chemistry of Metal-Organic Frameworks,' CrystEngComm, 2002, 4, 401-404.
Rosi et al., 'Infinite Secondary Building Units and Forbidden Catenation in Metal-Organic Frameworks,' Angew. Chem. Int. Ed. 41:294-297 (2002).
Rosi et al., 'Rod-Packings and Metal-Organic Frameworks Constructed from Rod-Shaped Secondary Building Units,' J. Am. Chem. Soc. 127:1504-1518 (2005).
Rosi etal., 'Hydrogen Storage in Microporous Metal-Organic Frameworks,' Science 300:1127-1129 (2003); Featured in (1) Chemical & Engineering News magazine, May 19, 2004, and (2) Technology Research News Magazine, May 21, 2003.
Rouseau-Jager, Nadia, International Search Report and Written Opinion, PCT/US2011/024671, European Patent Office, dated Dec. 13, 2011.
Rowsell et al., 'Characterization of H2 Binding sites in prototypical metal-organic frameworks by inelastic neutron scattering,' J. Am. Chem. Soc. 127:14904-14910 (2005).
Rowsell et al., 'Effects of Functionalization, Catenation, and Variation of the Metal Oxide and Organic Linking Units on the Low-Pressure Hydrogen Adsorption Properties of Metal-Organic Frameworks,' J. Am. Chem. Soc. 128: 1304-1315(2006).
Rowsell et al., 'Gas Adsorption Sites in a Large-Pore Metal-Organic Framework,' Science 309:1350-1354 (2005).
Rowsell et al., 'Hydrogen Sorption in Functionalized Metal-Organic Frameworks,' J. Am. Chem. Soc.126: 5666-5667 (2004).
Rowsell et al., 'Metal-Organic Frameworks: A New Class of Porous Materials,' Microporous Mesoporous Mater. 73:3-14 (2004).
Rowsell et al., 'Strategies for Hydrogen Storage in Metal-Organic Frameworks,' Angew. Chem. Int. Ed. 44: 4670-4679 (2005).
Seo et al., 'A homochiral metal-organic porous material for enantioselective separation and catalysis,' Nature 404:982-986 (2000).
Shi-Jie et al., "Synthesis and Structural Characterization of a New 3D Lead Coordination Polymer with a Tetrazole-1-acetate Ligand", Chinese J. Struct. Chem., vol. 30, No. 7, 2011, pp. 1049-1053.
Siberio-Perez, 'Raman Spectroscopic Investigation of CH4 and N2 Adsorption in Metal-Organic Frameworks,' Chem. Mater. 19:3681-3685 (2007).
Sigma-Aldrich, Basolite C300 (MOF-199), catalog No. 688614; http://www.sigmaaldrich.com/catalog/ProductDetail.do?D7=0&N5=SEARCH.sub.—-Concat.sub.-PNO%7CBRAND.sub.-KEY&N4=688614%7CALDRICH&N25=0&Qs=ON&F=SPEC-, obtained online in 2014.
Sigma-Aldrich, Basolite C300 (MOF-199), catalog No. 688614; Copyright 2014.
Sigma-Aldrich, Citric acid, ACS reagent. Accessed online at https://www.sigmaaldrich.com/catalog/product/sial/251275?lang=en&region=US, 1 page.
Sines, Brian J. Nonfinal Office Action for U.S. Appl. No. 13/142,564, dated Jul. 9, 2012.
Smaldone et al., 'Metal-Organic Frameworks from Edible Nature Products,' Angew. Chem. Int. Ed. 49:8630-8634 (2010).

(56) References Cited

OTHER PUBLICATIONS

Song et al., 'A Multiunit Catalyst with Synergistic Stability and Reactivity: A PolyoxometalateMetal Organic Framework for Aerobic Decontamination,' J. Am. Chem. Soc. 133(42):16839-16846 (Sep. 13, 2011).
Song et al., 'Hydrothermal Synthesis and Structural Characterization of Three-dimensional Metal-organic Framework [Zn3(C2H2N3)2(C7H5O2)4],' Chem. Res. Chinese Universities 25(1):1-4 (2009).
Spencer et al., 'Determination of the Hydrogen Absorption Sites in Zn4O(1,4-benzenedicarboxylate) by Single crystal Neutron Diffraction,' Chem. Commun. 3:278-280 (2006); Epub Dec. 6, 2005.
Spitler et al., 'Lewis acid-catalysed formation of two-dimensional phthalocyanine covalent organic frameworks', Nature Chemistry, vol. 2, Aug. 2010, pp. 672-677.
Stallmach et al., 'NMR Studies on the Diffusion of Hydrocarbons on the Metal-Organic Framework Material MOF-5,' Angew. Chem. Int. Ed. 45:2123-2126 (2006).
Sudik et al., 'A Metal-Organic Framework with a Hierarchical System of Pores and Tetrahedral Bbuilding Blocks,' Angew. Chem. Int. Ed. 45:2528-2533 (2006).
Sudik et al., 'Design, Synthesis, Structure, and Gas (N2, Ar, CO2, CH4 and H2) Sorption Properties of Porous Metal-Organic Tetrahedral and Heterocuboidal Polyhedra,' J. Am. Chem. Soc. 127:7110-7118 (2005).
Sudik et al., 'Metal-Organic Frameworks Based on Trigonal Prismatic Building Blocks and the New 'acs' Topology,' Inorg. Chem. 44:2998-3000 (2005).
Szeto et al., "A Thermally Stable Pt/Y-Based Metal-Organic Framework: Exploring the Accessibility of the Metal Centers with Spectroscopic Methods Using H2O, CH3OH, and CH3CN as Probes", J. Phys. Chem. B, 2006, 110, 21509-21520.
Szeto et al., "Characterization of a New Porous Pt-Containing Metal-Organic Framework Containing Potentially catalytically Active Sites: Local Electronic Structure at the Metal Centers", Chem. Mater., 2007, 19, 211-220.
Tanabe et al., 'Systematic Functionalization of a Metal-Organic Framework via a Postsynthetic Modification Approach,' J. Am. Chem. Soc. 130(26):8508-8517 (2008).
Tilford et al., 'Facile Synthesis of a Highly Crystalline, Covalently Porous Boronate Network,' 18(22):5296-5301 (Oct. 11, 2006).
Chun et al., 'Concomitant Formation of N-Heterocyclic Carbene-Copper Comlexies within a Supramolecular Network in the Self-Assembly of Immidzolium Dicarboxylate with Metal Ions,' Inorganic Chemistry, Jul. 20, 2009, pp. 6353-6355, vol. 48, No. 14.
Chun et al., 'Cu2O: A versatile Reagent for Base-Free Direct Synthesis of NHC-Copper Complexes and Decoration of 3D-MOF with Coordinatively Unsaturated NHC-Copper Species,' Organometallics, Mar. 16, 2010, pp. 1518-1521, vol. 29, No. 7.
Cordero Garcia, Marcela M. Nonfinal Office Action for U.S. Appl. No. 12/680,141, dated Nov. 2, 2012.
Corma et al., 'A large-cavity zeolite with wide pore windows and potential as an oil refining catalyst,' Nature, vol. 418, pp. 514-517 (Aug. 2002).
Corma et al., "From MOFs to zeolites: zirconium sites for epoxide rearrangement," New J. of Chem. 37:3496-3502, Aug. 2, 2013.
Coskun et al., 'Metal-Organic Frameworks Incorporating Copper-Complexed Rotaxanes,' Angew. Chem. Int. Ed., 51:2160-2163 (2012).
Costa ("Chemical Modification of a Bridging Ligand Inside a Metal-Organic Framework while Maintaining the 3D Structure" Eur. J. Inorg. Chem (2008) 10, 1551-1554).
Costa et al., 'Chemical Modification of a Bridging Ligand Inside a Metal-Organic Framework while Maintaining the 3D Structure,' Eur. J. Inorg. Chem. 10:1539-1545 (2008).
Cote et al., 'Porous, Crystalline, Covalent Organic Frameworks,' Science 310:1166-1170 (2005).
Cote et al., 'Reticular Synthesis of Microporous and Mesoporous 2D Covalent Organic Frameworks,' J. Am. Chem. Soc. 129:12914-12915 (2007).
Crees et al., 'Synthesis of a Zinc(II) Imidazolium Dicarboxylate Logand Metal-Organic Framework (MOF): A Potential Precursor to MOF-Tethered N-Heterocyclic Carbene Compounds,' Inorganic Chemistry, Jan. 19, 2010, vol. 49, No. 1, pp. 1712-1719.
Cui et al., 'In Situ Hydrothermal Growth of Metal-Organic Framework 199 Films on Stainless Steel Fibers for Solid-Phase Microextraction of Gaseous Benzene Homologues,' Anal. Chem. 81(23):9771-9777 (2009).
Czaja et al., 'Industrial applications of metal-organic frameworks,' Chemical Society Reviews 38(5):1284-1293 (2009).
Day et al., "A New Structure Type in Polyoxoanion Chemistry: Synthesis and Structure of the V5O143-Anion", J. Am. Chem. Soc. 1989, 111, 4518-4519.
Day et al., "Synthesis and Characterization of a Soluble Oxide Inclusion Complex, [CH3CNC(V12O324-)]", J. Am. Chem. Soc. 1989, 111, 5959-5961.
Delgado-Friedrichs et al., 'Three-Periodic Nets and Tilings: Semiregular Nets,' Acta Cryst. A59:515-525 (2003).
Delgado-Friedrichs et al. 'Three-Periodic Nets and Tilings: Edge-Transitive Binodal Structures,' Acta Cryst. 62:350-355 (2006).
Delgado-Friedrichs et al. 'What Do We Know About Three-Periodic Nets?,' J. Solid State Chem. 178:2533-2554 (2005).
Delgado-Friedrichs et al., 'Taxonomy of Periodic Nets and the Design of Materials,' Phys. Chem. 9:1035-1043 (2007).
Delgado-Friedrichs et al., 'The CdSO4, Rutile, Cooperate and Quartz Dual Nets: Interpenetration and Catenation,' Solid State Sciences 5:73-78 (2003).
Delgado-Friedrichs et al., 'Three-Periodic Nets and Tilings: Regular and Quasiregular Nets,' Acta Cryst. A59:22-27 (2003).
Demessence, A et al., 'Strong CO2 Bnding in a Water-Stable, Triazolate-Bridged Metal-Organic Framework Functionalized with Ethylenediamine,' J. Am. Chem. Soc. 131:8784-8786 (2009).
Demir et al., 'Role of Copper Species in the Oxidative Dimerization of Arylboronic Acids: Synthesis of Symmetrical Biaryls,' Journal of Organic Chemistry 68(26):10130-10134 (2003).
Deng et al., 'Large-Pore Apertures in a Series of Metal-Organic Frameworks,' Science 336:1018-1023 (May 25, 2012).
Deng et al., 'Robust dynamics' Nature Chem. 2:439-443 (2010).
Deng, H. et al., "Large-Pore Apertures in a Series of Metal-Organic Frameworks," Science, vol. 336, No. 6084, May 12, 2012, pp. 1018-1023.
Deska, Malgorzata, "Donor-acceptor rotaxanes with tetracationic cyclophane ring", ARKIVOC, 2013, i, 185-242.
Deska, Malgorzata, "Rotaxanes and pseudorotaxanes with threads containing viologen units", ARKIVOC, 2013, i, 56-100.
Dhakshinamoorthy et al., "Metal-organic frameworks as heterogeneous catalysts for oxidation reactions", Catal. Sci. Technol., Apr. 28, 2011, 1, 856-867.
Dietzel, Pascal D. C., et. al., "Application of metal-organic frameworks with coordinatively unsaturated metal sites in storage and separation of methane and carbon dioxide", Journal of Materials Chemistry, (Aug. 21, 2009), vol. 19, No. 39, doi:10.1039/b911242a, ISSN 0959-9428, pp. 7362-7370, XP055197279.
Doonan et al., 'Exceptional ammonia uptake by a covalent organic framework,' Nature Chem. 2:235-238 (2010).
Doonan et al., 'Hydrogen Storage in Metal-Organic Frameworks', Annual Merit Review Proceedings of DOE Hydrogen Program, May 22, 2009, pp. 1-27.
Doonan et al., 'Isoreticular Metalation of Metal-Organic Frameworks,' J. Am. Chem. Soc. 131:9492-9493 (2009).
Du et al., "Direction of unusual mixed-ligand metal-organic frameworks: a new type of 3-D polythreading involving 1-D and 2-D structural motifs and a 2-fold interpenetrating porous network", Chem. Commun., 2005, 5521-5523.
Dugan et al., 'Covalent modification of a metal-organic framework with isocyanates: probing substrate scope and reactivity,' 29:3366-3368 (2008).
Duren et al., 'Design of New Materials for Methane Storage,' Langmuir 20:2683-2689 (2004).
Eberhard, Michael, Extended European Search Report, EP11810321, dated Jan. 14, 2014.

(56) References Cited

OTHER PUBLICATIONS

Eberhard, Michael, International Search Report and Written Opinion, PCT/US2012/059877, European Patent Office, dated Oct. 15, 2013.
Eddaoudi et al., 'Cu2[o-Br-C6H3(C02)2]2(H20)2-(DMF)8(H20)2: A Framework Deliberately Designed to have the NbO Structure Type,' J. Am. Chem. Soc.124:376-377 (2002).
Eddaoudi et al., 'Design and Synthesis of Metal-Organic Frameworks with Permanent Porosity,' In Topics in Catalysis, G. A. Somorjai and J. M. Thomas, Eds., 9:105 (1999).
Eddaoudi et al., 'Geometric Requirements and Examples of Important Structures in the Assembly of Square Building Blocks,' Proc. Natl. Acad. Sci. 99:4900-4904 (2002).
Eddaoudi et al., 'Highly Porous and Stable Metal-Organic Framework: Structure Design and Sorption Properties,' J. Am. Chem. Soc. 121:1391-1397 (2000).
Eddaoudi et al., 'Modular Chemistry: Secondary Building Units as a Basis for the Design of Highly Porous and Robust Metal-Organic Carboxylate Frameworks' Acc. Chem. Res. 34:319-330 (2001).
Eddaoudi et al., 'Porous Metal-Organic Polyhedra: 25 a Cuboctahedron Constructed from Twelve Cu2(C02)4 Paddle-Wheel Building Blocks,' J. Am. Chem. Soc. 123:4368-4369 (2001).
Eddaoudi et al., 'Systematic Design of Pore Size and Functionality in Isoreticular Metal-Organic Frameworks and Application in Methane Storage,' Science 295:469-472 (2002): Featured in (1) Chemical and Engineering News, Jan. 21, 2002, and (2) Chemical Insight magazine, Nov. 15, 2002.
Eddaoudi, M et al., "Systematic Design of Pore Size and Functionality in Isoreticular MOFs and Their application in Methane Storage" Science, (2002), vol. 295, pp. 469-472.
Eiichiro Mizushima, Notice of Reasons for Rejection, Japanese Patent Application No. 2012-516363, dated Aug. 26, 2014.
El-Kaden et al., 'Designed Synthesis of 3D Covalent Organic Frameworks,' Science 316:268-272 (2007).
El-Kaden et al., "Supporting Online Material for Designed Synthesis of 3D Covalent Organic Frameworks", Science 316, 268 (2007).
El-Kaden, Hani M., et al., "Designed Synthesis of 3D Covalent Organic Frameworks", Science 316, 268 (Published Apr. 13, 2007), S1-S75.
"IUPAC Gold Book-cryptand", http://goldbook.iupac.org/C01426.html, accessed Jan. 30, 2014.
"IUPAC Gold Book-macrocycle". http://goldbook.iupac.org/M03662.html, accessed Jan. 30, 2014.
Adkins, Chinessa T. Final Office Action for U.S. Appl. No. 12/524,205, dated Sep. 27, 2012.
Adkins, Chinessa T. Nonfinal Office Action for U.S. Appl. No. 12/524,205, dated Apr. 17, 2012.
Akporiaye et al., 'Combinatorial Approach to the Hydrothermal Synthesis of Zeolites,' Angew. Chemie 37(5):609-611 (1998).
Ashton, Peter R. et al., 'Hydrogen-Bonded Complexes of Aromatic Crown Ethers with (9-Anthracenyl) methylammonium Derivatives' J. Am. Chem. Soc., 1997, 119 (44), pp. 10641-10651.
Baharlou, Simin, International Preliminary Report on Patentability for PCT/US2009/043373, The International Bureau of WIPO, dated Feb. 9, 2012.
Baharlou, Simin, International Preliminary Report on Patentability for PCT/US2009/046463, The International Bureau of WIPO, dated Dec. 16, 2010.
Baharlou, Simin, International Preliminary Report on Patentability for PCT/US2011/024671, The International Bureau of WIPO, dated Aug. 23, 2012.
Bai, Lingfei, International Preliminary Report on Patentability and Written Opinion, The International Bureau of WIPO, PCT/US2012/022114 dated Jul. 23, 2013.
Banerjee et al., 'Control of Pore Size and Functionality in Isoreticular Zeolitic Imidazolate Frameworks and their Carbon Dioxide Selective Capture Properties,' J. Am. Chem. Soc. 131:3875-3877 (2009).
Banerjee et al., 'High-Throughput Synthesis of Zeolitic Imidazolate Frameworks and Application to CO2 Capture,' Science, 2008, pp. 939-943, vol. 319.

Barman et al., 'Azulene Based Metal-Organic Frameworks for Strong Adsorption of H2,' Chem. Commun. 46:7981-7983 (2010).
Barman et al., 'Incorporation of active metal sites in MOFs via in situ generated ligand deficient metal-linker complexes' Chem. Commun. 47:11882-11884 (Oct. 11, 2011).
Barman et al., "Incorporation of active metal sites in MOFs via in situ generated ligand deficient metal-linker complexes", Chem. Comm., 2011, pp. 1-3.
Barton et al., 'Tailored Porous Materials,' Chem. Mater. 11:2633-2656 (1999).
Becamel, Philippe, International Preliminary Report on Patentability, PCT/US2012/023516, The International Bureau of WIPO, dated Aug. 6, 2013.
Becamel, Philippe, International Preliminary Report on Patentability, PCT/US2012/059877, The International Bureau of WIPO, dated Sep. 18, 2014.
Bhakta et al., 'Metal organic frameworks as templates for nanoscale NaAlH4', Journal of American Chemical Society, vol. 131, No. 37, Sep. 23, 2009, pp. S1-S14.
Bjai, Lingfei, International Preliminary Report on Patentability and Written Opinion, PCT/US2015/021107, The International Bureau of WIPO, dated Sep. 20, 2016.
Bloch et al., 'Metal Insertion in a Microporous Metal-Organic Framework Lined with 2,2'-Bipyridine' J. Am. Chem. Soc. 132:14382-14384 (2010).
Bork, Ana-Marie., International Search Report for PCT/US2011/24671, European Patent Office, dated Nov. 30, 2011.
Braun et al., '1,4-Benzenedicarboxylate Derivatives as Links in the Design of Paddle-Wheel Units and Metal-Organic Frameworks,' Chem. Commun. 24:2532-2533 (2001).
Britt et al., 'Highly efficient separation of carbon dioxide by a metal-organic framework replete with open metal sites,' Proc. Natl. Acad. Sci. USA 106:20637-20640 (2009).
Britt et al., 'Ring-Opening Reactions Within Metal-Organic Frameworks,' Inorg. Chem. 49:6387-6389 (2010).
Britt et al., "Metal-Organic frameworks with high capacity and selectivity for harmful gases", PNAS, 2008, vol. 105, No. 33, pp. 11623-11627.
Burrows et al., 'Post-Synthetic Modification of Tagged MOFs,' Angew. Chem. Int. Ed. 47:8482-8486 (2008).
Burrows, Andrew D., et al., "Post-Synthetic Modification of Tagged MOFs", Angewa. Chem. Int . Ed., (Oct. 20, 2008), vol. 47, pp. 8482-8486, XP008150669.
Carboni et al., "Highly porous and stable metal-organic frameworks for uranium extraction," Chemical Science, 1:2396-2402, Apr. 4, 2013.
Carlucci et al., 'Nanoporous three-dimensional networks topologically related to cooperite from the self-assembly of copper(I)centres and 1,2,4,5-tetracyanobenzene,' New J. Chem. 23(23):397-401 (1999).
Carlucci, Lucia etal., 'Polycatenation, polythreading and polyknotting in coordination network chemistry' Coordination Chemistry Reviews 246, 2003, pp. 247-289.
Caskey et al., 'Dramatic Tuning of CO2 Uptake via Metal Substitution in a Coordination Polymer with Cylindrical Pores,' JACS 130(33):10870-10871 (2008).
Caskey et al., 'Selected Applications of Metal-Organic Frameworks in Sustainable Energy Technologies,' Material Matters 4.4:111 (2009).
Centrone et al., 'Raman Spectra of Hydrogen and Deuterium Adsorbed on a Metal-Organic Framework,' Chem. Phys. Lett. 411:516-519 (2005).
Chae et al., 'A Route to High Surface Area, Porosity and Inclusion of Large Molecules in Crystals,' Nature427, 523-527 (2004); Featured in (1) Chemical & Engineering News magazine, Feb. 9, 2004, (2) BBC World Service, Feb. 2004, (3) New Scientist, Feb. 2004.
Chae et al., 'Design of Frameworks with Mixed Triangular and Octahedral Building Blocks Exemplified by the Structure of [Zn40(TCA)2] Having the Pyrite Topology,' Angew. Chem. Int. Ed. 42:3907-3909 (2003).
Chae et al., 'Tertiary Building Units: Synthesis, Structure, and Porosity of a Metal-Organic Dendrimer Framework (MODF-1),' J. Am. Chem. Soc, 2001, 123, 11482-11483.

(56) References Cited

OTHER PUBLICATIONS

Chambron, Jean-Claude, "Interlacing molecular threads on transition metals", Pure and Applied Chemistry, 1990, 62 (6), 1027-1034.
Che et al., "Mono- and Diprotonation of the [(n5-C5H5)Ti(W5O18)]3- and [(n5-O5Me5)Ti(W5O18)]3-Anions," Inorg. Chem. 1992, 31, 2920-2928.
Chen et al. "Photoluminescent Metal-Organic Polymer Constructed from Trimetallic Clusters and Mixed Carboxylates", Inorg. Chem. 2003, 42, 944-946.
Chen et al., 'A Microporous Metal-Organic Framework for Gas-Chomatographic Separation of Alkanes,' Angew. Chem. Int. Ed. 45:1390-1393 (2006).
Chen et al., 'Cu2(ATC) 6H20: Design of Open Metal Sites in Porous Metal-Organic Crystals (ATC: 1,3,5,7-adamantane tetracarboxylate),' J. Am. Chem. Soc, 2000,122,11559-11560.
Chen et al., 'High H2 Adsorption in a Microporous Metal-Organic Framework with Open-Metal Sites,' Angew. Chem. Int. Ed. 44:4745-4749 (2005).
Chen et al., 'Interwoven Metal-Organic Framework on a Periodic Minimal Surface with Extra-Large Pores,' Science, 2001, 291,1021-1023: Featured in Chemical and Engineering News, Feb. 21, 2001.
Chen et al., 'Noncovalently Netted, Photoconductive Sheets with Extremely High Carrier Mobility and Conduction Anisotropy from Triphenylene-Fused Meetal Trigon Conjugates,' In. J. Am. Chem. Soc. 131:7287-7297 (2009).
Chen et al., 'Transformation of a Metal-Organic Framework from the NbO to PtS Net,' Inorg. Chem. 41:181-183 (2005).
Chen, Binling, et. al., "Zeolitic imidazolate framework materials: recent progress in synthesis and applications", Journal of Materials Chemistry A: Materials for Energy and Sustainability, GB, (20140717), vol. 2, No. 40, doi:10.1039/C4TA02984D, ISSN 2050-7488, pp. 16811-16831, XP055337959.
Cho et al., 'A metal-organic framework material that functions as an enantioselective catalyst for olefin epoxidation,' Chem. Comm. 24:2563-2565 (2006).
Choi et al., 'Heterogeneity within Order in Crystals of a Porous Metal Organic Framework,' J. Am. Chem. Soc. 133:11920-11923 (2011).
Choi et al., 'Reversible Interpenetration in a Metal-Organic Framework Triggered by Ligand Removal and Addition,' Angew. Chem. Int. Ed. 51:8791-8795 (2012).
Tranchemontagne et al. 'Metal-Organic Frameworks with High Capacity and Selectivity for Harmful Gases,' Proc. Natl. Acad. Sci. USA 105:11623-11627 (2008).
Tranchemontagne et al. 'Secondary Building Units, Nets and Bonding in the Chemistry of Metal-Organic Frameworks,' Chem. Soc. Rev. 38:1257-1283 (2009).
Tranchemontagne et al. "Hydrogen Storage in New Metal-Organic Frameworks, " J. Phys. Chem. C 116, (24):13143-13151.
Tranchemontagne et al., 'Hydrogen Storage in New Metal-Organic Frameworks,' J. Phys. Chem. C 116 (24):13143-13151 (May 24, 2012).
Tranchemontagne et al., 'Reticular Chemistry of Metal-Organic Polyhedra,' Angew. Chem. Int. Ed., 2008, 47:5136-5147 (2008).
Tranchemontagne et al., 'Room Temperature Synthesis of Metal-organic Frameworks: MOF-5, MOF-74, MOF-177, MOF-199, and IRMOF-0,' Tetrahedron 64:8553-8557 (2008).
Uribe-Romo et al., 'A Crystalline Imine-Linked 3-D Porous Covalent Organic Framework,' J. Am. Chem. Soc. 131:4570-4571 (2009).
Uribe-Romo et al., 'Crystalline Covalent Organic Frameworks with Hydrazone Linkages,' J. Am. Chem. Soc. 133: 11478-11481 (2011).
Vairaprakash et al., 'Synthesis of Metal-Organic Complex Arrays,' J. Am. Chem. Soc. 133:759-761 (2011).
Valente et al., 'Metal-organic Frameworks with Designed Chiral Recognition Sites,' Chem. Commun. 46:4911-4913 (2010).
Vitillo et al., 'Role of Exposed Metal Sites in Hydrogen Storage in MOFs,' J. Am. Chem. Soc. 130(26):8386-8396 (2008).
Vodak et al., 'Computation of Aromatic C3N4 Networks and Synthesis of the Molecular Precursor N(C3N3)3C16,' Chem. Eur. J. 9:4197-4201 (2003).

Vodak et al., 'Metal-Organic Frameworks Constructed from Pentagonal Antiprismatic and Cuboctahedral Secondary Building Units,' Chem. Commun. 2534-2535 (2001).
Vodak et al., 'One-Step Synthesis and Structure of an Oligo(spiro-orthocarbonate),' J. Am. Chem. Soc.124 (18):4942-4943 (2002).
Walton et al., 'Understanding Inflections and Steps in Carbon Dioxide Adsorption Isotherms in Metal-Organic Frameworks,' J. Am. Chem. Soc. 130:406-407 (2008).
Wan et al, 'A Belt-Shaped, Blue Luminescent, and Semiconducting Covalent Organic Framework.' Angew. Chem. Int. Ed. 47:8826-8830 (2008).
Wan et al., 'Covalent Organic Frameworks with High Charge Carrier Mobility,' Chem. Mater. 23:4094-4097 (Aug. 22, 2011).
Wang et al., 'Colossal Cages in Zeolitic Imidazolate Frameworks as Selective Carbon Dioxide Reservoirs,' Nature 453:207-211 (2008).
Wang et al., 'Postsynthetic Covalent Modification of a Neutral Metal-Organic Framework,' J. Am. Chem. Soc. 129 (41):12368-12369 (2007).
Wang et al., 'Tandem Modification of Metal-Organic Frameworks by a Postsynthetic Approach,' Angew. Chem. Int. 47:4699-4702 (2008).
Wang, Yiting, First Office Action, Chinese Patent Application No. CN201080036940.6, dated Dec. 4, 2013.
Wang, Zhenqiang, et al., 'Postsynthetic Covalent Modification of a Neutral Metal—Organic Framework', J. Am. Chem. Soc., (2007), vol. 129, No. 41, pp. 12368-12369.
Wardencki et al. Green Chemistry—Current and Future Issues. Review. Polish Journal of Environmental Studies. 2005. vol. 14, No. 4, pp. 389-395.
Whiffield et al. Metal-organic frameworks based on iron oxide octahedral chains connected by benzendicarboxylate dianions. Solid State Sciences, 2005. vol. 7, pp. 1096-1103.
Wong-Foy, Ag et al., 'Exceptional H2 Saturation uptake in microporous metal-organic frameworks' J. Am. Chem. Soc, 2006, 128, pp. 3494-3495.
Wu et al., 'Structural Study of New Hydrocarbon Nano-Crystals by Energy-Filtered Electron Diffraction,' Ultramicroscopy 98:145-150 (2004).
Nu et al., 'Structural Study of New Hydrocarbon Nano-Crystals by Energy-Filtered Electron Diffraction,' Ultramicroscopy 98:145-150 (2004).
Yaghi et al., 'A Molecular Railroad with Large Pores: Synthesis and Structure of Ni(4,4'-bpy)2.5(H20)2(Cl04)2.1.5(4,4'-bpy)2(H2O),' Inorg. Chem., 1997, 36, 4292-4293.
Yaghi et al., 'A Molecular World Full of Holes,' Chem. Innov. p. 3 (2000).
Yaghi et al., 'Construction of a New Open-Framework Solid from 1,3,5-Cyclohexanetricarboxylate and Zinc(II) Building Blocks,' J. Chem. Soc, Dalton Trans., 1997, 2383-2384.
Yaghi et al., 'Construction of Microporous Materials from Molecular Building Blocks,' Fundamental Materials Research, T. J. Pinnavaia and M. F. Thorpe, eds., vol. II, Plenum: New York, p. 111 (1995).
Yaghi et al., 'Construction of Porous Solids from Hydrogen-Bonded Metal Complexes of 1,3,5-Benzenetricarboxylic Acid,' J. Am. Chem. Soc, 1996, 118, 9096-9101.
Yaghi et al., 'Conversion of Hydrogen-Bonded Manganese(II) and Zinc(II) Squarate (C4042-) Molecules, Chains, and Sheets to 3-D Cage Networks,' J. Chem. Soc, Dalton Trans., 1995, 727-732.
Yaghi et al., 'Conversion of Molecules and Clusters to Extended 3-D Cage and Channel Networks,' Metal Containing Polymeric Materials, C. U. Pittman, C. E. Carraher, B. M. Culbertson, M. Zeldin, J. E. Sheets, Eds., Plenum: New York p. 219(1996).
Yaghi et al., 'Crystal Growth of Extended Solids by Nonaqueous Gel Diffusion,' Chem. Mater., 1997, 9, 1074-1076.
Yaghi et al., 'Design of Solids Molecular Building Blocks: Golden Opportunities for Solid State Chemistry,' J. Solid State Chem. 152, 1-2 (2000).
Yaghi et al., 'Designing Microporosity in Coordination Solids,' Modular Chemistry, J. Michl (ed.), Kluwer Academic Publishers, p. 663-670 (1997).

(56) References Cited

OTHER PUBLICATIONS

Yaghi et al., 'Hydrothermal Synthesis of a Metal-Organic Framework Containing Large Rectangular Channels,' J. Am. Chem. Soc, 1995, 117, 10401-10402.
Yaghi et al., 'Metal-Organic Frameworks: A Tale of Two Entanglements,' Nature materials 6:92-93 (2007).
Yaghi et al., 'Mutually Interpenetrating Sheets and Channels in the Extended Structure of Cu(4,4'-Bipyridine)Cl,' Angew. Chem. Int. Ed. Engl., 1995, 34, No. 2, 207-209.
Yaghi et al., 'Open-Framework Solids with Diamond-Like Structures Prepared from Clusters and Metal-Organic Building Blocks,' Mater. Res. Soc. Symp. Proc, 1995, 371, 15.
Yaghi et al., 'Reticular Chemistry and Metal-Organic Frameworks for Clean Energy,' MRS Bulletin 34:682-690 (2009).
Yaghi et al., 'Reticular Synthesis and the Design of New Materials,' Nature 423:705-714 (2003).
Yaghi et al., 'Selective binding and removal of guests in a microporous metal-organic framework,' Nature, Dec. 1995, pp. 703-706, vol. 378.
Yaghi et al., 'Selective Guest Binding by Tailored Channels in a 3-D Porous Zinc(II)-1,3,5-Benzenetricarboxylate Network,' J. Am. Chem. Soc, 1997, 119, 2861-2868.
Yaghi et al., 'Synthesis and Structure of a Metal-Organic Solid Having the Cadmium (II) Sulfate Net,' Mater. Res. Soc. Symp. Proc. 453:127, (1997).
Yaghi et al., 'Synthetic Strategies, Structure Patterns, and Emerging Properties in the Chemistry of Modular Porous Solids,' Acc. Chem. Res. 31:474-484 (1998).
Yaghi et al., 'T-Shaped Molecular Building Units in the Porous Structure of Ag(4,4'-bpy) N03,' J. Am. Chem. Soc, 1996, 118, 295-296.
Yaghi et al., 'Transformation of Germanium Dioxide to 4-Connected Porous Germanate Net,' J. Am. Chem. Soc, 20:10569-10570(1998).
Yaghi et al., "Directed Transformation of Molecules to Solids: Synthesis of a Microporous Sulfide from Molecular Germanium Sulfide Cages", J. Am. Chem. Soc. 1994, 116, 807-808.
Llabres, Francesc X. et al., 'Activity, reusability and shape-sensitivity of a Pd-containing MOF', Journal of catalysis, Sep. 10, 2007, 250, pp. 294-298.
Loeb, 'Rotaxanes as ligands: from molecules to materials', Chem. Soc. Rev., 2007, 36, 226-235.
Long et al., 'The Pervasive Chemistry of Metal-Organic Frameworks,' Chem. Soc. Rev. 38:1213-1214 (2009).
Lu et al., 'Synthesis and Structure of Chemically Stable Metal-Organic Polyhedra,' J. Am. Chem. Soc. 131:(35) 12532-12533 (2009).
Luo et al., 'Two new metal-triazole-benzenedicarboxylate frameworks affording an uncommon 3,4-connected net and unique 4,6-connected rod packing: hydrothermal synthesis, structure, thermostability and luminescence studies,' CrystEngComm 11 (6): 1097-1102 (2009).
Mashiyama, Shinya, Office Action issued in Japanese Patent Application No. 2012-522962, Japanese Patent Office, dated May 27, 2014.
Mason, Jarad A., "Evaluating metal-organic frameworks for natural gas storage", Chemical Science, vol. 5, Accepted Oct. 22, 2013, pp. 32-51.
McDonald, Thomas M. et al., 'Capture of Carbon Dioxide from Air and Flue Gas in the Alkylamine-Appended Metal-Organic Framework mmen-Mg 2 (dobpdc)', Journal of the American Chemical Society, vol. 134, No. 16, Apr. 4, 2012, pp. 7056-7065.
McKeown et al., 'Phthalocyanine-Based Nanoporous Network Polymers,' Chem. Comm. 23:2780-2781 (Oct. 31, 2002).
McKeown et al., 'Porphyrin-Based Nanoporous Network Polymers,' Chem. Comm. 23:2782-2783 (Oct. 31, 2002).
Mendoza-Cortes et al., 'Adsorption Mechanism and Uptake of Methane in Covalent Organic Frameworks: Theory and Experiment,' J. Phys. Chem. 114:10824-10833 (2010).
Michalitsch, Richard, International Search Report and Written Opinion for PCT/US2009/069700, European Patent Office, dated May 7, 2010.
Millward et al., 'Metal-Organic Frameworks with Exceptionally High Capacity for Storage of Carbon Dioxide at Room Temperature,' J. Am. Chem. Soc. 127:17998-17999 (2005).
Mineko Mohri, International Preliminary Report on Patentability and Written Opinion, PCT/US2015/016555, The International Bureau of WIPO, dated Sep. 1, 2016.
Morris et al., 'A Combined Experimental—Computational Investigation of Carbon Dioxide Capture in a Series of Isoreticular Zeolitic Imidazolate Frameworks,' J. Am. Chem. Soc. 132:11006-11008 (2010).
Morris et al., 'Crystals as Molecules: Postsynthesis Covalent Functionalization of Zeolitic Imidazolate Frameworks,' J. Am. Chem. Soc. 130:12626-12627 (2008).
Morris et al., 'Framework mobility in the metal-organic framework crystal IRMOF-3: Evidence for aromatic ring and amine rotation,' Journal of Molecular Structure 1004:94-101 (2011).
Morris et al., 'NMR and X-ray Study Revealing the Rigidity of Zeolitic Imidazolate Frameworks,' J. Phys. Chem. 116 (24)13307-13312 (Jun. 1, 2012).
Morris et al., 'Postsynthetic Modification of a Metal-Organic Framework for Stabilization of a Hemiaminal and Ammonia Uptake,' Inorg. Chem. 50:6853-6855 (2011).
Morris et al., 'Synthesis, Structure, and Metalation of Two New Highly Porous Zirconium Metal-Organic Frameworks,' Inorg. Chem. 51:6443-6445 (Jun. 7, 2012).
Morris, et al., 'Crystals as Molecules: Postsynthesis Covalent Functionalization of Zeolitic Imidazolate Frameworks', J. Am. Chem. Soc., (Aug. 2008), vol. 130, No. 38, pp. 12626-12627.
Moyse, Ellen, International Preliminary Report on Patentability and Written Opinion, dated Nov. 17, 2009, International Application No. PCT/US08/006008.
Moyse, Ellen, International Preliminary Report on Patentability and Written Opinion, PCT/US08/006008, The International Bureau of WIPO, dated Nov. 26, 2009.
Mulfort et al., 'Chemical Reduction of Metal-Organic Framework Materials as a Method to Enhance Gas Uptake and Binding,' J. Am. Chem. Soc. 129:9604-9605 (2007).
Mulhausen, Dorothee, International Preliminary Report on Patentability, PCT/US2009/069700, The International Bureau of WIPO, dated Jul. 7, 2011.
Mulhausen, Dorothee, International Preliminary Report on Patentability, PCT/US2010/021201, The International Bureau of WIPO, dated Jul. 28, 2011.
Mulhausen, Dorothee. International Preliminary Report on Patentability for PCT/US2010/021201, dated Jul. 28, 2011.
Natarajan et al., 'Non-carboxylate based metal-organic frameworks (MOFs) and related aspects,' Current Opinion in Solid State and Materials Science 13(3-4):46-53 (2009).
Nickitas-Etienne, Athina, International Preliminary Report on Patentability and Written Opinion, Date of Issuance of the Report: dated Jan. 19, 2010, International Application No. PCT/US08/70149.
Nickitas-Etienne, Athina, International Preliminary Report on Patentability and Written Report, Application No. PCT/US2015/021090, dated Sep. 20, 2016.
Nickitas-Etienne, Athina, International Preliminary Report on Patentability for PCT/US2009/068731, dated Jun. 21, 2011.
Nickitas-Etienne, Athina, International Preliminary Report on Patentability, PCT/US2009/068731, The International Bureau of WIPO, dated Jun. 30, 2011.
Nickitas-Etienne, Athina, International Preliminary Report on Patentability,PCT/US2008/077741, The Internationa Bureau of WIPO, dated Mar. 30, 2010.
Nickitas-Etienne, Athina. International Preliminary Report on Patentability for PCT/US2009/068849, dated Jun. 30, 2011.
Niu et al., 'Synthesis and structural characterization of the one dimensional polymers [Rh2(OAc)4(NCPhCN)S, S =CH3COCH3, CH30H, C2H50H, C4H80, and C6H6,' Polyhedron 17(23-24):4079-89 (1998).

(56) References Cited

OTHER PUBLICATIONS

Ni et al., 'Porous Metal-Organic Truncated Octahedron Constructed from Paddle-Wheel Squares and Terthiophene Links,' J. Am. Chem. Soc. 127:12752-12753 (2005).
Novoa, Carlos, International Search Report and Written Opinion for PCT/US2010/021201, European Patent Office, dated Apr. 27, 2010.
O'Keefe et al., 'Germanate Zeolites: Contrasting the Behavior of Germanate and Silicate Structures Built from Cubic T8O20 units (T = Si or Ge),' Chem. Eur. J., 1999, 5, 2796-2801.
O'Keeffe et al., 'Deconstructing the Crystal Structures of Metal-Organic Frameworks and Related Materials into Their Underlying Nets,' Chem. Rev. 112(2):675-702 (Feb. 8, 2012).
O'Keeffe et al., 'Frameworks for Extended Solids: Geometrical Design Principles,' J. Solid State Chem. 152:3-20 (2000).
O'Keeffe et al., 'The Reticular Chemistry Structure Resource (RCSR) Database of, and Symbols for, Crystal Nets,' Am. Chem. Res. 41:1782-1789 (2008).
Meneses, Ociel Esau Andrade, First Office Action, Mexican Application No. MX/a/2013/00469, Mexican Institute of Industrial Property (IMPI), dated Jan. 26, 2015.
Ockwig et al., 'Reticular Chemistry: Occurrence and Taxonomy of Nets, and Grammar for the Design of Frameworks,' Acc. Chem. Res. 38:176-182 (2005).
Oisaki et al., "A Metal-Organic Framework with Covalently Bound Organometallic Complexes," J. of the Amer. Chem. Soc., pp. 9262-9264, vol. 132, No. 27, 2010.
Okeefffe et al., 'Reticular Chemistry—Present and Future Prospects—Introduction,' J. Solid State Chem.178:V-VI (2005).
Park, H. et al., 'Synthesis, Structure Determination and Hydrogen Sorption Studies of New Metal-Organic Frameworks Using Triazole and Naphthalenedicarboxylic Acid', Chem. Natur. 19:1302-1308 (2007).
Park, Jae Woo. International Search Report for PCT/US2010/039123, Korean Intellectual Property Office, dated Feb. 24, 2011.
Park, Jae Woo. International Search Report for PCT/US2010/039123, dated Feb. 24, 2011.
Park, Kyo Sung et al., 'Exceptional chemical and thermal stability of zeolitic imidazolate frameworks,' Proc. Natl. Acad. Sci., Jul. 5, 2006, vol. 103, No. 27, pp. 10186-10191.
Patteux, Claudine, International Search Report and Written Opinion, Application No. PCT/US2010/043373, dated Oct. 6, 2010.
Yaghi et al., "Preparation of Single Crystals of Coordination Solids in Silica Gels: Synthesis and Structure of CuII (1,4-C4H4N2)(C4O4)(OH2)4", Journal of Solid State Chemistry, 117, 256-260 (1995).
Yaghi et al., "Rhenium-Selenium-Chlorine Solid Phases: Cluster Excision and Core Substitution Reactions of Molecular Species", Inorg. Chem. 1992, 31, 4778-4784.
Yaghi, Omar, 'Hydrogen Storage in Metal-Organic Frameworks,' slide presentation to DOE Hydrogen Program 2007 Annual Merit Review, US Department of Energy, on May 15,2007 at http://www.hydrogen.energy.gov/pdfs/review07/St_10_yaghi.pdf.
Yaghi, Omar., 'Porous Crystals for Carbon Dioxide Storage,' slide presentation at the Fifth Annual Conference on Carbon Capture & Sequestration, US Department of Energy on May 10, 2006 http://www.netl.doe.gov/publications/proceedings/06/carbon-seqirech.degre- e.20Session.degree.20193.pdf.
Yang et al. 'Two Novel Triazole-Based Metal-Organic Frameworks Consolidated by a Flexible Dicarboxylate Co-ligand: Hydrothermal Synthesis, Crystal Structure, and Luminescence Properties,' Australian Journal of Chemistry 61 (10):813-820 (2008).
Yang et al., 'CH4 storage and C02 capture in highly porous zirconium oxide based metal-organic frameworks,' Chem. Commun., 48:9831-9833, Aug. 15, 2012.
Yang et al., 'Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties,' Crystal Growth Design 7(10):2009-2015 (2007).
Young, Jung Doo, International Search Report & Written Opinion, Korean Application No. PCT/US2011/044625, dated Feb. 24, 2012.
Young, Jung Doo, International Search Report and Written Opinion, Application No. PCT/US2010/050170, dated Jun. 8, 2011.
Young, Jung Doo, International Search Report and Written Opinion, Application No. PCT/US2012/022114, dated Aug. 22, 2012.
Young, Jung Doo, Written Opinion, PCT/US2011/053423, Korean Intellectual Property Office, dated Jul. 23, 2012.
Young, Jung Doo. International Search Report and Written Opinion for PCT/US2011/053423, dated Jul. 23, 2012.
Young, Lee W., 'International search Report and Written Opinion,' PCT/US08/06008, United States Patent & Trademark Office, dated Aug. 20, 2008.
Young, Lee W., International Search Report and Written Opinion, Application No. PCT/US08/70149, dated Jan. 12, 2009.
Young, Lee W., International Search Report and Written Opinion, dated May 7, 2008, International Application No. PCT/US08/51859.
Young, Lee W., International Search Report and Written Opinion, dated Dec. 2, 2008, International Application No. PCT/US08/77741.
Young, Lee W., International Search Report and Written Opinion, dated Jan. 12, 2009, International Application No. PCT/US08/70149.
Zhang et al., 'Crystal engineering of binary metal imidazolate and triazolate frameworks,' Chem. Comm. 1689-1699 (2006).
Zhang et al., 'Syntheses, Structures, and Porous/Luminescent Properties of Silver 3-Alkyl-1,2,4-Triazolate Frameworks with Rare 3-Connected Topologies,' Crystal Growth and Design 11:796-802 (2011).
Zhang et al., 'Exceptional Framework Flexibility and Sorption Behavior of a Multifunctional Porous Cuprous Triazolate Framework,' J. Am. Chem. Soc. 130:6010-6017 (2008).
Zhao et al., 'Rigid-Strut-Containing Crown Ethers and [2]Catenanes for Incorporation into Metal-Organic Frameworks,' Chem. Eur. J. 15:13356-13380 (2009).
Zhao, Office Action in Chinese Patent Application No. 20088031572, dated Aug. 5, 2011.
Zhao, Wei, First Office Action for Chinese Application No. 200880003157.2, The State Intellectual Property Office of the People's Republic of China, dated Aug. 5, 2011.
Zhaofu et al., 'A Nearly Planar Water Sheet Sandwiched between Strontium-Imidazolium Carboxylate Coordination Polymers,' Inorg. Chem. 44:5200-5202 (2005).
Zhenqiang Wang et al., 'Tandem Modification of Metal-Organic Frameworks by a Postsynthetic Approach', Angew Chem Int Ed, (200800686), vol. 47, pp. 4699-4702.
Zhou et al., 'Introduction to Metal-Organic Frameworks,' Chemical Reviews 112:673-674 (Jan. 26, 2012).
Zhou, X et al., 'Hydrothermal Syntheses and Structures of Three Novel Coordination Polymers Assembled from 1,2,3-Triazolate Ligands,' CrystEngComm. 11:1964-1970 (2009).
Zhu, A. et al., 'Isomeric Zinc(II) Triazolate Frameworks with 3-Connected Networks: Syntheses, Structures, and Sorption Properties,' Inorg. Chem. 48:3882-3889 (2009).
Zou et al., "Novel Eclipsed 2D Cadmium(II) Coordination Polymers with Open-Channel Structure Constructed from Terephthalate and 3-(2-Pyridyl)pyrazole: Crystal Structures, Emission Properties, and Inclusion of Guest Molecules", Inorg. Chem. 2004, 43, 5382-5386.
Fang et al. A Metal-Organic Framework with the Zeolite MTN Topology Containing Large Cages of vol. 2.5 nm3. Ang Chem Int Ed 2005, vol. 44, pp. 3845-3848.
Fei et al., 'A Nearly Planar Water Sheet Sndwiched between Strontium-Imidazolium Carboxylate Coordination Polymers,' Inorg. Chem., 2005, pp. 5200-5202, vol. 44.
Ferragut et al., 'Positronium Formation in Porous Materials for Antihydrogen Production,' J. Phys. Conf. Ser. 225:1-8 (2010).
Finger, Gabriela, International Search Report and Written Opinion, PCT/US2010/043373, European Patent Office, dated Oct. 6, 2010.
Finger, Gabriela, International Search Report and Written Opinion, PCT/US2015/021107, European Patent Office, dated Aug. 17, 2015.
First Office Action issued in Chinese Patent Application No. 201180045210.8, dated Sep. 28, 2014.

(56) References Cited

OTHER PUBLICATIONS

Forster et al., 'A High-Throughput Investigation of the Role of pH, Temperature, Concentration, and Time on the Synthesis of Hybrid Inorganic-Organic Materials,' Angew. Chemie Int. Ed. 44(46):7608-7611 (2005).

Fracaroli et al., 'Isomers of Metal-Organic Complex Arrays,' Inorg. Chem. 51: 6437-6439 (Jun. 5, 2012).

Furukawa et al., 'Control of Vertex Geometry, Structure Dimensionality, Functionality, and Pore Metrics in the Reticular Synthesis of Crystalline Metal-Organic Frameworks and Polyhedra,' J. Am. Chem. Soc.130:11650-11661 (2008).

Furukawa et al., 'Crystal Structure, Dissolution, and Deposition of a 5 nm Functionalized Metal-Organic Great Rhombicuboctahedron,' J. Am. Chem. Soc. 128:8398-8399 (2006).

Furukawa et al., 'Independent verification of the saturation hydrogen uptake in MOF-177 and establishment of a benchmark for hydrogen adsorption in metal-organic frameworks,' J. Mater. Chem. 17:3197-3204 (2007).

Furukawa et al., 'Isoreticular Expansion of MetalOrganic Frameworks with Triangular and Square Building Units and the Lowest Calculated Density for Porous Crystals,' Inorg. Chem. 50:9147-9152 (2011).

Furukawa et al., 'Storage of Hydrogen, Methane, and Carbon Dioxide in Highly Porous Covalent Organic Frameworks for Clean Energy Applications,' J. Am. Chem. Soc. 25:8876-8883 (2009).

Furukawa et al., 'Ultra-High Porosity in Metal-Organic Frameworks,' Science 239:424-428 (2010).

Furukawa et al., "Water Adsorption in Porous Metal-Organic Frameworks and Related Materials," J. of the Amer. Chem. Soc, vol. 136, No. 11, pp. 4369-4381, Published: Mar. 3, 2014.

Gadzikwa, T. et al., 'Selective Bifunctional Modification of a Non-catenated Metal-Organic Framework Material via slick Chemistry,' J. Am. Chem. Soc. 131:13613-13615 (2009).

Galli et al., 'Adsorption of Harmful Organic Vapors by Flexible Hydrophobic Bis-pyrazolate Based MOFs,' Chem. Mater. 22(5):1664-1672 (2010).

Gandara, Felipe, et al., "Crystallography of metal-organic frameworks", IUCRJ, vol. 1, No. 6, Oct. 28, 2014, pp. 563-570.

Gandara et al., 'High Methane Storage Capacity in Aluminum Metal-Organic Frameworks', Journal of the American Chemical Society, vol. 136, No. 14, Mar. 21, 2014, pp. 5271-5274.

Gandara et al., 'Porous, Conductive Metal-Triazolates and Their Structural Elucidation by the Charge-Flipping Method,' Chem. Eur. J. 18:10595-10601 (2012).

Garibay et al., "Isoreticular synthesis and modification of frameworks with the UiO-66 topology," Chemical Communications, 46:7700-7702, Sep. 27, 2010.

Gassensmith et al., 'Strong and Reversible Binding of Carbon Dioxide in a Green Metal-Organic Framework,' J. Am. Chem. Soc. 133:15312-15315 (Aug. 30, 2011).

Glover et al., 'MOF-74 building unit has a direct impact on toxic gas adsorption,' J. Chem. Eng. Sci. 66:163-170 (2011).

Goebel, Matthias, Supplemental European Search Report and Written Opinion for EP08754337. Date of Completion of Search and Written Opinion: Dec. 3, 2010.

Goebel, Matthias, Supplemental European Search Report and Written Opinion for EP08826913. Date of Completion of Search and Written Opinion: Nov. 10, 2010.

Gonzalez-Arellano et al., 'Homogeneous and heterogeneous Au(III) Schiff base-complexes as selective and general catalysts for self-coupling of aryl boronic acids,' Chem. Comm. 15:1990-1992 (2005).

Goto, Y et al., "Clickable Metal-Organic Framework," J. Am. Chem. Soc. 130:14354-14355 (2008).

Gould et al., "Amphidynamic Character of Crystalline MOF-5: Rotational Dynamics of Terephthalate Phenylenes in a Free-Volume, Sterically Unhindered Environment", J. Am. Chem. Soc. 130:3246-3247 (2008).

Grzesiak et al., 'Polymer-Induced Heteronucleation for the Discovery of New Extended Solids,' Angew. Chem. Int. Ed. 45:2553-2556 (2006).

Halper et al., 'Topological Control in Heterom etal lie Metal-Organic Frameworks by Anion templating and Metalloligand Design,' J. Am. Chem. Soc, 2006, pp. 15255-15268, vol. 128.

Han et al., 'Covalent Organic Frameworks as Exceptional Hydrogen Storage Materials,' J. Am. Chem. Soc. 130: 11580-11581 (2008).

Han, SS et al., 'Improved designs of metal-organic frameworks for hydrogen storage', Angew. Chem. Int. Ed., 2007, 46, pp. 6289-6292.

Hassan et al., "Aryl-Aryl Bond Formation One Century After the Discovery of the Ullmann Reaction", Chem. Rev., Published on Web: Mar. 8, 2002, 102, 1359-1469.

Hayashi et al., 'Zeolite A Imidazolate Frameworks,' Nature Materials 6:501-506 (Jul. 2007).

Hexiang et al., 'Multiple Functional Groups of Varying Rations in Metal-Organic Frameworks,' Science 327 (5967):846-850 (2010).

Hmadeh et al., 'New Porous Crystals of Extended Metal-Catecholates,' J. Chem. Mater. 24:3511-3513 (Aug. 28, 2012).

Holler et al., 'The first dinitrile frameworks of the rare earth elements: [LnCl3(1,4-Ph(CN)2] and [Ln2Cl6(1,4Ph(CN)2], Ln = Sm, Gd, Tb, Y; Access to novel metal-organic frameworks by solvent free synthesis in molten 1,4-benodinitrile,' Inorganic Chemistry 47(21): 10141-9 (2008).

Holler et al., "The First Dintrile Frameworks of the Rare Earth Elements: 3[LnCL3(1,4-Ph(CN2)] and 3[Ln2CL6(1,4-Ph(CN)2)], Ln=Sm, Gd, Tb, Y; Access to Novel Metal-Organic Frameworks by Solvent Free Synthesis in Molten 1,4-Benzodinitrile," Inorganic Chemistry, 2008, pp. 10141-10149, vol. 47, No. 21.

Holler, Christoph J.,et. al., "The first dinitrile frameworks of the rare earth elements: [LnCl3(1,4-Ph(CN)2] and [Ln2C16(1,4Ph(CN)2], Ln = Sm, Gd, Tb, Y;Access to novel metal-organic frameworks by solvent free synthesis in molten 1,4-benzodinitril", Inorganic Chemistry, (20080810), vol. 47, No. 21, p. 10141, XP002574067.

Honda, Masashi, International Preliminary Report on Patentability for PCT/US2008/051859, dated Jul. 28, 2009.

Howe, Patrick, International Search Report and Written Opinion, Application No. PCT/US2009/068849, dated Jun. 4, 2010.

Howe, Patrick, International Search Report and Written Opinion, Application No. PCT/US2010/022777, dated Jun. 7, 2010.

Huang et al., 'Ligand-Directed Strategy for Zeolite-Type Metal—Organic Frameworks: Zinc(II) Imidazolates with Unusual Zeolitic Topologies,' Angew. Chem. Int. Ed. 45:1557-1559 (2006).

Huang et al., 'Thermal Conductivity of Metal-Organic Framework 5 (MOF-5): Part II. Measurement,' Int. J. Heat Mass Transfer 50:405-411 (2007).

Hunt et al., 'Reticular Synthesis of Covalent Organic Borosilicate Frameworks,' J. Am. Chem. Soc. 130: 11872-11873 (2008).

Hurenkamp, Jaap, International Search Report and Written Opinion, PCTUS2015/016555, European Patent Office, dated May 6, 2015.

Ingleson et al., 'Framework fractionalization triggers metal complex binding,' Chem. Comm. 23:2680-2682 (2008).

Isaeva et al., 'Metal-organic frameworks-new materials for hydrogen storage,' Russian Journal of General Chemistry 77(4):721-739(2007).

Jeong et al., 'Asymmetric Catalytic Reactions by NbO-Type Chiral Metal-Organic Frameworks,' Chem. Sci. 2:877-882 (2011).

Jia, Xiao, The Third Office Action, Chinese Patent Application No. 201080021284.2, dated Aug. 19, 2014.

\* cited by examiner

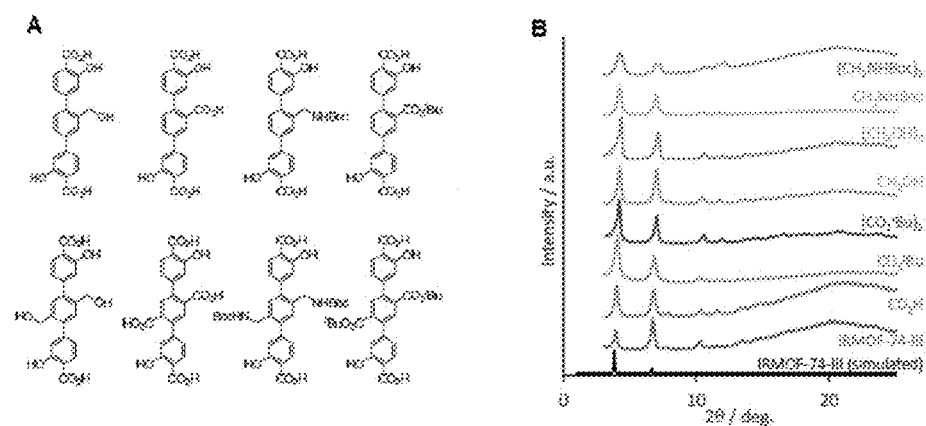
FIGURE 8A-B
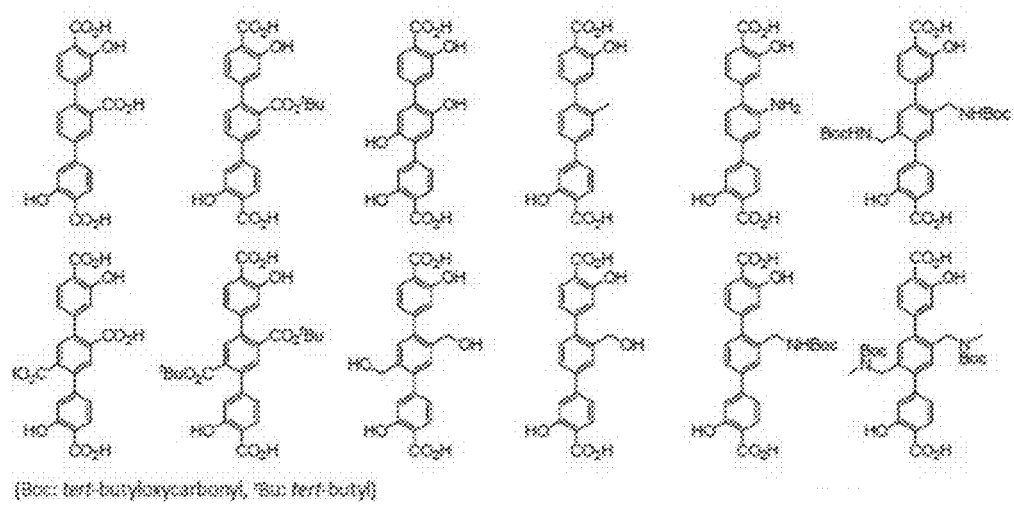
FIGURE 9

METAL ORGANIC FRAMEWORKS COMPRISING A PLURALITY OF SBUS WITH DIFFERENT METAL IONS AND/OR A PLURALITY OF ORGANIC LINKING LIGANDS WITH DIFFERENT FUNCTIONAL GROUPS

CROSS REFERENCE TO RELATED APPLICATIONS

This application is a U.S. National Stage Application filed under 35 U.S.C. § 371 and claims priority to International Application No. PCT/US2015/023173, filed Mar. 27, 2015, which application claims priority under 35 U.S.C. § 119 from Provisional Application Ser. No. 61/972,124, filed Mar. 28, 2014, the disclosures of which are incorporated herein by reference.

STATEMENT OF GOVERNMENT FUNDING

This invention was made with government support under Grant Number HDTRA 12-1-0053 awarded by the United States Department of Defense and under Grant Number DE-AR0000185 awarded by the United States Department of Energy. The government has certain rights in the invention.

TECHNICAL FIELD

The disclosure provides for metal organic frameworks (MOFs) which comprise a plurality of SBUs comprising different metals or metal ions and/or a plurality of organic linking moieties comprising different functional groups. The disclosure further provides for the use of these MOFs in variety of applications, including for gas separation, gas storage, catalysis, and water storage.

BACKGROUND

Metal-organic frameworks (MOFs) are porous crystalline nano-materials that are constructed by linking metal clusters called Secondary Building Units (SBUs) and organic linking ligands. MOFs have high surface area and high porosity which enable them to be utilized in diverse fields, such as gas storage, catalysis, and sensors.

SUMMARY

The disclosure provides a Metal-Organic Framework (MOF) comprising a plurality of secondary Building units (SBUs) that are linked together by a plurality of organic linking ligands, the MOF being selected from the group consisting of: (a) homogeneous SBUs and a plurality of organic linking ligands that have been alkyl or amine functionalized, such that alkyl or amine functional groups extend into the pores of the MOF; (b) a plurality of different SBUs and a plurality of homogeneous organic linking ligand linking the SBUs; (c) a plurality of different SBUs and a plurality of organic linking ligands that have been alkyl or amine functionalized, such that alkyl or amine functional groups extend into the pores of the MOF; and (d) a plurality of different SBUs and a plurality of organic linking ligands wherein at least two of the organic linking ligands comprise a different number or a different type of functional group(s). In one embodiment, the linking ligands comprise the structure of Formula I and/or II below.

The disclosure provides for MOFs that comprise a plurality of organic linking ligands linked to a plurality of SBUs, wherein two or more of the organic linking ligands are comprised of different types of functional groups and/or different numbers of functional groups. The disclosure also provides for MOFs that comprise a plurality organic linking ligands that are linked to a plurality of SBUs, wherein two or more of the SBUs are comprised of different metal or metal ions. The disclosure further provides for MOFs that comprise a plurality organic linking ligands linked to a plurality of different SBUs, wherein two or more organic linking are comprised of different types of functional groups and/or different numbers of functional groups and wherein two or more SBUs are comprised of different metal or metal ions.

The MOFs of the disclosure are multivariate in that the material properties can be readily modified by changing the ratio between multiple types of metal ions in SBUs or the ratio between multiple types of differently functionalized organic linking ligands. In a certain embodiment, a MOF of the disclosure is multivariate in that the material properties of the MOF can be readily modified by changing the ratio between multiple types of metal ions in SBUs and/or by changing the ratio of different types of organic linking ligands. Accordingly, a MOF of the disclosure may be topologically uniform, while not being uniform in terms of the SBU being comprised of the same metal or metal ion, and/or not being uniform in terms of the organic linking ligands having the same structure. The structural tunability of the MOFs of the disclosure therefore allows for fine-tuning of the structure. Thus, MOFs can be synthesized to have certain properties and functionality in order to meet certain intended applications, such as for gas separation, gas storage, water storage and release, or catalysis. The disclosure also provides methods to synthesize the MOFs of the disclosure.

In particular embodiment, the disclosure provides for a Metal-Organic Framework (MOF) comprising a plurality of secondary Building units (SBUs) that are linked together by a plurality of organic linking ligands, wherein at least two of the SBUs comprise different metals or metal ions and/or wherein at least two of the organic linking ligands comprise a different number or a different type of functional group(s). In a further embodiment, the plurality of organic linking ligands comprise a structure of Formula I and/or II:

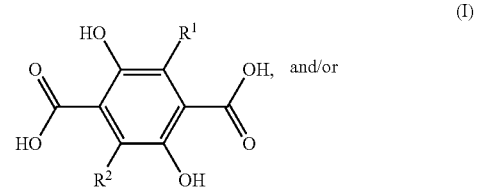

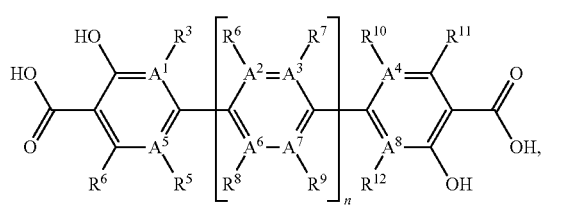

wherein, n is a number from 0 to 10; $A^1$-$A^8$ are independently a C or N; $R^1$-$R^{12}$ are independently selected from H, D, FG, optionally substituted $(C_1-C_{12})$alkyl, optionally substituted hetero-$(C_1-C_{12})$alkyl, optionally substituted $(C_1-C_{12})$alkenyl, optionally substituted hetero-$(C_1-C_{12})$alkenyl, optionally substituted $(C_1-C_{12})$alkynyl, optionally substituted hetero-$(C_1-C_{12})$alkynyl, optionally substituted $(C_1-C_{12})$cycloalkyl, optionally substituted $(C_1-C_{12})$cycloalkenyl, optionally substituted aryl, optionally substituted heterocycle, optionally substituted mixed ring system, —$C(R^{13})_3$, —$CH(R^{13})_2$, —$CH_2R^{13}$, —$C(R^{14})_3$, —$CH(R^{14})_2$, —$CH_2R^{14}$, —$OC(R^{13})_3$, $OCH(R^{13})_2$, —$OCH_2R^{13}$, —$OC(R^{14})_3$, —$OCH(R^{14})_2$, $OCH_2R^{14}$, wherein $R^4$-$R^{11}$ when adjacent can be linked together to form one or more optionally substituted rings selected from the group comprising cycloalkyl, cycloalkenyl, heterocycle, aryl, and mixed ring system; $R^{13}$ is selected from FG, optionally substituted $(C_1-C_{12})$alkyl, optionally substituted hetero-$(C_1-C_{12})$alkyl, optionally substituted $(C_1-C_{12})$alkenyl, optionally substituted hetero-$(C_1-C_{12})$alkenyl, optionally substituted $(C_1-C_{12})$alkynyl, optionally substituted hetero-$(C_1-C_{12})$alkynyl, hemiacetal, hemiketal, acetal, ketal, and orthoester; and $R^{14}$ is selected from one or more substituted or unsubstituted rings selected from cycloalkyl, aryl and heterocycle. In yet a further embodiment, the plurality of organic linking ligands comprise a structure of Formula III:

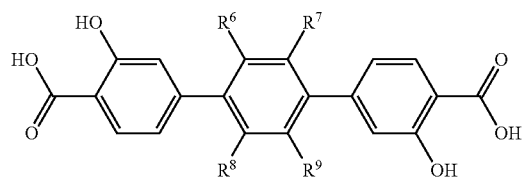

(III)

wherein, $R^6$-$R^9$ are independently selected from:

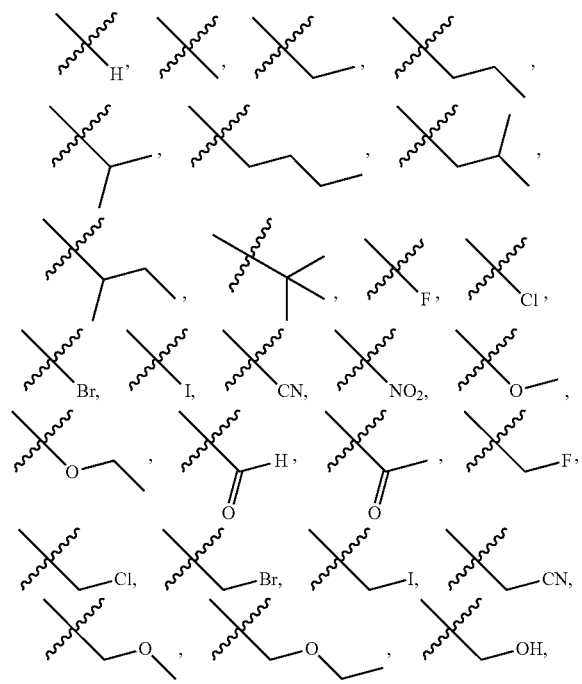

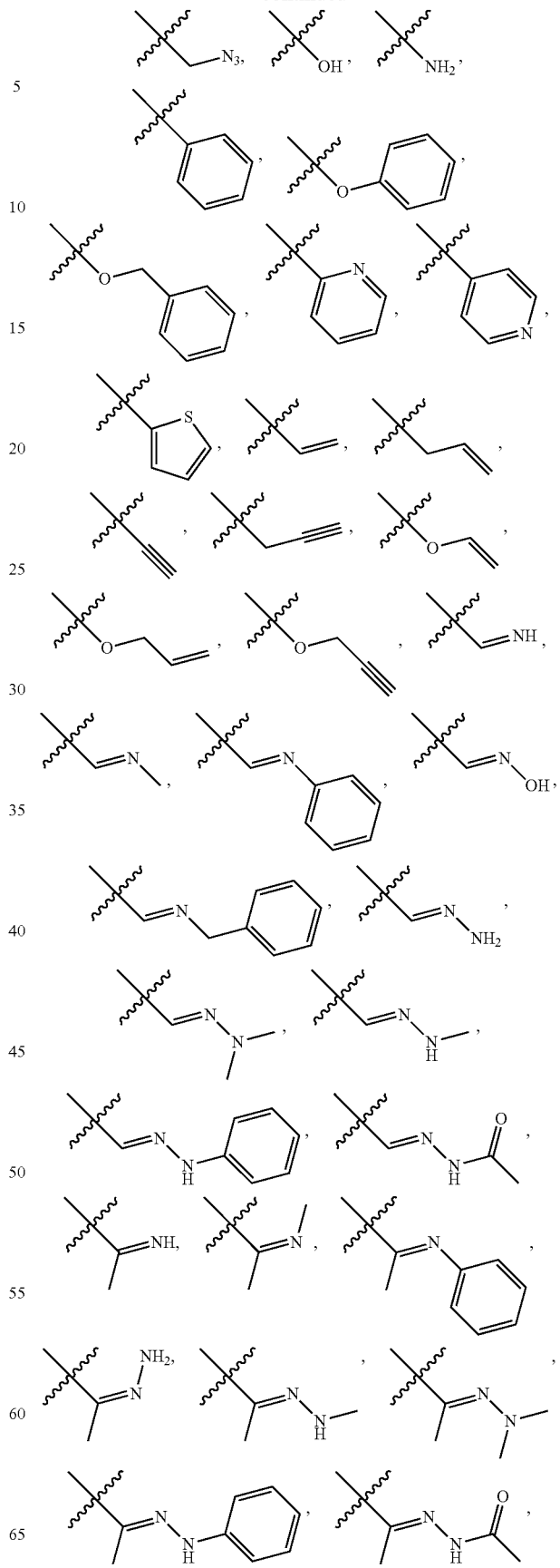

-continued

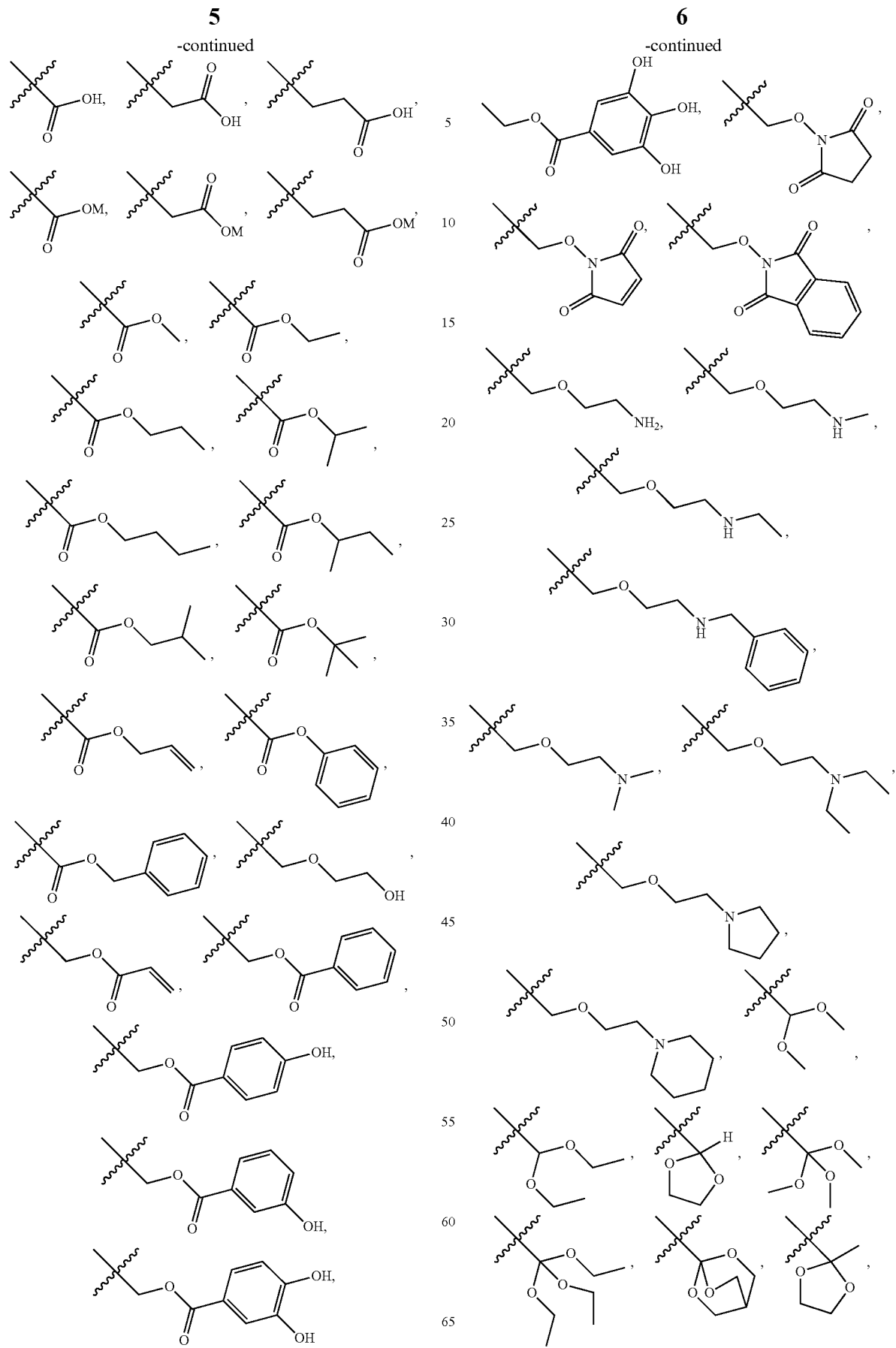

-continued
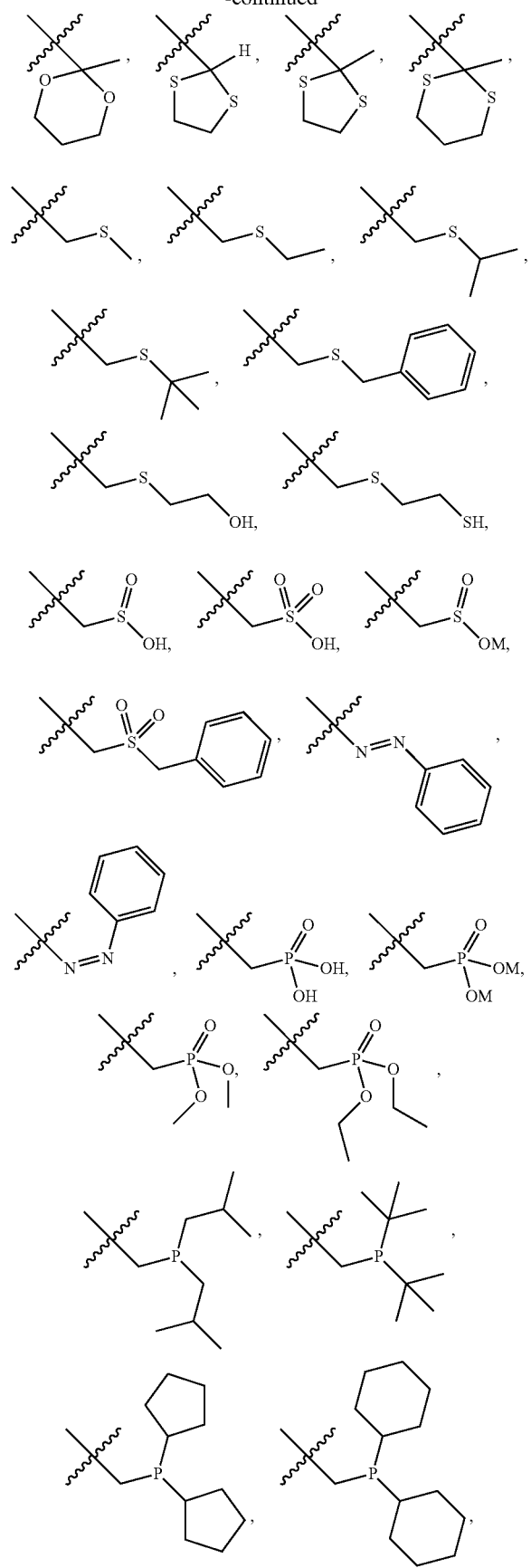
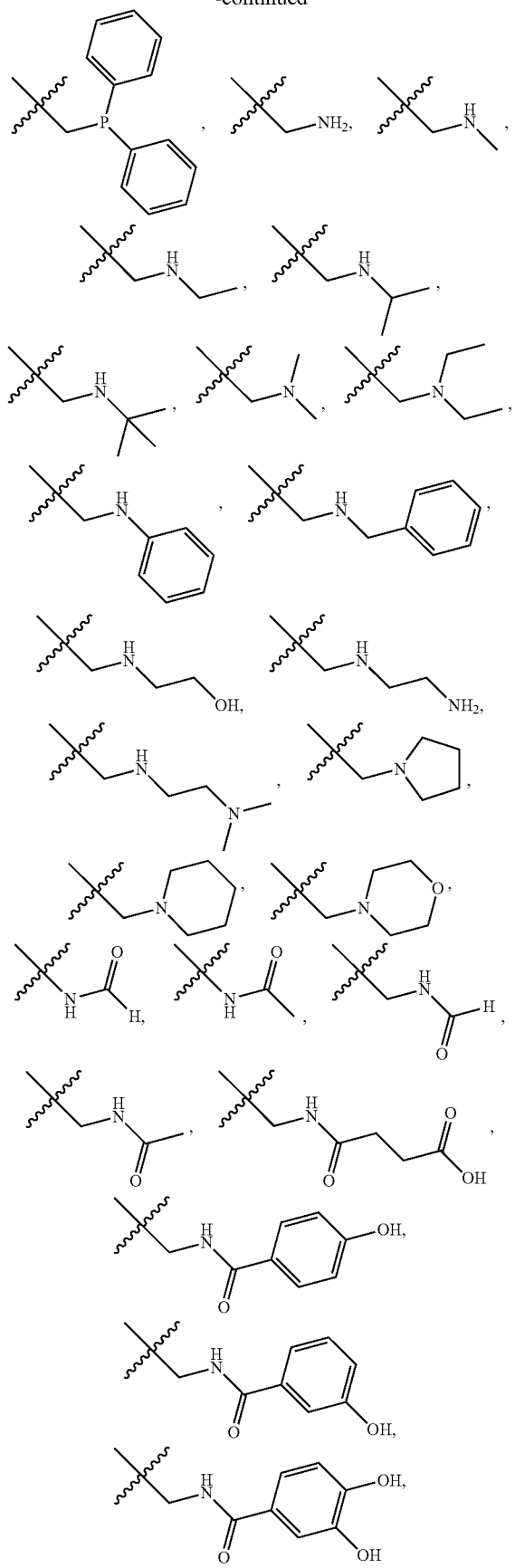

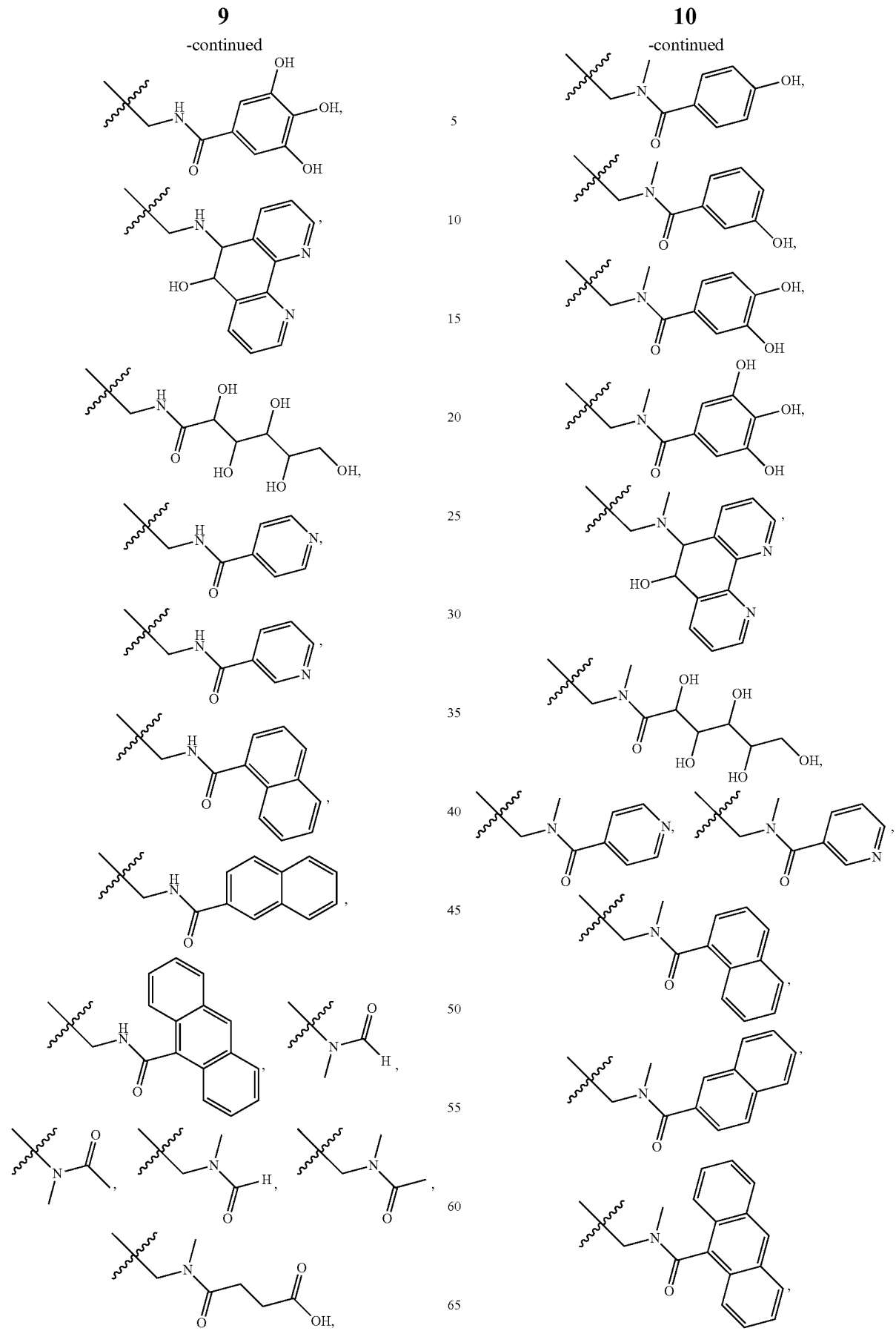

-continued
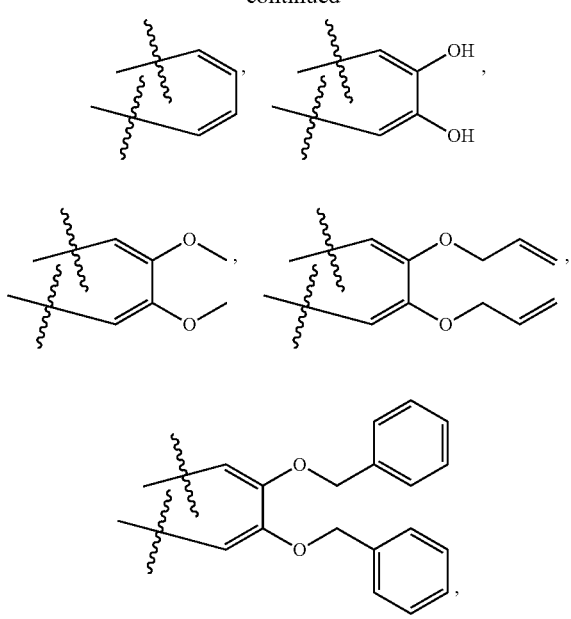
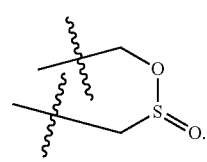
In another embodiment, the plurality of organic linking ligands comprise a least one organic linking ligand having the structure of:
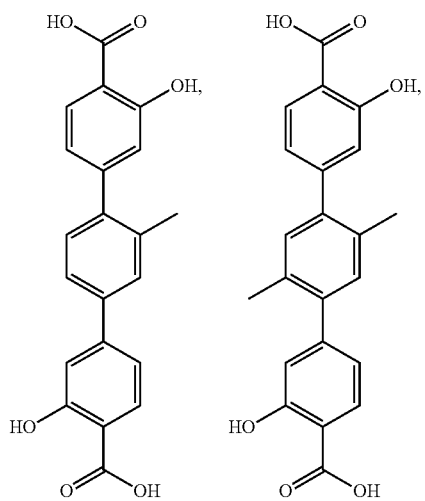
-continued
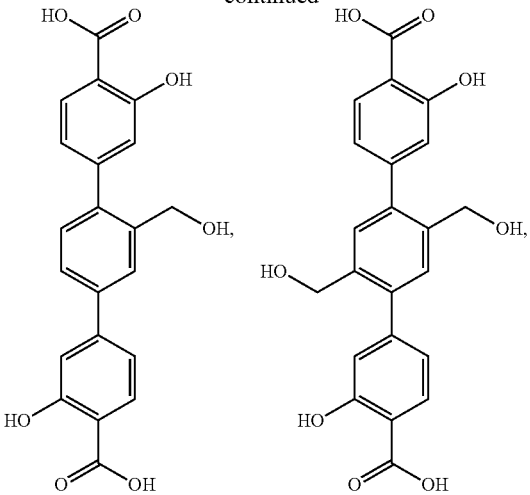
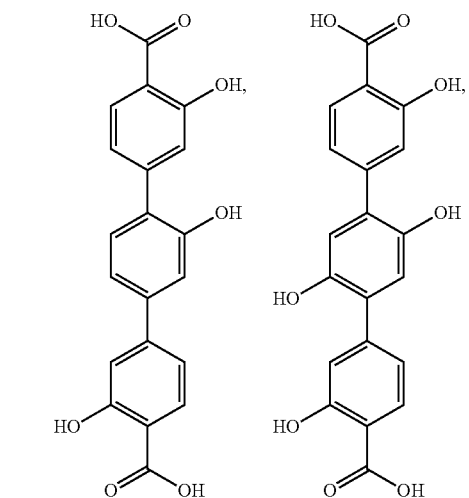
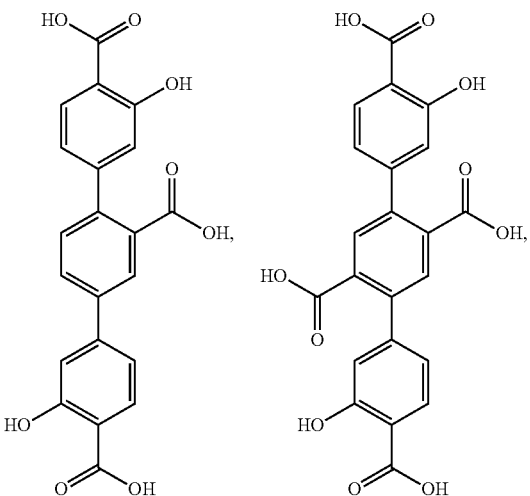

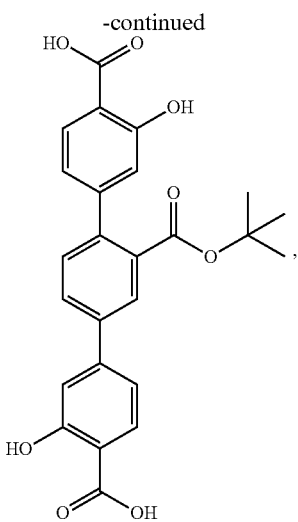

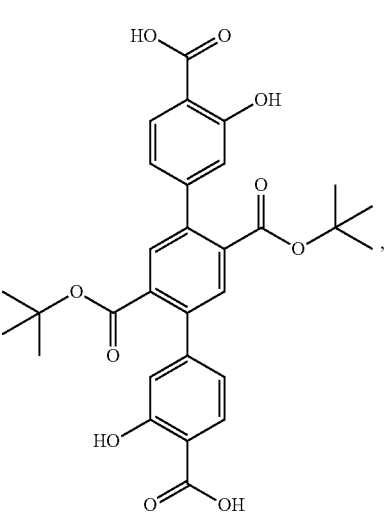

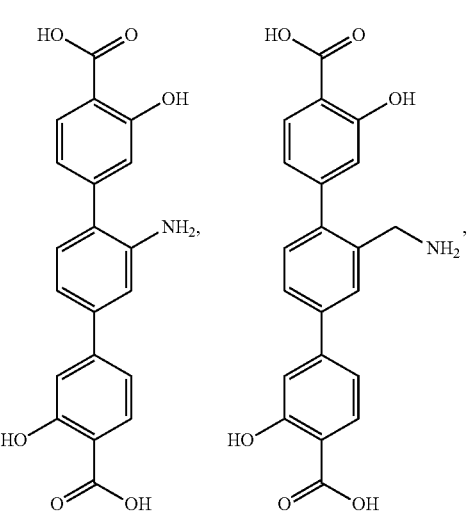

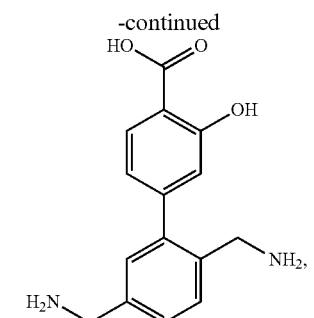

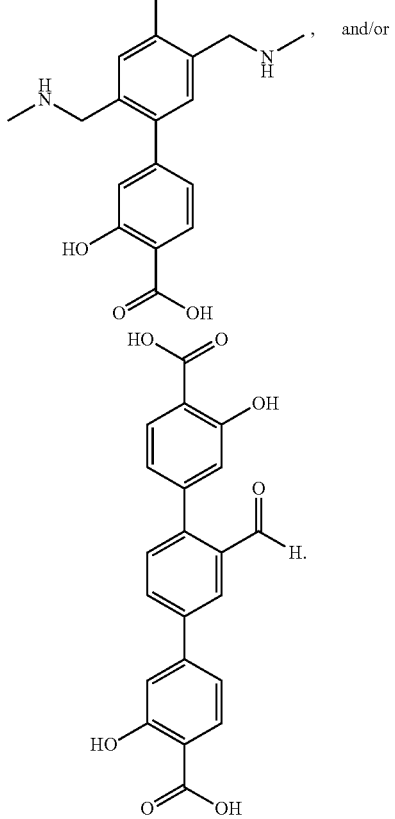

In a certain embodiment, the disclosure further provides that the organic linking ligands which comprise hydroxyl groups may further comprise a hydroxyl protecting group. In another embodiment, the disclosure further provides that the organic linking moieties which comprise amine groups may further comprise an amine protecting group. In a particular embodiment, the amine protecting group is a tert-butyl carbamate (Boc) group. In yet another embodiment, the disclosure further provides that the organic linking moieties which comprise carbonyl groups may further comprise a carbonyl protecting group.

In particular embodiment, the disclosure provides for a MOF comprising a plurality of SBUs that are linked together by a plurality of organic linking ligands, wherein at least two of the SBUs comprise different metals or metal ions and/or wherein at least two of the organic linking ligands comprise a different number or a different type of functional group(s). In a further embodiment, the plurality of SBUs comprise at least two, at least three, or at least three SBUs that differ by being comprised of different metals or metal ions. In a yet further embodiment, the plurality of SBUs comprise one or more metals or metal ions selected from: $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^+$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, $La^+$, and combinations thereof, including any complexes which contain the metals or metal ions, as well as any corresponding metal salt counter-anions. In another embodiment, the plurality of SBUs comprise one or more divalent metal ions selected from: $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $Db^{2+}$, $Tm^{2+}$, $Yb^{2+}$, and $La^{2+}$, including any complexes which contain the metal ions, as well as any corresponding metal salt counter-anions. In yet another embodiment, the plurality of SBUs comprise one or more divalent metal ions selected from: $Mg^{2+}$, $Ca^{2+}$, $Sr^{2+}$, $Mn^{2+}$, $Fe^{2+}$, $Co^{2+}$, $Ni^{2+}$, and $Zn^{2+}$, including any complexes which contain the metal ions, as well as any corresponding metal salt counter-anions. In a particular embodiment, the plurality of SBUs all have the same topology.

In a certain embodiment, the disclosure provides for a MOF that comprises a structure that is similar to or a variant of MOF-74 or IRMOF-74.

In another embodiment, the disclosure also provides for a device comprising a MOF disclosed herein. In a further embodiment, the device is a gas separation and/or gas storage device. In yet a further embodiment, the device is a water storage device.

In a particular embodiment, the disclosure further provides a method of separating one or more gases from a gas mixture comprising contacting the gas mixture with a MOF of the disclosure. In another embodiment, the disclosure provides a method of catalyzing the formation of one or more products from one or more reactants by using a one-pot co-catalyst system that comprises contacting the one or more reactants with a MOF disclosed herein.

DESCRIPTION OF DRAWINGS

FIG. 8A-B presents the results of functionalizing IRMOF-74-III. (A) Presents the structures of functionalized organic links resulting from high-yielding, scalable syntheses. (B) Presents PXRD patterns of seven functionalized IRMOF-74-III derivatives.

FIG. 9 presents the structures of 12 different organic linking moieties that have been synthesized for IRMOF-74-III. Eleven of them formed the target morphology. Further, clean postsynthetic deprotection of Boc-amine moieties was achieved.

DETAILED DESCRIPTION

Figure 1A:
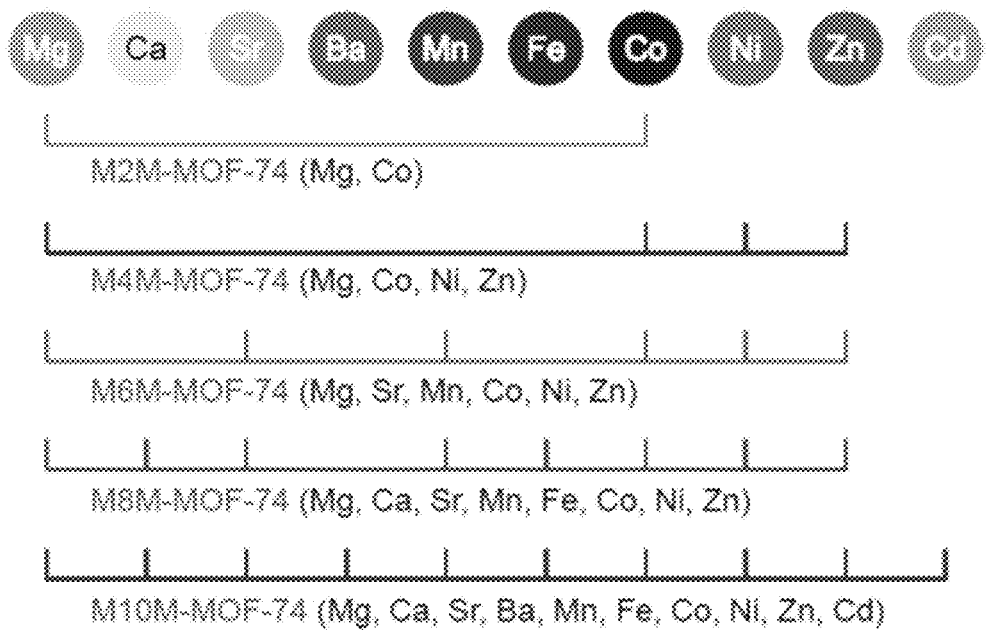
FIG. 1A-C shows mm-MOFs of the disclosure. (A) provides an exemplary scheme for combination of metal ions used to synthesize mm-MOF-74. (B) presents the experimental powder X-ray diffraction pattern (PXRD) for mm-MOF-74's which contains different metal as compared to the calculated MOF-74 PXRD (bottom). A comparison of the peaks shows agreement between the patterns, indicating that the synthesized material has MOF-74 topology. (C) shows the ratio of metals found in three distinct regions of a M10M-MOF-74 sample (inset: SEM image indicating the specific region (1, 2 and 3) in which EDS was collected to quantify the ratio of metals present).
Figure 1B:
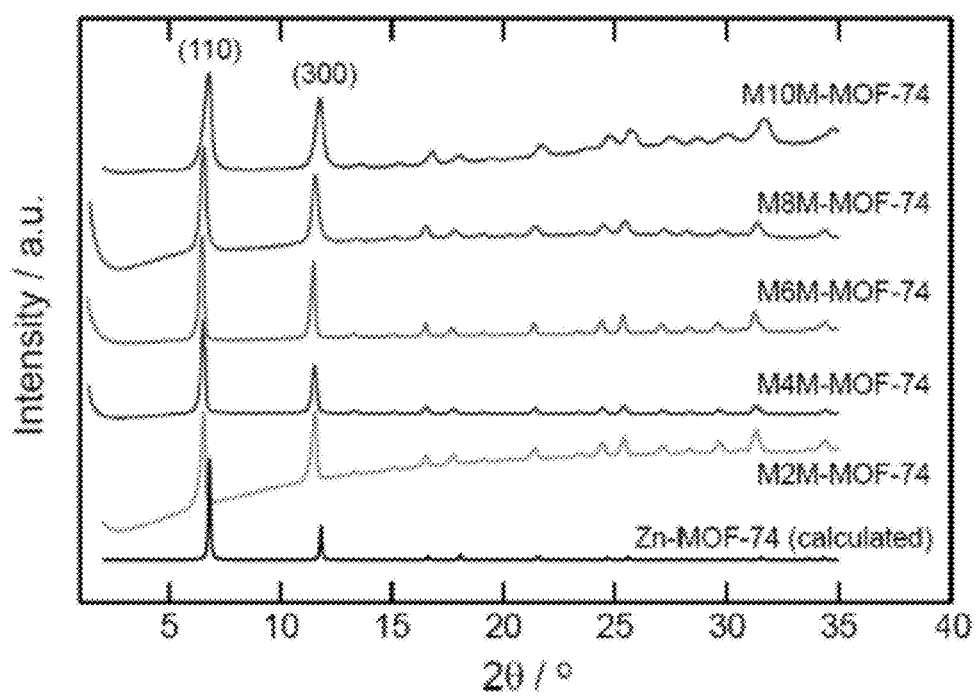
Figure 1C:
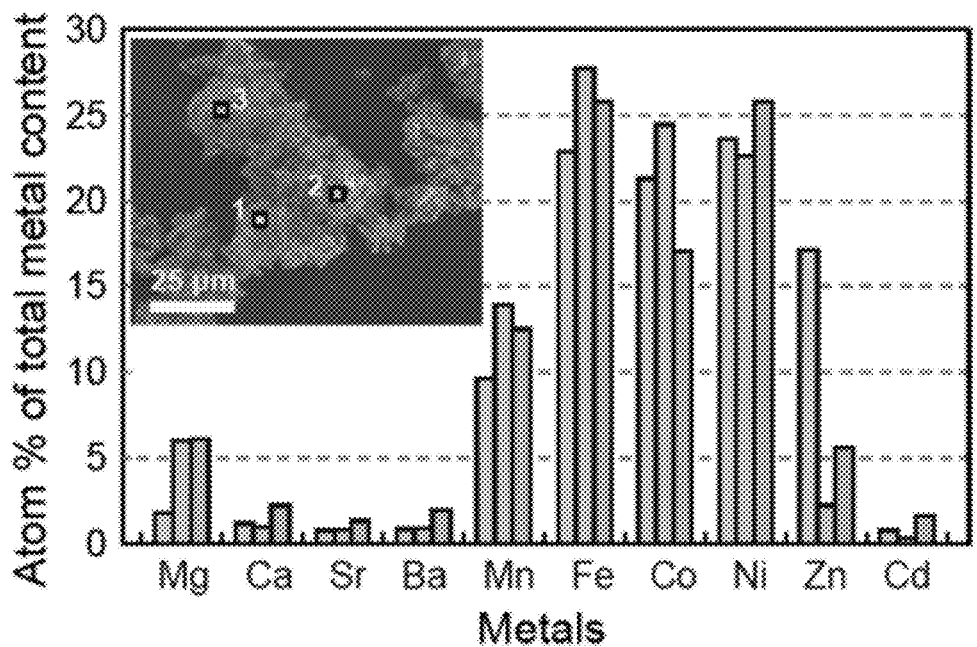
Figure 2:
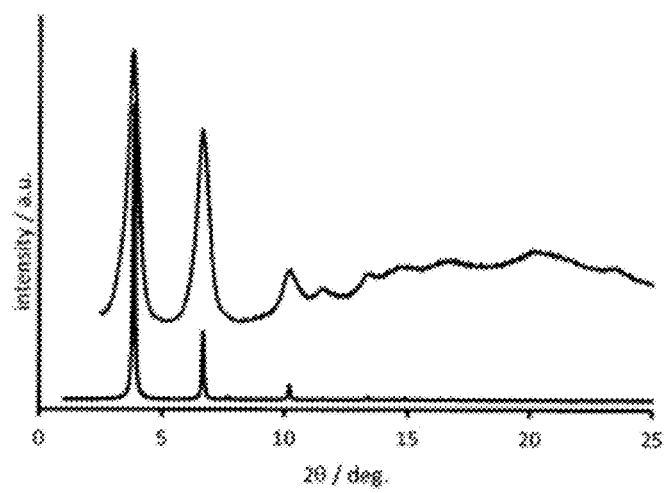
FIG. 2 presents the PXRD pattern of IRMOF-74-III [$(CH_2NHMe)_2$] [$(CH_2OH)_2$] (top) as compared to the calculated pattern for IRMOF-III (bottom). A comparison of the peaks shows agreement between the patterns, indicating that the synthesized material has the MOF-74-III structure.
Figure 3A:
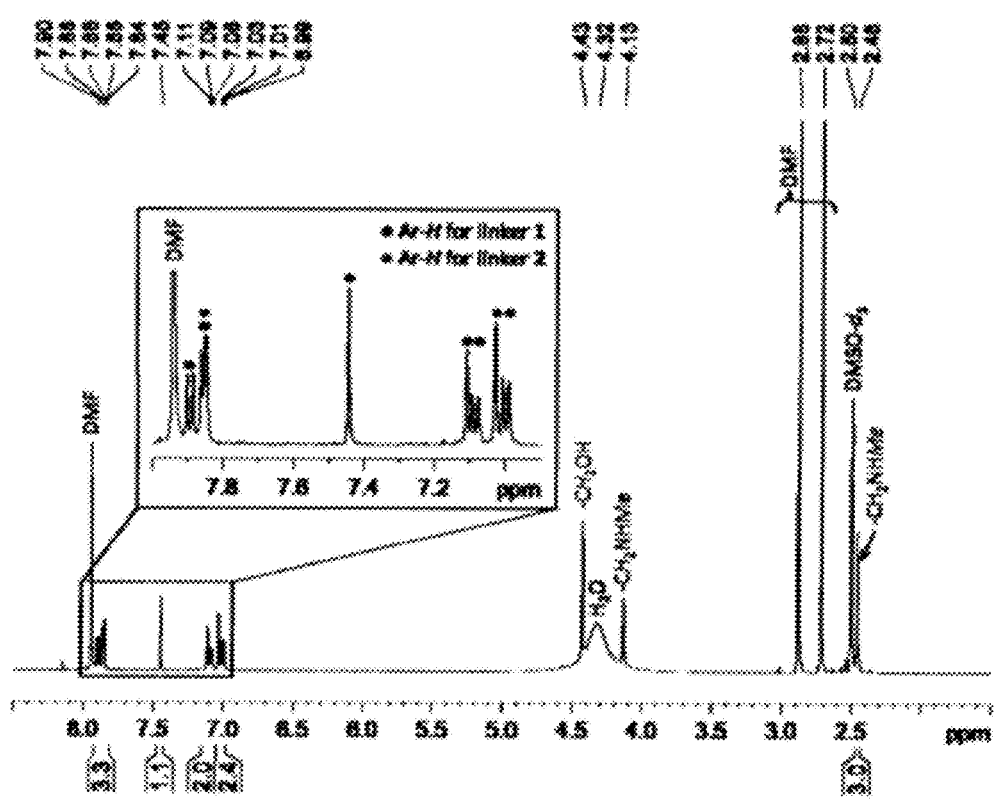
FIG. 3A-B presents (A) an $^1H$ NMR spectrum of a hydrolytically degraded sample of IRMOF-74-III [$(CH_2NHMe)_2$][$(CH_2OH)_2$] at 500 MHz, using DMSO-$d_6$/$D_2O$/DCl. The spectrum shows that the product is comprised of two different linking ligands. (B) Nitrogen adsorption isotherms of a series of MM-MOF-74 measured at 77 K. As a reference, the isotherm of Mg-MOF-74 is overlaid.
Figure 3B:
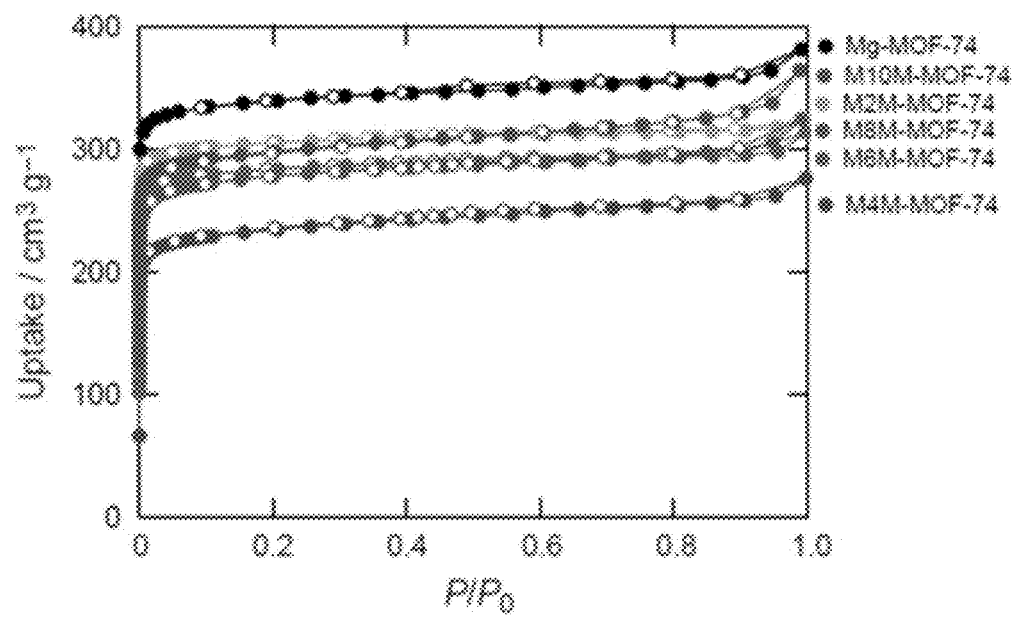

As used herein and in the appended claims, the singular forms "a," "and," and "the" include plural referents unless the context clearly dictates otherwise. Thus, for example, reference to "an organic linking ligand" includes a plurality of such linking ligands and reference to "the metal ion" includes reference to one or more metal ions and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned throughout the disclosure are incorporated herein by reference in full for the purpose of describing and disclosing the methodologies, which might be used in connection with the description herein. Moreover, with respect to similar or identical terms found in the incorporated references and terms expressly defined in this disclosure, the term definitions provided in this disclosure will control in all respects.

Unless defined otherwise, all technical and scientific terms used herein have the same meaning as commonly understood to one of ordinary skill in the art. Although there are many methods and reagents similar or equivalent to those described herein, the exemplary methods and materials are presented herein.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates a bond that may be a single covalent bond or alternatively a double covalent bond. But in the case where an atom's maximum valence would be exceeded by forming a double covalent bond, then the bond would be a single covalent bond.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "cluster" refers to identifiable associations of 2 or more atoms. Such associations are typically established by some type of bond-ionic, covalent, Van der Waal, coordinate and the like.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cylcloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "framework" as used herein, refers to a highly ordered structure comprised of secondary building units (SBUs) that can be linked together in defined, repeated and controllable manner, such that the resulting structure is characterized as being porous, periodic and crystalline. Typically, "frameworks" are two dimensional (2D) or three dimensional (3D) structures. Examples of "frameworks" include, but are not limited to, "metal-organic frameworks" or "MOFs", "zeolitic imidazolate frameworks" or "ZIFs", or "covalent organic frameworks" or "COFs". While MOFs and ZIFs comprise SBUs of metals or metal ions linked together by forming covalent bonds with linking clusters on organic linking moieties, COFs are comprised of SBUs of organic linking moieties that are linked together by forming covalent bonds via linking clusters. "Frameworks" are highly ordered and extended structures that are not based upon a centrally coordinated ion, but involve many repeated secondary building units (SBUs) linked together. Accordingly, "frameworks" are orders of magnitude much larger than coordination complexes and have different structural and chemical properties due to the framework's open and ordered structure.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

The term "heterocycle", as used in this disclosure, refers to ring structures that contain at least 1 noncarbon ring atom. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof.

Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to:

a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydropyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The term "hetero-aryl" used alone or as a suffix or prefix, refers to a heterocycle or heterocyclyl having aromatic character. Examples of heteroaryls include, but are not limited to, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The terms "heterocyclic group", "heterocyclic moiety", "heterocyclic", or "heterocyclo" used alone or as a suffix or prefix, refers to a heterocycle that has had one or more hydrogens removed therefrom.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

A "linking ligand" or "organic linking ligand" refers to a parent chain that binds a metal or metal ion or a plurality of metals or metal ions. A linking moiety may be further substituted post-synthesis by reacting with one or more post-framework reactants.

The term "linking cluster" refers to one or more atoms capable of forming an association, e.g. covalent bond, polar covalent bond, ionic bond, and Van Der Waal interactions, with one or more atoms of another linking moiety, and/or one or more metal or metal ions. A linking cluster can be part of the parent chain itself and/or additionally can arise from functionalizing the parent chain, e.g. adding carboxylic acid groups to the parent chain. For example, a linking cluster can comprise NN(H)N, N(H)NN, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Generally, the linking clusters disclosed herein are Lewis bases, and therefore have lone pair electrons available and/or can be deprotonated to form stronger Lewis bases. The deprotonated version of the linking clusters, therefore, are encompassed by the disclosure and anywhere a linking cluster that is depicted in a non-de-protonated form, the de-protonated form should be presumed to be included, unless stated otherwise.

A "metal" refers to a solid material that is typically hard, shiny, malleable, fusible, and ductile, with good electrical and thermal conductivity. "Metals" used herein refer to metals selected from alkali metals, alkaline earth metals, lanthanides, actinides, transition metals, and post transition metals.

A "metal ion" refers to an ion of a metal. Metal ions are generally Lewis Acids and can form coordination complexes. Typically, the metal ions used for forming a coordination complex in a framework are ions of transition metals.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "post-framework reactants" refers to all known substances that are directly involved in a chemical reaction. Post-framework reactants typically are substances, either elemental or MOF frameworks, which have not reached the optimum number of electrons in their outer valence levels, and/or have not reached the most favorable energetic state due to ring strain, bond length, low bond dissociation energy, and the like. Some examples of post-framework reactants include, but are not limited to:

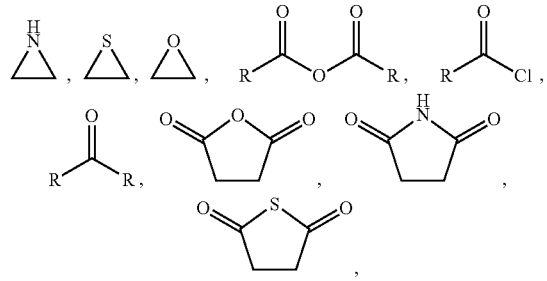

I—R, Br—R, $CR_3$—Mg—Br, $CH_2R$—Li, $CR_3$, Na—R, and K—R; and wherein each R is independently selected from the group comprising: H, sulfonates, tosylates, azides, triflates, ylides, alkyl, aryl, OH, alkoxy, alkenes, alkynes, phenyl and substitutions of the foregoing, sulfur-containing groups (e.g., thioalkoxy, thionyl chloride), silicon-containing groups, nitrogen-containing groups (e.g., amides and amines), oxygen-containing groups (e.g., ketones, carbonates, aldehydes, esters, ethers, and anhydrides), halogen, nitro, nitrile, nitrate, nitroso, amino, cyano, ureas, boron-containing groups (e.g., sodium borohydride, and catecholborane), phosphorus-containing groups (e.g., phosphorous tribromide), and aluminum-containing groups (e.g., lithium aluminum hydride).

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "unsubstituted" with respect to hydrocarbons, heterocycles, and the like, refers to structures wherein the parent chain contains no substituents.

Metal-organic frameworks (MOFs) are porous crystalline materials that are constructed by linking metal clusters called Secondary Building Units (SBUs) and organic linking moieties. The pore environment in MOFs depends on the nature and combination of those building units; thus, the property and function of MOFs can be varied by employing different building units to gain optimal performance for each intended application. However, while the high structural tunability and diversity are distinguishing characteristics of MOFs, it is highly challenging to synthesize a MOF in which the SBUs are linked by multiple types of differently functionalized organic linking ligands and/or where the SBUs are comprised of different metal atoms.

The disclosure provides for MOFs that comprise a plurality of different types of organic linking moieties, and/or a plurality of different types of SBUs. In a particular embodiment, the disclosure further provides that the MOFs of the disclosure comprise SBUs which are linked by functionalized organic linking ligands. In some embodiments, the MOF comprises two or more types of differently functionalized linking ligands. In another embodiment, the disclosure provides that the MOFs of the disclosure comprise organic linking moieties which are linked to two or more SBUs that comprise different metal, metal ions or metal clusters. In yet another embodiment, the disclosure provides for MOFs comprising SBUs which are linked by two or more types of differently functionalized organic linking ligands, wherein the different types of functional groups on different organic linking moieties modify the chemical and physical properties of a MOF disclosed herein. In a further embodiment, the MOFs of the disclosure comprise organic linking moieties which are linked to two or more SBUs that comprise different metal or metal ion atoms, and comprise SBUs which are linked by a functionalized linking ligand or wherein the SUBs are linked by two or more types of differently functionalized organic linking ligands. The MOFs of the disclosure are multivariate in that the material properties can be readily modified by changing the ratio between multiple types of metal ions in SBUs or the type or ratio between multiple types of differently functionalized organic linking ligands. In a certain embodiment, a MOF of the disclosure is multivariate in that the material properties of the MOF can be readily modified by changing the ratio between multiple types of metals or metal ions in the SBUs or the type, or ratio between multiple types, of differently functionalized organic linking ligands. Accordingly, the MOF is topologically uniform, but is not uniform in terms of the metal composition of the SBUs or the structure of the organic linking ligands. The structural tunability of the MOFs disclosed herein exceeds that of previously known systems, allowing for an extremely high level of optimization for various applications such as gas separation, gas storage, water storage and release, or catalysis.

The disclosure provides compositions and methods of making mixed-metal MOFs (mm-MOFs). The mm-MOFs of the disclosure can be generally characterized as having the formula:

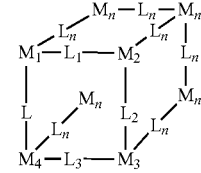

wherein at least two of $M_1$-$M_n$ (wherein n is greater than 2) comprise different metals, metal ions or metal clusters and wherein L-$L_n$ are the same or are different (e.g., multivariate). In a specific embodiment, the disclosure provides a MOF wherein the MOF comprises different metals, metal ions and/or metal clusters and the same linking ligand. In another embodiment, the disclosure provides a MOF wherein the metals, metal ions or metal clusters are the same but the linking ligands in the MOF are variant. Although the general structure above is depicted as being cuboidal, the actual geometry of the MOF will depend upon the metal and linking ligands used and of course the respective bond angles.

In one embodiment, $M_1$-$M_n$ comprise 2 different metal, metal ions or metal clusters. In a further embodiment the 2 different metal are selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, OS, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{3+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, $La^+$, including any complexes which contain the metals or metal ions listed above, as well as any corresponding metal salt counter-anions. In a particular embodiment, the metals are comprised of different types of divalent metal ions or divalent metal ion complexes. Examples of divalent metal ions include $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^+$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $Db^{2+}$, $Tm^{2+}$, $Yb^{2+}$, and $La^{2+}$, including any complexes which contain the metals or metal ions listed above, as well as any corresponding metal salt counter-anions. In a further embodiment, the 2 metal are selected from the group consisting of Mg, Ca, Sr, Ba, Mn, Fe, Co, Ni, Zn, and Cd. In a further embodiment, of any of the foregoing embodiment, the linking ligand comprise a structure of Formula I and/or II:

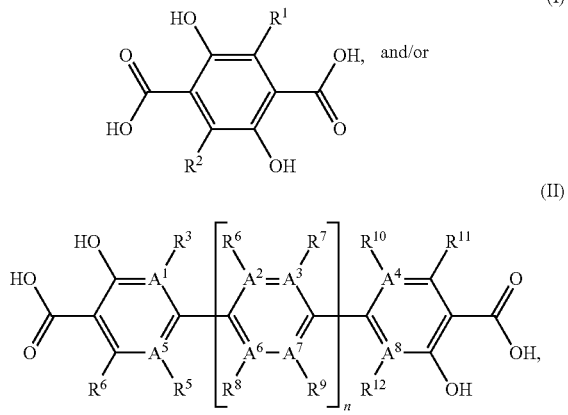

wherein, n is a number from 0 to 10;

$A^1$-$A^8$ are independently a C or N;

$R^1$-$R^{12}$ are independently selected from H, D, FG, optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, optionally substituted ($C_1$-$C_{12}$)cycloalkyl, optionally substituted ($C_1$-$C_{12}$)cycloalkenyl, optionally substituted aryl, optionally substituted heterocycle, optionally substituted mixed ring system, —C($R^{13}$)$_3$, —CH($R^{13}$)$_2$, —CH$_2R^{13}$, —C($R^{14}$)$_3$, —CH($R^{14}$)$_2$, —CH$_2R^{14}$, —OC($R^{13}$)$_3$, OCH($R^{13}$)$_2$, —OCH$_2R^{13}$, —OC($R^{14}$)$_3$, —OCH($R^{14}$)$_2$, OCH$_2R^{14}$, wherein $R^4$-$R^{11}$ when adjacent can be linked together to form one or more substituted rings selected from the group comprising cycloalkyl, cycloalkenyl, heterocycle, aryl, and mixed ring system;

$R^{13}$ is selected from FG, optionally substituted ($C_1$-$C_{12}$) alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, hemiacetal, hemiketal, acetal, ketal, and orthoester; and $R^{14}$ is selected from one or more substituted or unsubstituted rings selected from cycloalkyl, aryl and heterocycle.

In one embodiment, $M_1$-$M_n$ comprise 4 different metal, metal ions or metal clusters. In a further embodiment the 4 different metal are selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^+$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^+$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, $La^+$, including any complexes which contain the metals or metal ions listed above, as well as any corresponding metal salt counter-anions. In a particular embodiment, the metals are comprised of different types of divalent metal ions or divalent metal ion complexes. Examples of divalent metal ions include $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $Db^{2+}$, $Tm^{2+}$, $Yb^{2+}$, and $La^{2+}$, including any complexes which contain the metals or metal ions listed above, as well as any corresponding metal salt counter-anions. In a further embodiment, the 4 metal are selected from the group consisting of Mg, Ca, Sr, Ba, Mn, Fe, Co, Ni, Zn, and Cd. In a further embodiment, of any of the foregoing embodiment, the linking ligand comprise a structure of Formula I and/or II as set forth above.

In one embodiment, $M_1$-$M_n$ comprise 6 different metal, metal ions or metal clusters. In a further embodiment the 6 different metal are selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, OS, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^+$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^+$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, $La^+$, including any complexes which contain the metals or metal ions listed above, as well as any corresponding metal salt counter-anions. In a particular embodiment, the metals are comprised of different types of divalent metal ions or divalent metal ion complexes. Examples of divalent metal ions include $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $Db^{2+}$, $Tm^{2+}$, $Yb^{2+}$, and $La^{2+}$, including any complexes which contain the metals or metal ions listed above, as well as any corresponding metal salt counter-anions. In a further embodiment, the 6 metal are selected from the group consisting of Mg, Ca, Sr, Ba, Mn, Fe, Co, Ni, Zn, and Cd. In a further embodiment, of any of the foregoing embodiment, the linking ligand comprise a structure of Formula I and/or II.

In one embodiment, $M_1$-$M_n$ comprise 8 different metal, metal ions or metal clusters. In a further embodiment the 8 different metal are selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, $La^+$, including any complexes which contain the metals or metal ions listed above, as well as any corresponding metal salt counter-anions. In a particular embodiment, the metals are comprised of different types of divalent metal ions or divalent metal ion complexes. Examples of divalent metal ions include $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $Db^{2+}$, $Tm^{2+}$, $Yb^{2+}$, and $La^{2+}$, including any complexes which contain the metals or metal ions listed above, as well as any corresponding metal salt counter-anions. In a further embodiment, the 8 metal are selected from the group consisting of Mg, Ca, Sr, Ba, Mn, Fe, Co, Ni, Zn, and Cd. In a further embodiment, of any of the foregoing embodiment, the linking ligand comprise a structure of Formula I and/or II.

In one embodiment, $M_1$-$M_n$ comprise 10 or more different metal, metal ions or metal clusters. In a further embodiment the 10 or more different metal are selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, $La^+$, including any complexes which contain the metals or metal ions listed above, as well as any corresponding metal salt counter-anions. In a particular embodiment, the metals are comprised of different types of divalent metal ions or divalent metal ion complexes. Examples of divalent metal ions include $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $Db^{2+}$, $Tm^{2+}$, $Yb^{2+}$, and $La^{2+}$, including any complexes which contain the metals or metal ions listed above, as well as any corresponding metal salt counter-anions. In a further embodiment, the 10 metal are selected from the group consisting of Mg, Ca, Sr, Ba, Mn, Fe, Co, Ni, Zn, and Cd. In a further embodiment, of any of the foregoing embodiment, the linking ligand comprise a structure of Formula I and/or II.

The disclosure exemplifies, but is not limited to, a plurality of mm-MOFs based upon MOF-74. For example, the disclosure demonstrates the synthesis of five isostructural, single-phase MOF-74 structures having 2 (Mg and Co; "M2M-"), 4 (Mg, Co, Ni and ZN; "M4M-"), 6 (Mg, Sr, Mn, Co, Ni and Zn; "M6M-"), 8 (Mg, CA SR, Mn, Fe, Co, Ni and Zn; "M8M-") and 10 (Mg, Ca, Sr, Ba, Mn, Fe, Co, Ni, Zn, and Cd; "M10M-") divalent metals (see, e.g., FIG. 1A).

In one embodiment, an mm-MOF using a linking ligand of Formula I and/or II comprising 10 different metals comprises ratios of metals as follows: Mg, 1.00; Ca, 0.08±0.02; Sr, 0.11±0.01; Ba, 0.28±0.04; Mn, 0.87±0.06; Fe, 1.57±0.34; Co, 1.01±0.11; Ni, 1.05±0.04; Zn, 0.74±0.04; Cd, 0.73±0.09. In a specific embodiment, the disclosure provides a mm-MOF having the empirical formula of $Mg_{0.269}Ca_{0.022}Sr_{0.030}Ba_{0.075}Mn_{0.234}Fe_{0.422}Co_{0.272}Ni_{0.282}Zn_{0.199}Cd_{0.196}(DOT) \cdot (H_2O)_{7-8}$. It is to be noted that the final molar ratio of the metal ions is affected by many factors, such as the reactivity, solubility, and coordination sphere of the metal ions and the pH of the reaction mixture. Table 1 provides example of metal ratios of exemplary mm-MOF-74 crystals.

TABLE 1

Ratio of metals found for mm-MOF-74 crystals. The ratios for each metal in all samples were normalized to value of 1.0 for the metal Mg.

| MOF | Mg | Ca | Sr | Ba | Ma | Fe | Co | Ni | Za | Cd |
|---|---|---|---|---|---|---|---|---|---|---|
| M2M-MOF-74 | 1.0 | n/a | n/a | n/a | n/a | n/a | 3.20 ± 0.38 | n/a | n/a | n/a |
| M4M-MOF-74 | 1.0 | n/a | n/a | n/a | n/a | n/a | 2.46 ± 0.48 | 2.30 ± 0.42 | 2.62 ± 0.44 | n/a |
| M6M-MOF-74 | 1.0 | n/a | 0.05 ± 0.02 | n/a | 1.62 ± 0.06 | n/a | 4.11 ± 0.40 | 3.97 ± 0.20 | 3.57 ± 0.49 | n/a |
| M8M-MOF-74 | 1.0 | 0.10 ± 0.03 | 0.16 ± 0.04 | n/a | 0.92 ± 0.07 | 1.07 ± 0.13 | 1.40 ± 0.25 | 1.38 ± −0.18 | 0.94 ± 0.07 | n/a |
| M10M-MOF-74 | 1.0 | 0.08 ± 0.02 | 0.11 ± 0.01 | 0.28 ± 0.04 | 0.87 ± 0.06 | 1.57 ± 0.34 | 1.01 ± 0.11 | 1.05 ± 0.04 | 0.74 ± 0.04 | 0.73 ± 0.09 |

(n/a = not applicable)

Table 2 provides porosity data of the exemplary mm-MOF-74 crystals of the disclosure.

TABLE 2

| MOF | Metal ions | Formula weight$^a$ | BET SA (m$^2$/g) | Langmuir SA (m$^2$/g) |
| --- | --- | --- | --- | --- |
| M2M-MOF-74 | Mg, Co | 297.1 | 1200 | 1310 |
| M4M-MOF-74 | Mg, Co, Ni, Zn | 309.4 | 900 | 1040 |
| M6M-MOF-74 | Mg, Sr, Mn, Co, Ni, Zn | 310.3 | 1100 | 1240 |
| M8M-MOF-74 | Mg, Ca, Sr, Mn, Fe, Co, Ni, Zn | 303.0 | 1070 | 1210 |
| M10M-MOF-74 | Mg, Ca, Sr, Ba, Mn, Fe, Co, Ni, Zn, Cd | 318.5 | 1140 | 1280 |
| Mg-MOF-74 | Mg | 242.7 | 1350 | 1490 |

The mm-MOFs were characterized by PXRD, inductively coupled plasma optical emission and energy-dispersive X-ray spectroscopies (ICP-OES and EDS), scanning electron microscopy (SEM) and N$_2$ adsorption measurements. The results demonstrate that mm-MOFs (e.g., mm-MOF-74) of varying metal composition containing up to 10 different metal ions, is obtained through a one-pot solvothermal reaction with good reproducibility and that his approach can be employed to incorporate metal ions (e.g., CA, Sr, Ba and Cd).

The disclosure also provides methods of making mm-MOFs of the disclosure. The method comprises a solvothermal reaction of a mixture comprising a desired linking ligand and a plurality of different metal salts dissolved in a solvent mixture comprising a polar aprotic solvent and heating the mixture to 70-150° C. for 10-48 hours. In a specific embodiment, the mixture comprises DMF. In a further embodiment, the mixture comprises DMF, ethanol and water. In a further embodiment, the mixture is heated to about 120° C. for 20-24 hours. The resulting crystal can be isolated, washed, purified and dried as desired.

In particular embodiments, the disclosure provides for MOFs that can be tuned to adsorb a specific gas or multiple gases from mixed gas stream or liquid. For example, a MOF disclosed herein that is comprised of multiple different types of SBUs can provide open metal sites from different metals that have differential binding/interaction characteristics for specific gas molecules. These MOFs can be further modified by manipulating the type of linking ligand and the linking ligand's characteristics. For example, a MOF disclosed herein that is comprised of specifically functionalized linking ligands or comprises multiple types of organic linking ligands can provide functional groups that have differential binding/interaction characteristics for specific gas molecules.

Alternatively, a MOF disclosed herein comprising a single type of SBU (i.e., homogenous metals) that is comprised of specifically functionalized linking ligands or comprises multiple types of organic linking ligands can provide functional groups that have differential binding/interaction characteristics for specific gas molecules. Moreover, a MOF disclosed herein can be comprised of both multiple different types of SBUs and multiple types of organic linking moieties so as to facilitate the adsorption of specific gas molecules from a gas mixture, including separating and/or storing gas molecules that are highly similar.

Figure 4:
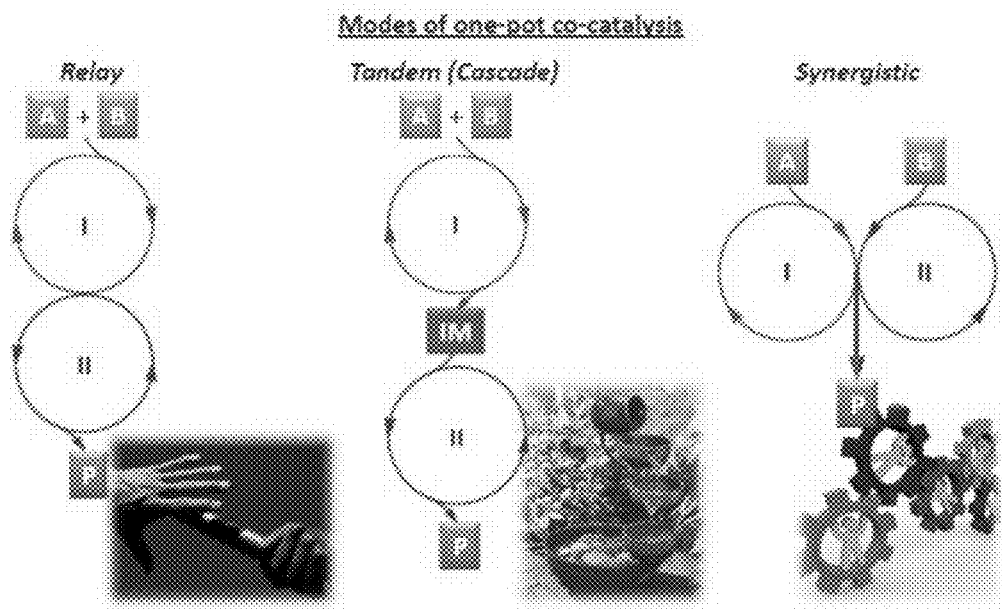
FIG. 4 presents that the multi-functional MOFs disclosed herein can be utilized as a one-pot co-catalyst system.
Figure 5:
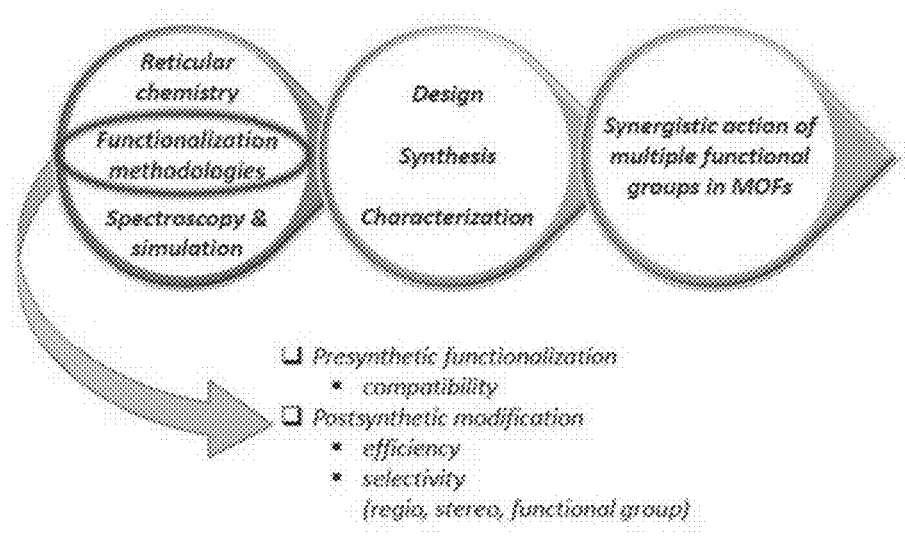
FIG. 5 presents a scheme for the development of multi-functional MOFs for multifaceted applications.
Figure 6:
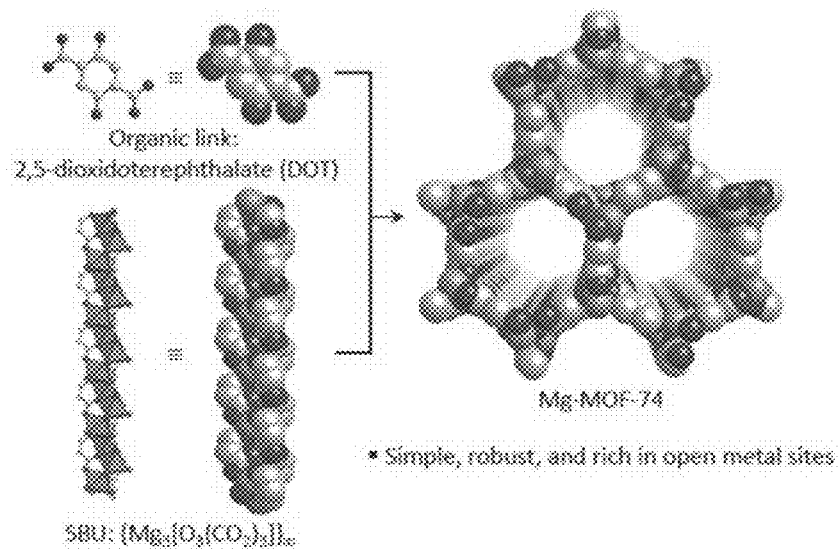
FIG. 6 presents the components of the Mg-MOF-74 framework.

In a certain embodiment, a MOF disclosed herein can be optimized to be a one-pot co-catalyst system which utilizes relay, tandem or synergistic catalytic cycles (e.g., see FIG. 4) by providing organic moieties that comprise different catalytic functional groups and/or different catalytic metal or metallated sites.

It should be understood that for the MOFs disclosed herein which comprise multiple types of differently functionalized organic linking ligands can originate from (1) organic linking ligands that are differentially functionalized presynthesis (i.e., constructing the framework with organic linking ligands that differ by the number and/or type of functional groups); (2) organic linking ligands that comprise functional groups that are modified post-synthesis of the framework by reacting the functional group with a post-framework reactant; (3) organic linking ligands that comprise functional group(s) that are protected with a suitable protecting group which can then be removed post-synthesis of the framework, wherein the de-protected functional groups may be modified by reacting with a post-framework reactant; and (4) organic linking ligands that comprise functional groups which are protected with one type of protecting group while other functional groups are protected with a different type of protecting group, such that the protecting groups can be differentially removed post-synthesis of the framework by using different reaction conditions. Using such a strategy, one can selectively de-protect certain functional groups while leaving other functional groups protected, so that the newly de-protected groups may be modified by reacting with a post-framework reactant. The remaining protected functional groups may then be de-protected and be modified if so desired by reacting with a post-framework reactant, etc.

The disclosure provides for MOFs which are comprised of a plurality of secondary building units (SBUs) that are linked together by a plurality of organic linking ligands, wherein at least two of the SBUs comprise different metals or metal ions and/or wherein at least two of the organic linking ligands comprise a different number and/or different type of functional group. In a particular embodiment, the MOF is comprised of at least two SBUs which comprise different metal or metal ions (i.e., a multi-metal MOF). The metals or metal ions modify the chemical and physical properties of the MOF. The multi-metal MOFs of the disclosure are multivariate in that the material properties can be readily modified by changing the ratio between multiple types of metals or metal ions in SBUs. The multi-metal MOFs of the disclosure while they are not uniform in terms of the composition of the SBUs, can be designed so that they are generally uniform in topology.

In a certain embodiment, a MOF of the disclosure comprises a plurality of SBUs, wherein at least 2, 3, 4, 5, 6, 7, 8, 9, 10 or more of the SBUs differ by being comprised of different metals or metal ions.

In a further embodiment, a MOF of the disclosure comprise a plurality of SBUs, wherein at least 2, 3, 4, 5, 6, 7, or 8 of the SBUs differ by being comprised of different types of divalent metal ions selected from the group consisting of Mg$^{2+}$, Ca$^{2+}$, Sr$^{2+}$, Mn$^{2+}$, Fe$^{2+}$, Co$^{2+}$, Ni$^{2+}$, and Zn$^{2+}$, including any complexes which contain the metal ions listed, as well as any corresponding metal salt counter-anions.

In a particular embodiment, the disclosure provides for MOFs that comprise a plurality SBUs that are linked together by a plurality of organic linking ligands that are comprised of substituted (C$_1$-C$_{20}$) alkyls, substituted (C$_1$-C$_{20}$) alkenyls, substituted (C$_1$-C$_{20}$) alkynyls, optionally substituted (C$_1$-C$_{20}$) hetero-alkyls, optionally substituted (C$_1$-C$_{20}$) hetero-alkenyls, optionally substituted (C$_1$-C$_{20}$) hetero-alkynyls, substituted (C$_3$-C$_{12}$) cycloalkyls, substituted (C$_3$-C$_{12}$) cycloalkenyls, substituted aryls, optionally substituted heterocycles or optionally substituted mixed ring systems; wherein the organic linking ligands comprise functional groups that can form bond(s) with one or more SBUs; and wherein the linking ligand has been functionalized or wherein at least two of the organic linking ligands comprise different numbers or different types of functional groups.

In a particular embodiment, the disclosure provides for MOFs that comprise a plurality SBUs that are linked together by a plurality of organic linking ligands that comprise a structure of Formula I and/or II:

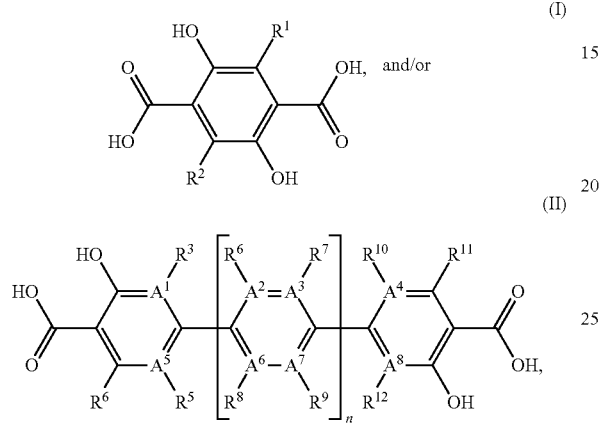

wherein,
n is a number from 0 to 10;
$A^1$-$A^8$ are independently a C or N;
$R^1$-$R^{12}$ are independently selected from H, D, functional group (FG), optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, optionally substituted ($C_1$-$C_{12}$)cycloalkyl, optionally substituted ($C_1$-$C_{12}$)cycloalkenyl, optionally substituted aryl, optionally substituted heterocycle, optionally substituted mixed ring system, —C($R^{13}$)$_3$, —CH($R^{13}$)$_2$, —CH$_2$$R^{13}$, —C($R^{14}$)$_3$, —CH($R^{14}$)$_2$, —CH$_2$$R^{14}$, —OC($R^{13}$)$_3$, OCH($R^{13}$)$_2$, —OCH$_2$$R^{13}$, —OC($R^{14}$)$_3$, —OCH($R^{14}$)$_2$, OCH$_2$$R^{14}$, wherein $R^4$-$R^{11}$ when adjacent can be linked together to form one or more optionally substituted rings selected from the group comprising cycloalkyl, cycloalkenyl, heterocycle, aryl, and mixed ring system; $R^{13}$ is selected from FG, optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, hemiacetal, hemiketal, acetal, ketal, and orthoester; and $R^{14}$ is selected from one or more substituted or unsubstituted rings selected from cycloalkyl, aryl and heterocycle;

wherein, in some embodiments, the MOF comprises two or more organic linking ligands which comprise different functional groups, and/or wherein the MOF comprises two or more SBUs that comprise different metals, metal ions, or metal containing complexes.

In another embodiment, the disclosure provides for MOFs that comprise a plurality SBUs that are linked together by a plurality of organic linking ligands that comprise a structure of Formula III:

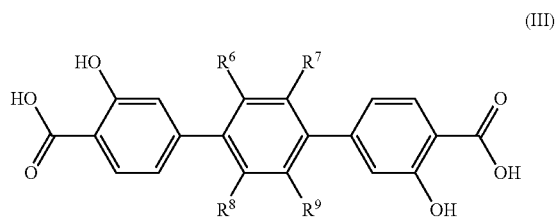

wherein,
$R^6$-$R^9$ are independently selected from:

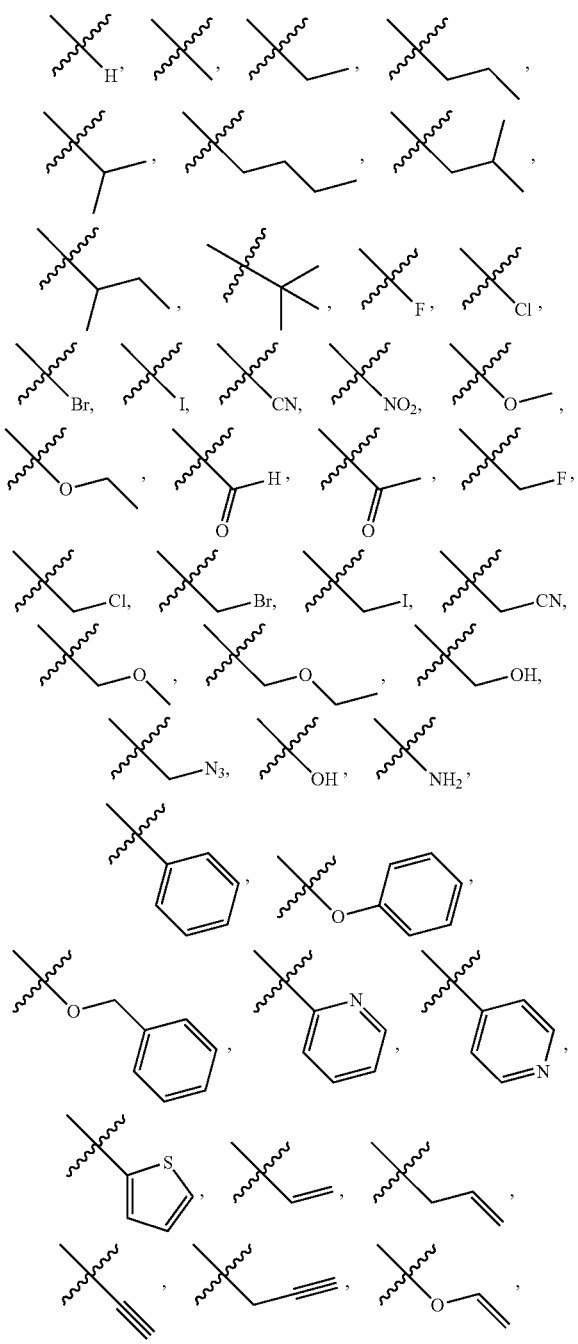

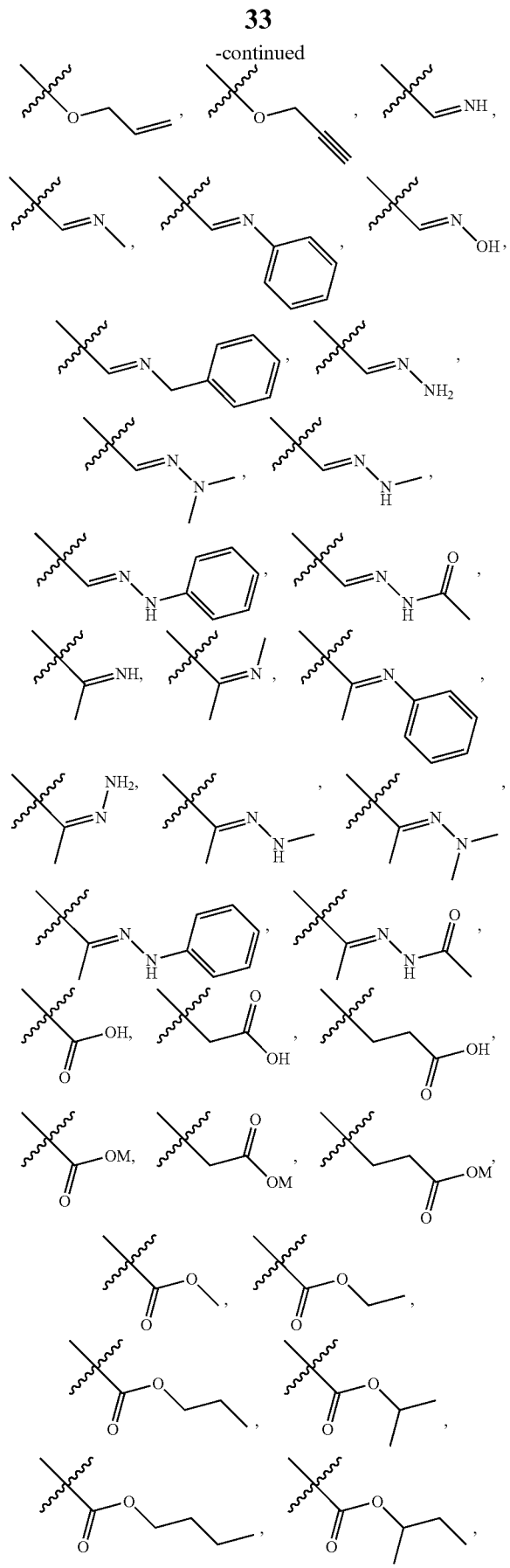
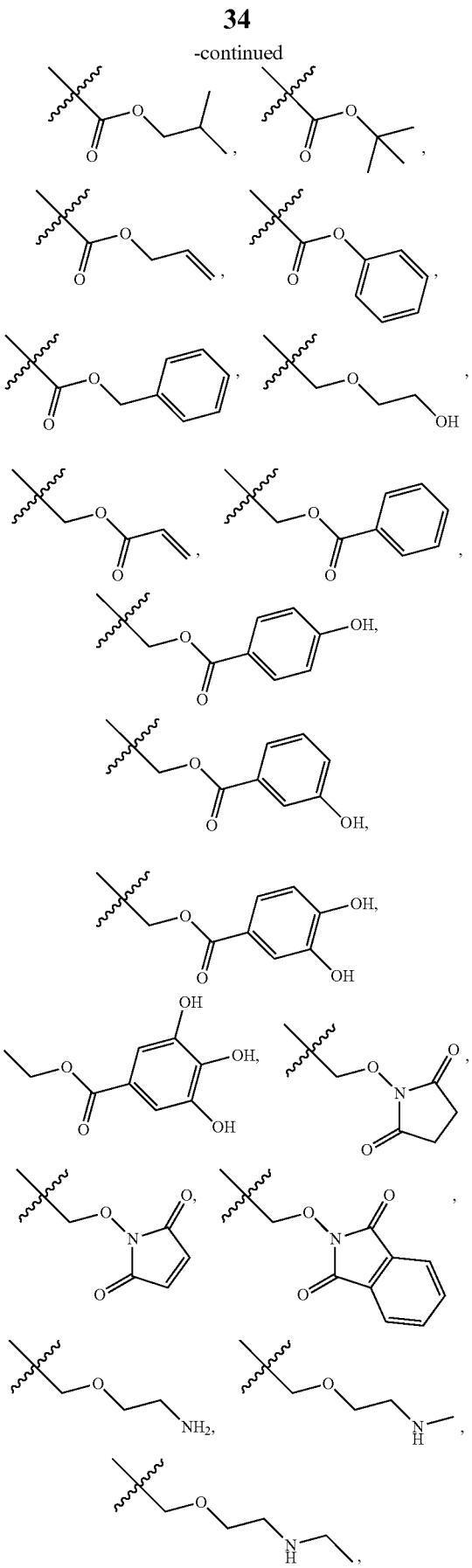

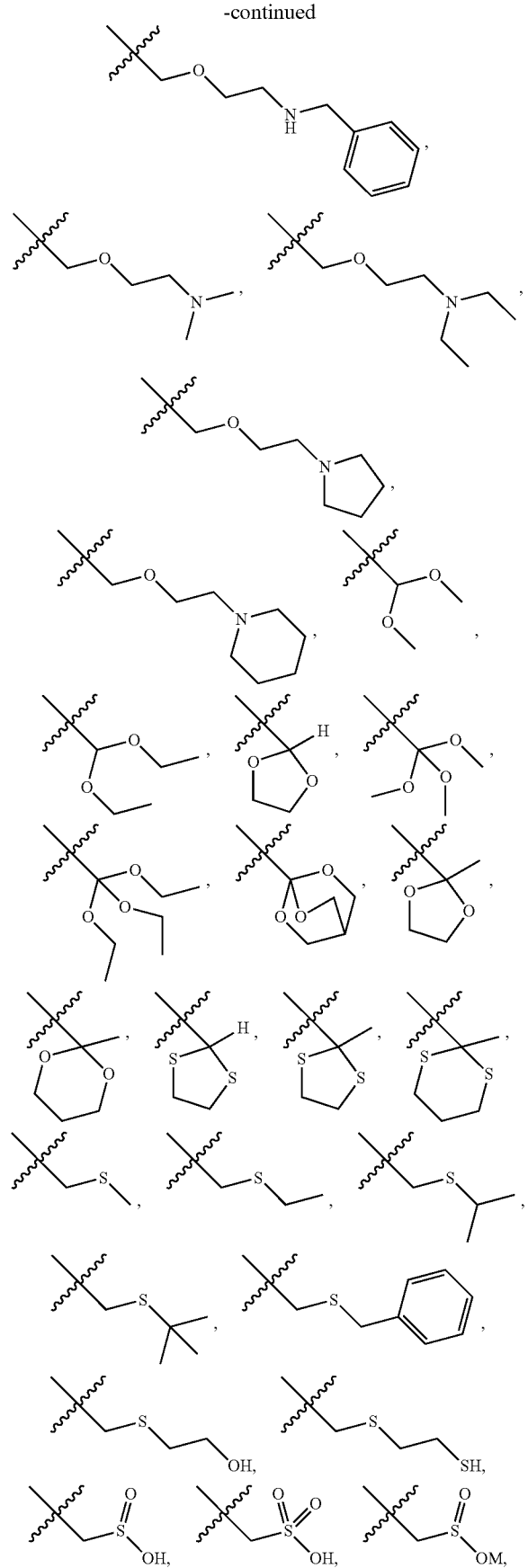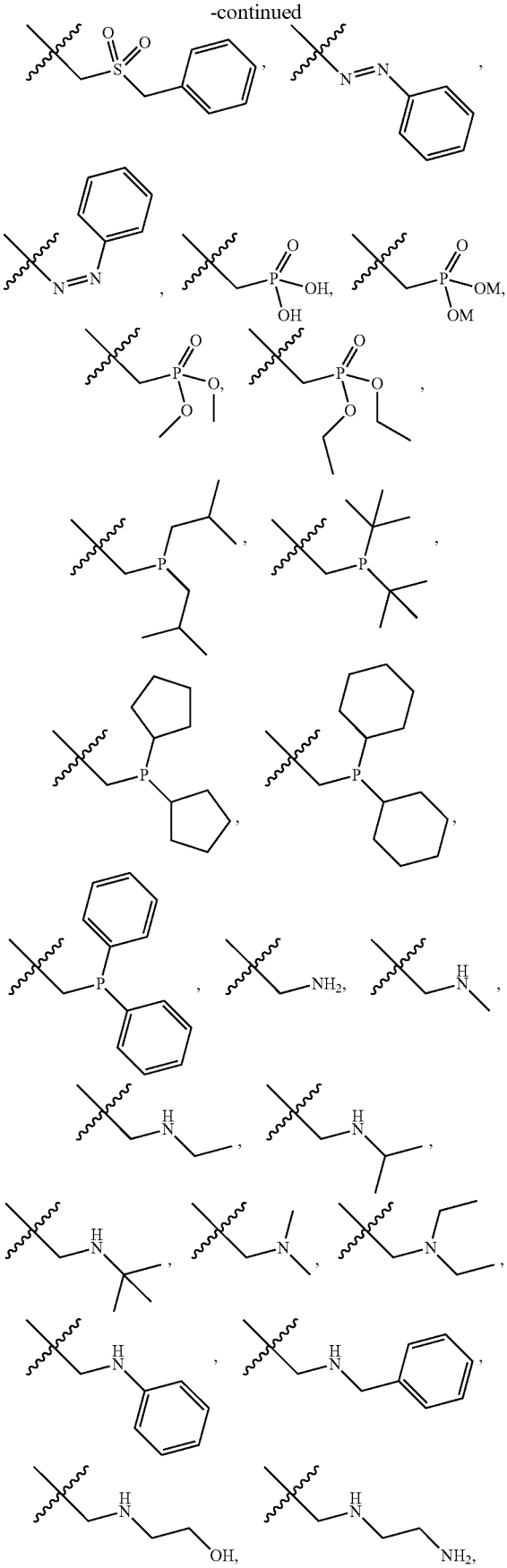

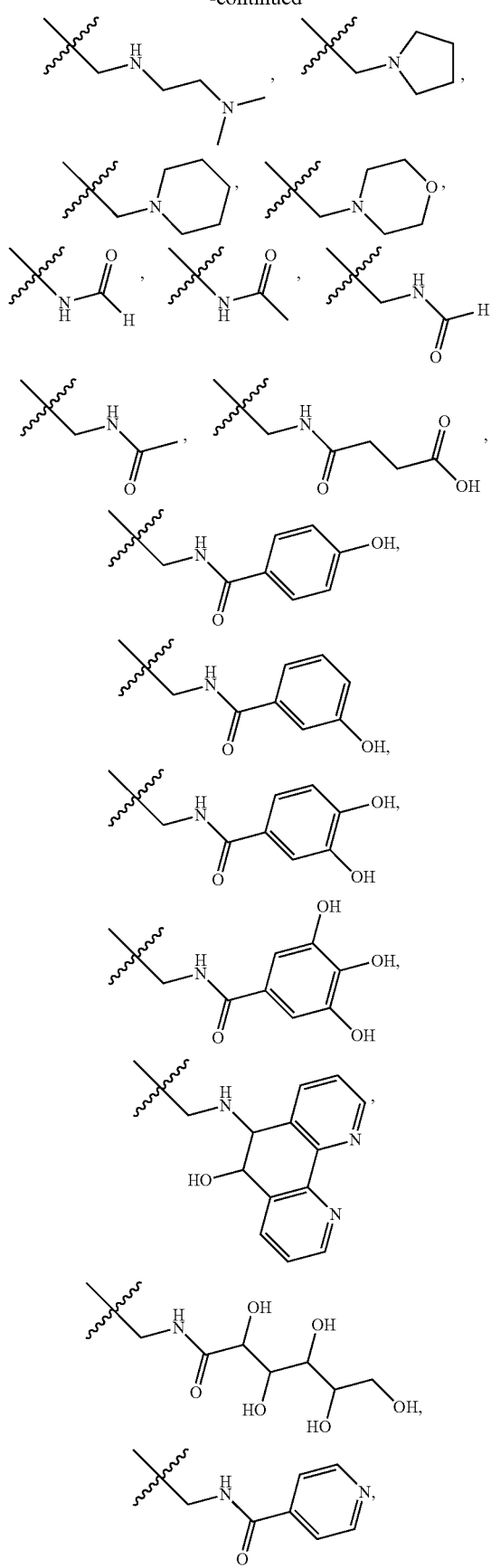
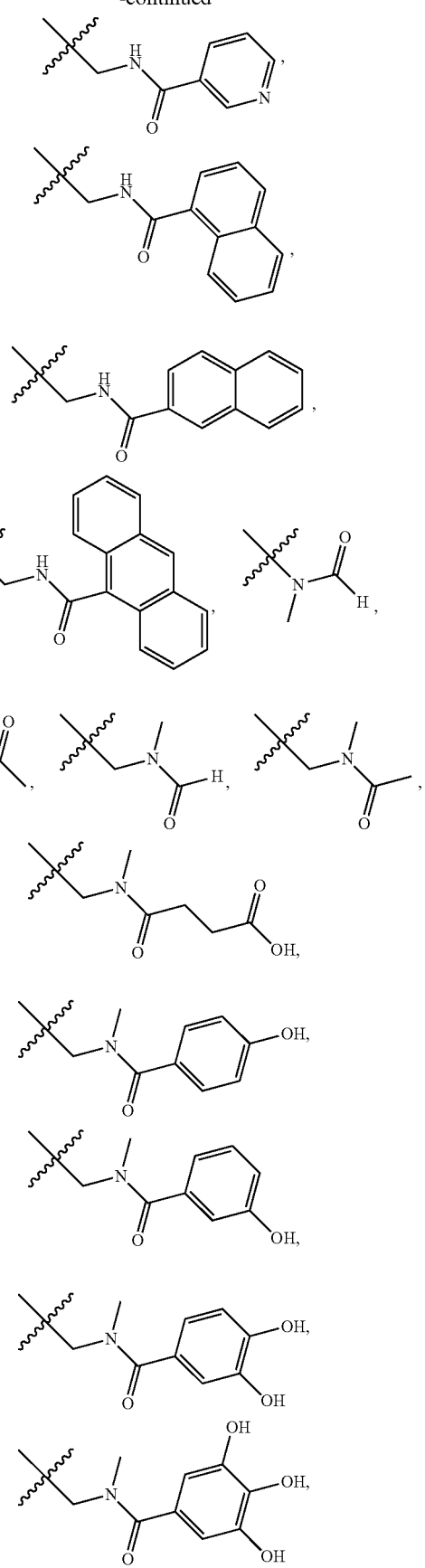

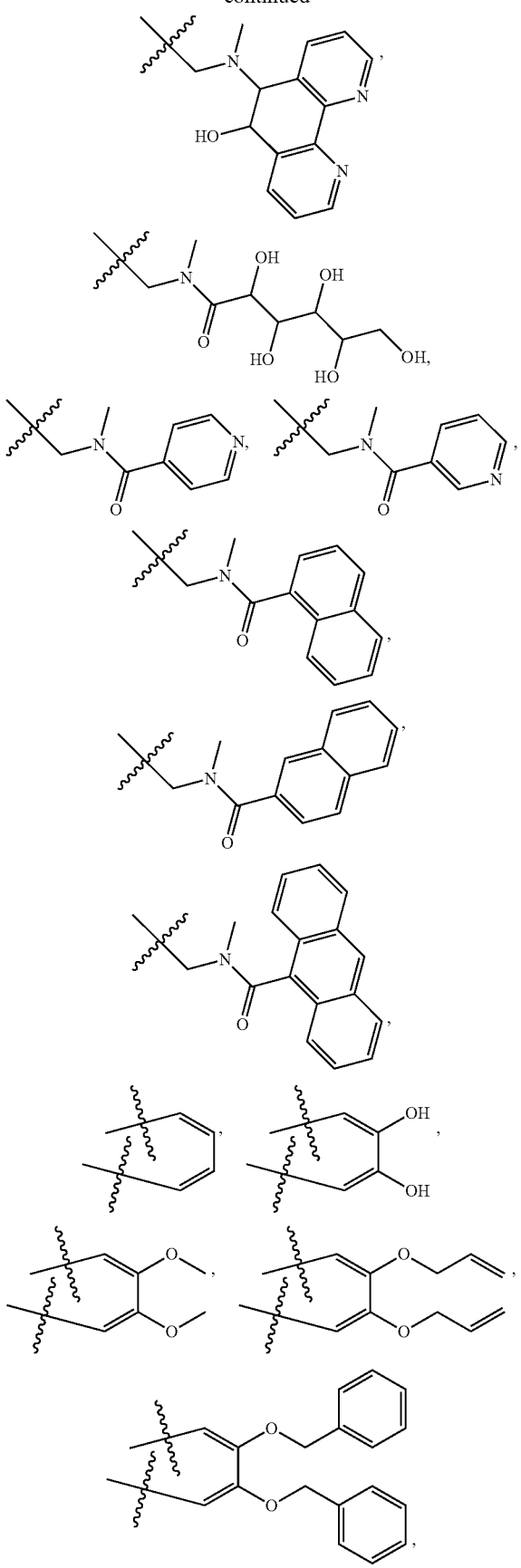

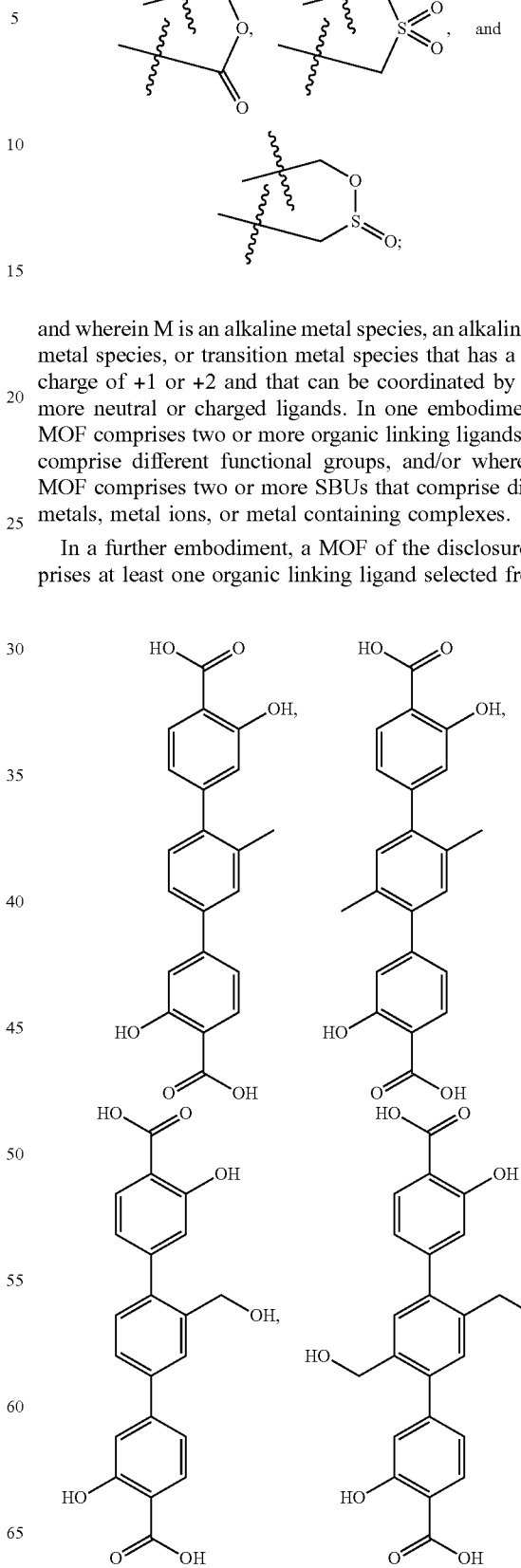

and wherein M is an alkaline metal species, an alkaline-earth metal species, or transition metal species that has a formal charge of +1 or +2 and that can be coordinated by one or more neutral or charged ligands. In one embodiment, the MOF comprises two or more organic linking ligands which comprise different functional groups, and/or wherein the MOF comprises two or more SBUs that comprise different metals, metal ions, or metal containing complexes.

In a further embodiment, a MOF of the disclosure comprises at least one organic linking ligand selected from:

-continued
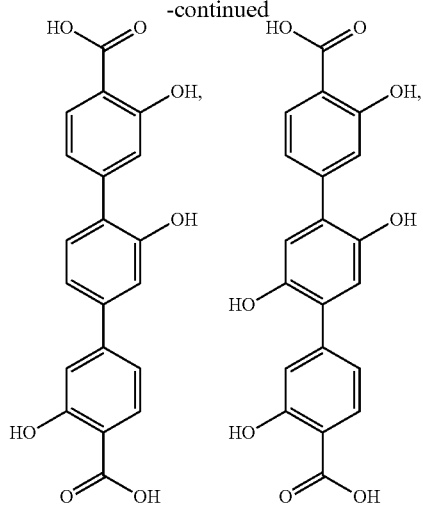
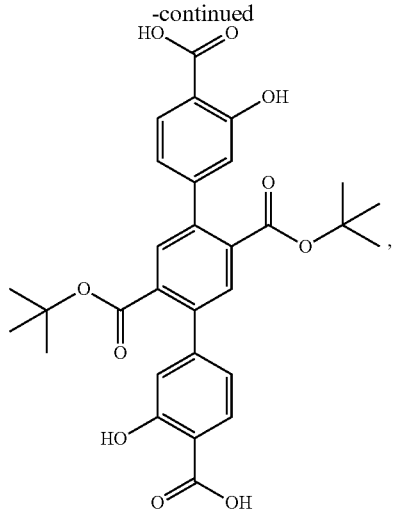
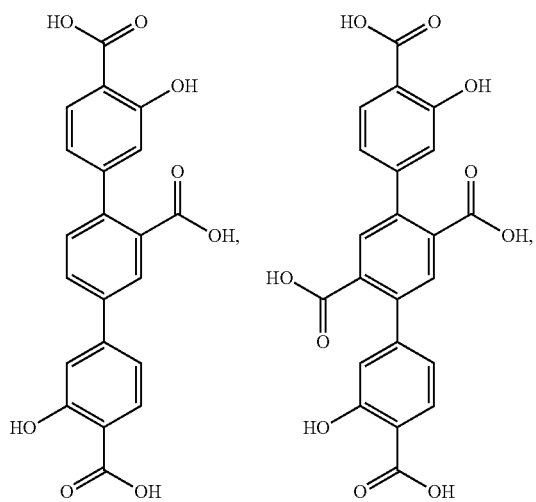
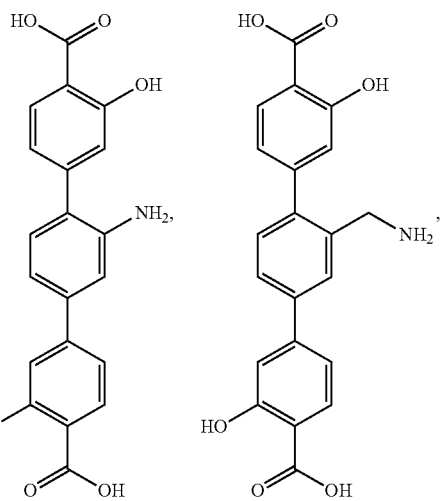
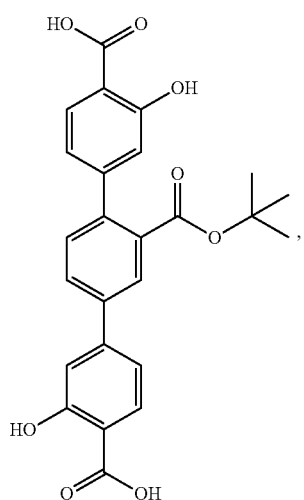
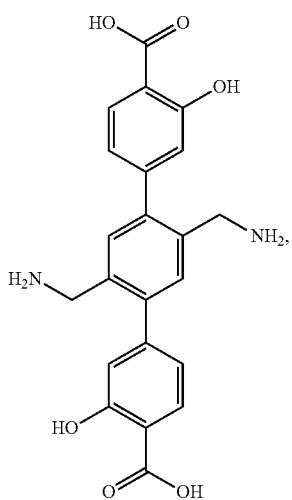

-continued

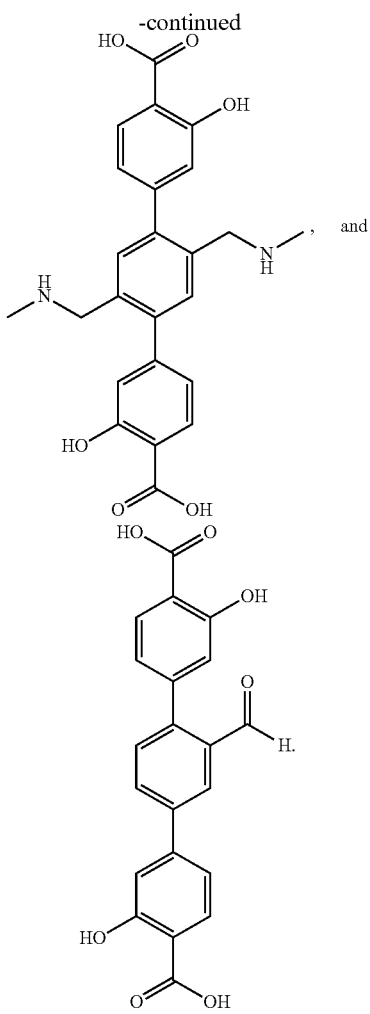

Figure 7A:
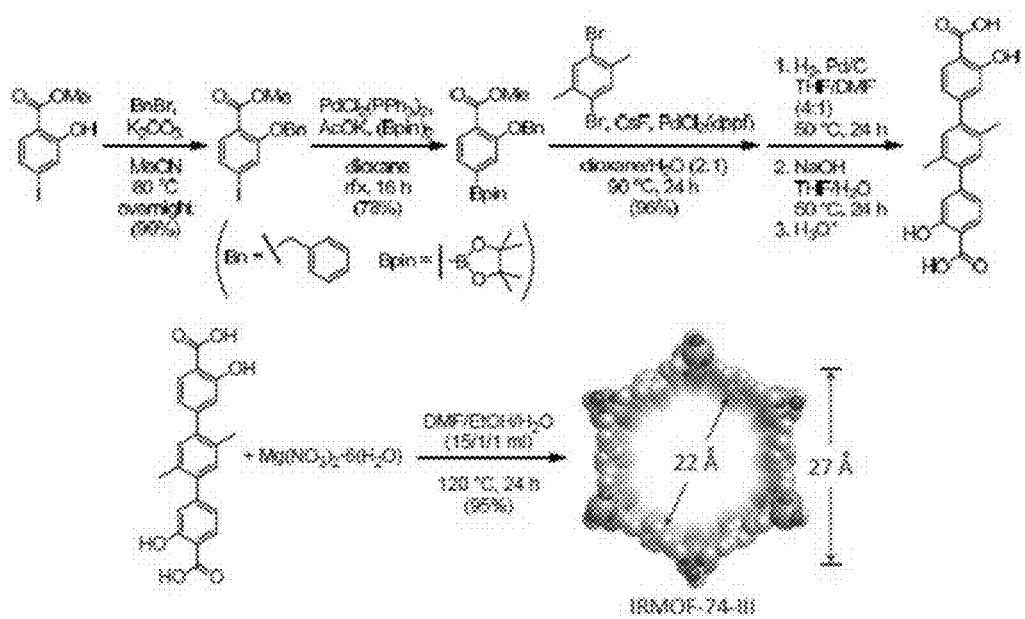
FIG. 7A-B provides (A) a reaction scheme for the synthesis of IRMOF-74-III. (B) Synthetic pathway for the functionalized organic linkers used in the synthesis of IRMOF-74-III. This methodology allowed us to prepare —$CH_3$ (5a), —$NH_2$, (5b), —$CH_2NHBoc$ (5c), and —$CH_2NMeBoc$ (5d) functionalized linkers. On the right is shown a schematic representation of the IRMOF-74-III pore as functionalized with the organic linkers 5a-5d and post-synthetic deprotection of Boc groups.

The disclosure exemplifies the modifications of the pores by showing how the interior of porous MOFs can be designed to overcome the complications presented by the competition of water with $CO_2$. The disclosure exemplifies this using a MOF constructed from magnesium oxide rods joined by terphenylene organic linkers (IRMOF-74-III, $Mg_2$ ($DH_3PhDC$), where $H_4DH_3PhDC$=2',5'-dimethyl-3,3''-dihydroxy-[1,1':4',1''-terphenyl]-4,4''-dicarboxylic acid, FIG. 7A-B) to make an extended structure with an etb topology supporting one-dimensional channels of 25 Å in their diagonal.

Figure 7B:
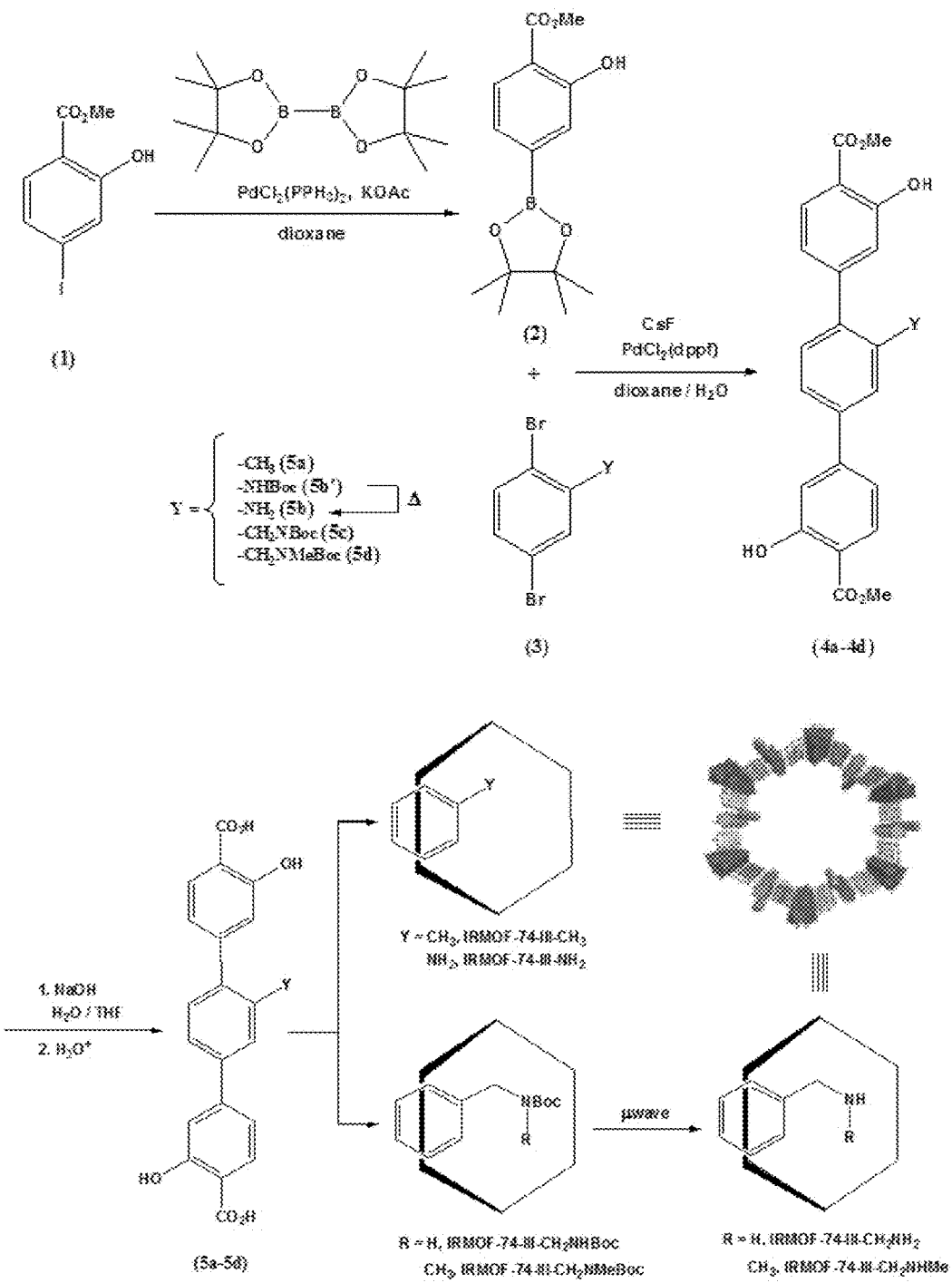
Figure 10:
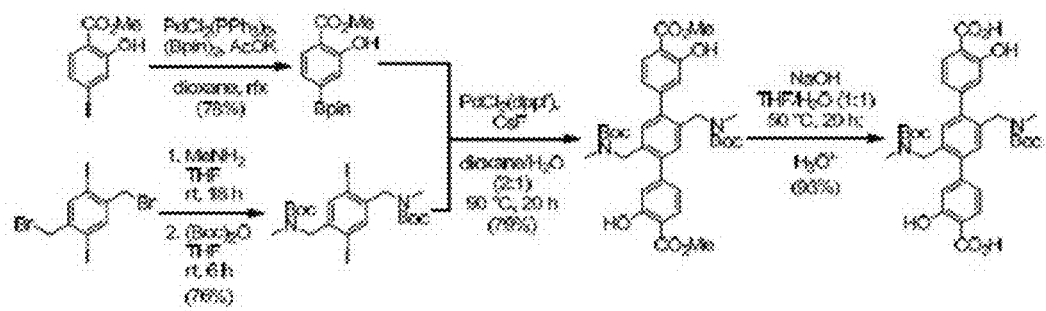
FIG. 10 presents a scheme for the synthesis of an ($CH_2NMeBoc$)$_2$ based organic linker that can be used to synthesize a functionalized Mg-IRMOF-74-III.
Figure 11:
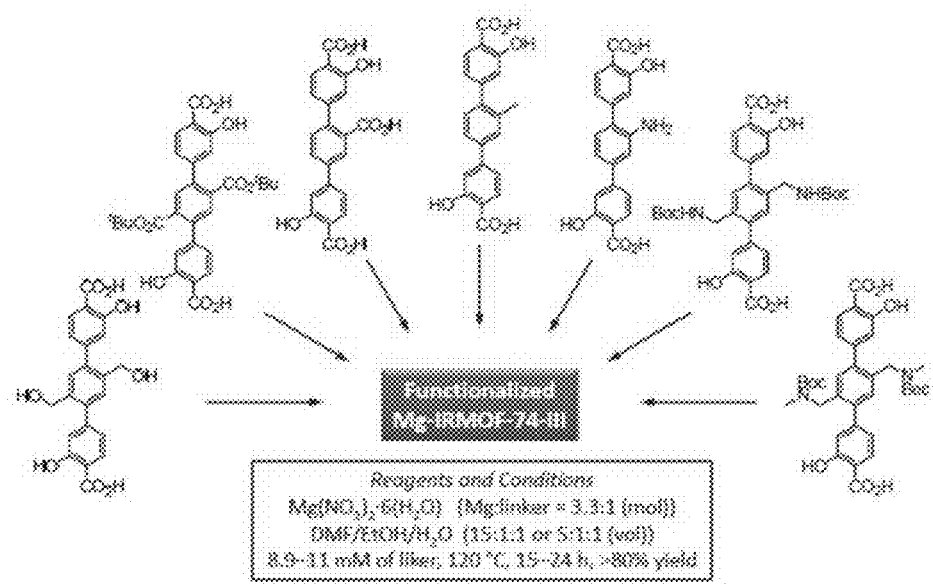
FIG. 11 presents various organic moieties with a variety of functional groups that can be used the synthesis of functionalized Mg-IRMOF-74-III.
Figure 12:
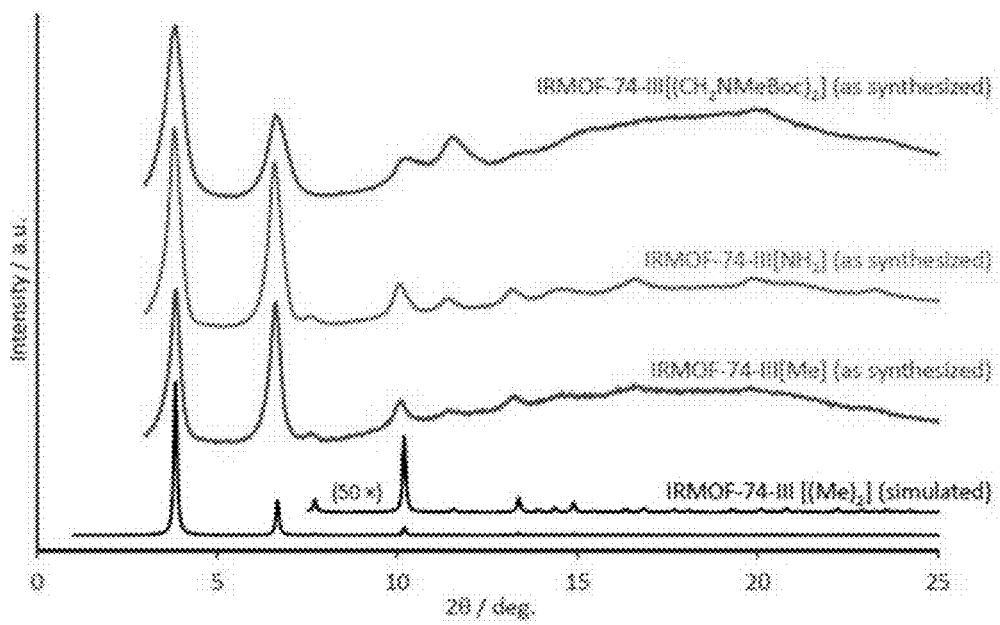
FIG. 12 presents PXRD patterns comparing the as-synthesized IRMOF-74-III products with the simulated patterns.
Figure 13:
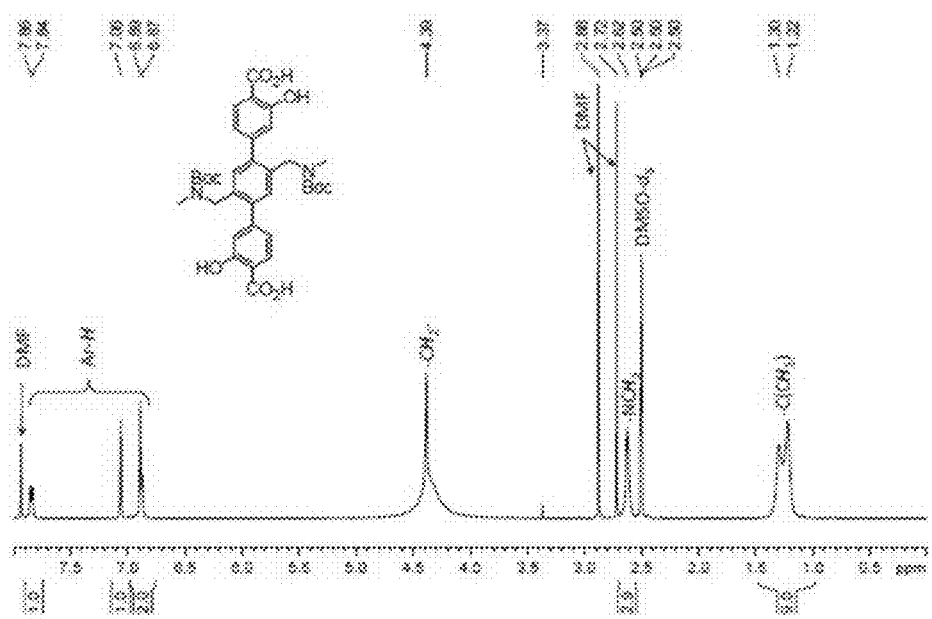
FIG. 13 provides an $^1H$ NMR spectrum of IRMOF-74-III[$(CH_2NMeBoc)_2$] at 400 MHz, using DMSO-$d_6$+DCl/$D_2O$. The NMR spectrum shows that the Boc groups are intact during MOF synthesis.
Figure 14:
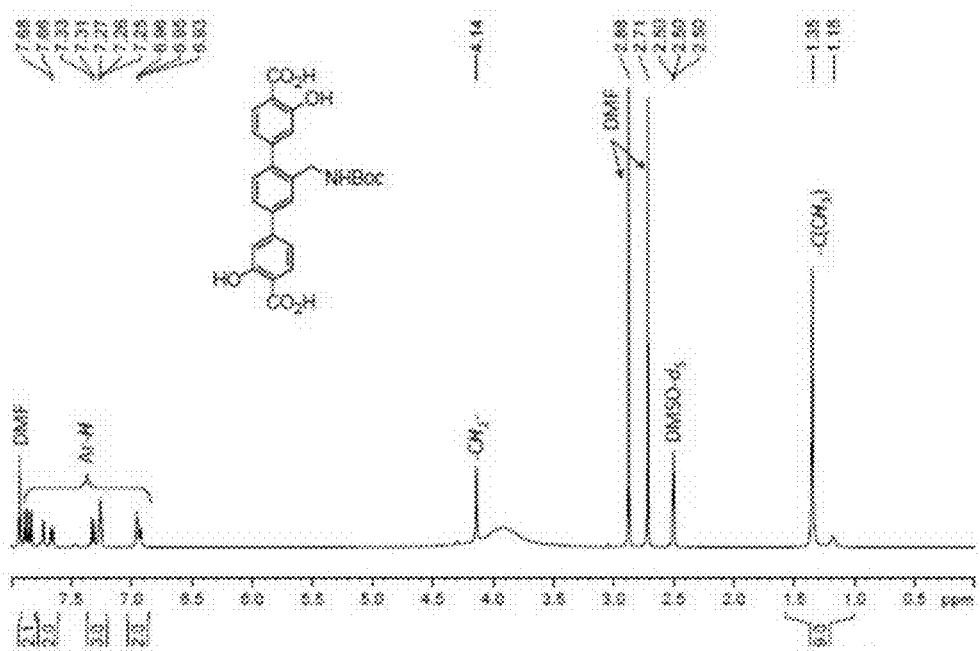
FIG. 14 provides an $^1$H NMR spectrum of IRMOF-74-III[CH$_2$NHBoc] at 400 MHz, using DMSO-d$_6$+DCl/D$_2$O. The NMR spectrum shows that the Boc groups are intact during MOF synthesis.
Figure 15:
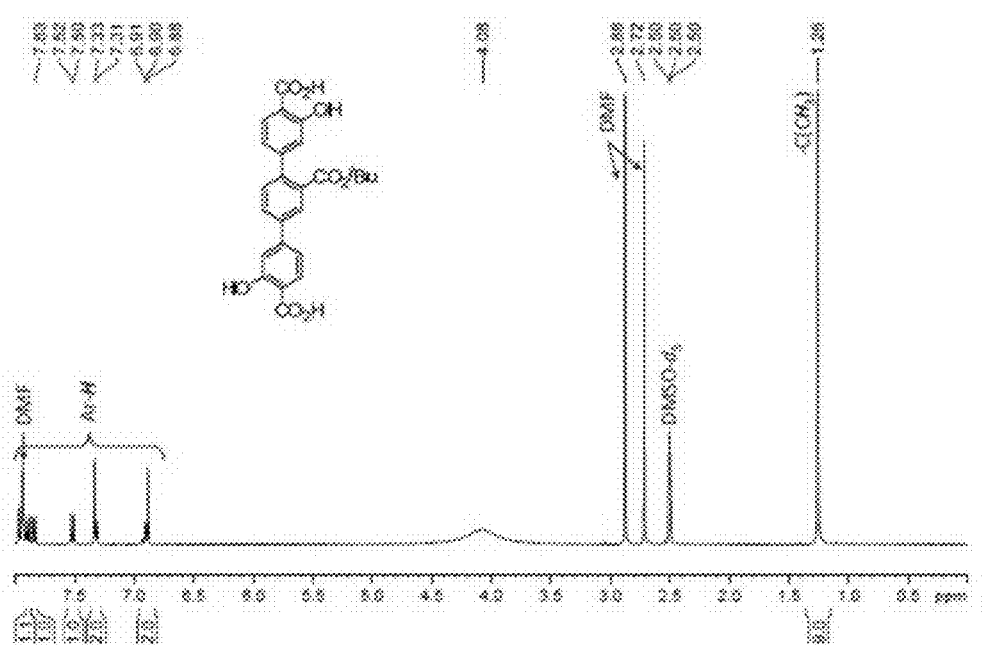
FIG. 15 provides an $^1$H NMR spectrum of IRMOF-74-III[CO$_2$$^t$Bu] at 400 MHz, using DMSO-d$_6$+DCl/D$_2$O. The NMR spectrum shows that the t-butyl groups are intact during MOF synthesis.
Figure 16:
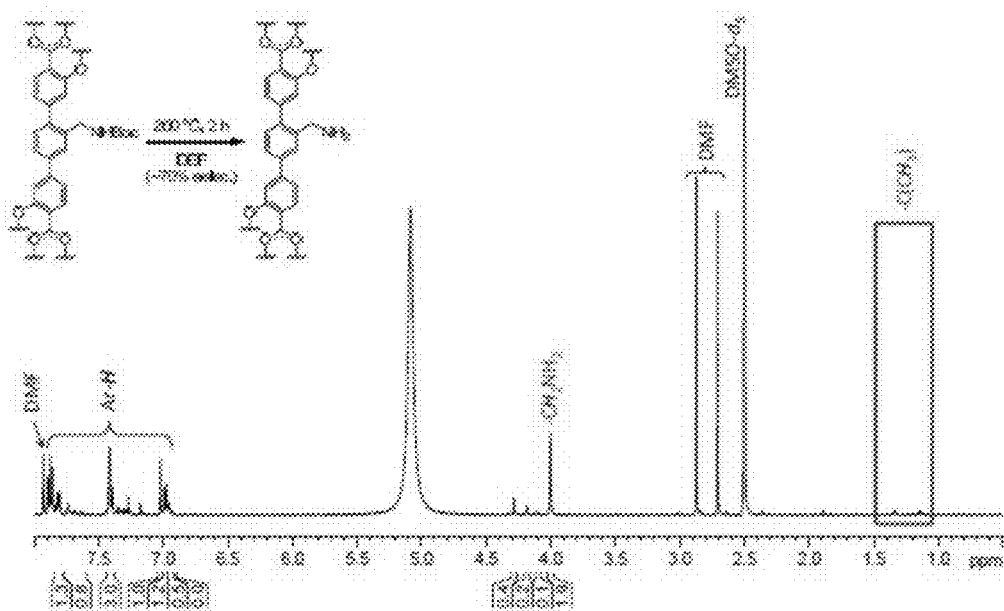
FIG. 16 provides an $^1$H NMR spectrum of deprotected IRMOF-74-III[CH$_2$NHBoc] at 400 MHz, using DMSO-d$_6$+DCl/D$_2$O. The NMR shows that by-products are formed when the Boc group was removed by heating at 200° C. for 2 hours in DEF.
Figure 17:
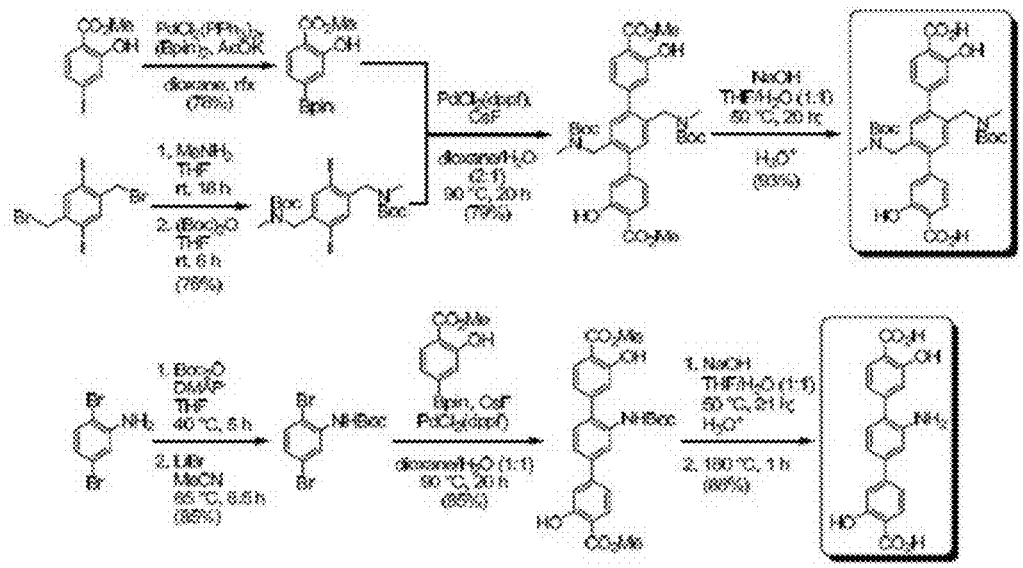
FIG. 17 provides for the synthesis of organic linking moieties that have sec- and aromatic amines.

In this embodiment, the organic linkers and their corresponding IRMOF-74-III structures were functionalized with —$CH_3$, —$NH_2$, —$CH_2NHBoc$, —$CH_2NMeBoc$, —$CH_2NH_2$, and —$CH_2NHMe$ (Boc=tertbutyloxycarbonyl), which point toward the center of the channels (FIG. 7B).

The disclosure also demonstrates the synthesis, characterization, porosity, and $CO_2$ capture properties (in dry and wet nitrogen streams) of IRMOF-74-III with the six different functionalities. At low pressure IRMOF-74-III-$CH_2NH_2$ and —$CH_2NHMe$ exhibit strong binding of $CO_2$ and have the highest uptake, and that in breakthrough experiments the —$CH_2NH_2$ form shows selectivity toward $CO_2$ in a wet nitrogen gas stream with 65% relative humidity (RH). Indeed, the behavior of this material under wet conditions remains unchanged from that observed under dry gas stream.

It is yet further contemplated by this disclosure that to enhance chemoselectivity it may be desirable to protect one or more functional groups that would generate unfavorable products upon a chemical reaction desired for another functional group, and then deprotect this protected group after the desired reaction is completed. Employing such a protection/deprotection strategy can be used for one or more functional groups of any organic linking ligand described herein, including any structures depicted herein. Accordingly, hydroxyl groups may further comprise a hydroxyl protecting group, amine groups may further comprise an amine protecting group, and carbonyl groups may further comprise a carbonyl protecting group, unless stated otherwise herein. In a particular embodiment, an organic linking moiety comprising one or more amine groups may further comprise a tert-butyl carbamate protecting group (Boc group) that can be removed during or post-synthesis of the MOF framework.

Examples of hydroxyl protecting groups include, but are not limited to, methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, guaiacolmethyl, tert-butoxymethyl, 4-pentenyloxymethyl, tert-butyldimethylsiloxymethyl, thexyldimethylsiloxymethyl, tert-butyldiphenylsiloxymethyl, 2-methoxyethoxymethyl, 2,2,2-trichloroethoxymethyl, bis(2-chloroethoxy)methyl, 2-(trimethylsilyl)ethoxymethyl, menthoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl and the like; Benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl (trityl), α-naphthyldiphenylmethyl, (4-methoxyphenyl)-diphenyl-methyl, di-(p-methoxyphenyl)-phenylmethyl, tri-(p-methoxyphenyl)methyl, 4-(4'-bromophenacyloxy)-phenyldiphenylmethyl, 4,4',4"-tris(4,5-dichlorophthalimidophenyl)methyl, 4,4',4"-tris(levulinoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(1 7-tetrabenzo[a,c,g,I]fluorenylmethyl)-4,4'-dimethoxytrityl, 9-anthryl, 9-(9-phenyl)xanthenyl, 9-(9-phenyl-10-oxo)anthryl and the like; trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like; —C(O)R$^{40}$, where R$^{40}$ is selected from the group consisting of alkyl, substituted alkyl, aryl and more specifically R$^{40}$=methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis(4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, α-naphthyl, benzoyl and the like; —C(O)OR$^{41}$, where R$^{41}$ is selected from alkyl, substituted alkyl, aryl and more specifically R$^{41}$=methyl, methoxymethyl, 9-fluorenylmethyl, ethyl, 2,2,2-trichloromethyl, 1,1-dimethyl-2,2,2-trichloroethyl, 2-(trimethylsilyl)ethyl, 2-(phenylsulfonyl)ethyl, isobutyl, tert-butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, 4-ethoxy-1-naphthyl and the like.

Examples of carbonyl protecting groups include, but are not limited to, dimethyl acetal, 1-3-dioxane, 1-3-dioxolane, S,S'-dimethylthioacetal, 1,3-dithiane, 1,3-dithiolane, 1,3-oxathiolane, methyl ester, t-Butyl ester, allyl ester, 1,1-dimethylallyl ester, 2,2,2-trifluoroethyl ester, phenyl ester, benzyl ester, 4-methoxybenzyl ester, silyl ester, ortho ester, 9-fluorenylmethyl esters, 2-(trimethylsilyl)ethoxymethyl ester, 2-(trimethylsily)ethyl ester, halo esters, o-nitrobenzyl ester, and OBO ester.

Examples of amine protecting groups include, but are not limited to, methyl carbonate, 9-fluorenylmethyl carbamate (Fmoc), 2,2,2-trichloroethyl carbamate (Troc), t-butyl carbamate (Boc), 2-(trimethylsilyl)ethyl carbamate (Teoc), allyl carbamate (Alloc), benzyl carbamate (Cbz), trifluoroacetamide, benzylamine, allylamine, and tritylamine.

All the aforementioned linking moieties that possess appropriate reactive functionalities can be chemically transformed by a suitable reactant post-synthesis of the framework to add further functionalities to the framework. By modifying the organic links within the framework post-synthetically, access to functional groups that were previously inaccessible or accessible only through great difficulty and/or cost is possible and facile.

The MOFs of the disclosure may be generated by first utilizing a plurality of linking moieties having different functional groups, wherein at least one of these functional groups may be modified, substituted, or eliminated with a different functional group post-synthesis of the framework. In other words, at least one linking ligand comprises a functional group that may be reacted with a post-framework reactant to further increase the diversity of the functional groups of the MOFs disclosed herein. In a particular embodiment, the MOF disclosed herein is MOF-74 or IRMOF-74 comprising one or more types of differently functionalized linking ligands wherein one or more types of the linking ligands can undergo post-synthetic modification with post-framework reactant so as to further functionalize the framework.

In a further embodiment, the MOFs of the disclosure may be further modified by reacting with one or more post-framework reactants that may or may not have denticity. In another embodiment, a MOF as-synthesized is reacted with at least one, at least two, or at least three post-framework reactants. In yet another embodiment, a MOF as-synthesized is reacted with at least two post-framework reactants. In a further embodiment, a MOF as-synthesized is reacted with at least one post-framework reactant that will result in adding denticity to the framework.

The disclosure provides that a MOF disclosed herein can be modified by a post-framework reactant by using chemical reactions that modify, substitute, or eliminate a functional group post-synthesis. These chemical reactions may use one or more similar or divergent chemical reaction mechanisms depending on the type of functional group and/or post-framework reactant used in the reaction. Examples of chemical reaction include, but are not limited to, radical-based, unimolecular nuclephilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloaddition, ring closing metathesis (RCM), pericylic, electrocylic, rearrangement, carbene, carbenoid, cross coupling, and degradation. Other agents can be added to increase the rate of the reactions disclosed herein, including adding catalysts, bases, and acids.

In another embodiment, a post-framework reactant adds at least one effect to a MOF of the disclosure including, but not limited to, modulating the gas storage ability of the MOF; modulating the sorption properties of the MOF; modulating the pore size of the MOF; modulating the catalytic activity of the MOF; modulating the conductivity of the MOF; and modulating the sensitivity of the MOF to the presence of an analyte of interest. In a further embodiment, a post-framework reactant adds at least two effects to the MOF of the disclosure including, but not limited to, modulating the gas storage ability of the MOF; modulating the sorption properties of the MOF; modulating the pore size of the MOF; modulating the catalytic activity of the MOF; modulating the conductivity of the MOF; and modulating the sensitivity of the MOF to the presence of an analyte of interest.

In one embodiment, a post-framework reactant can be a saturated or unsaturated heterocycle. In another embodiment, a post-framework reactant has 1-20 carbons with functional groups including atoms such as N, S, and O.

In yet another embodiment, a post-framework reactant is selected to modulate the size of the pores of a MOF disclosed herein.

In another embodiment, a post-framework reactant is selected to increase the hydrophobicity of a MOF disclosed herein.

In yet another embodiment, a post-framework reactant is selected to modulate gas separation of a MOF disclosed herein. In a certain embodiment, a post-framework reactant creates an electric dipole moment on the surface of a MOF of the disclosure when it chelates a metal ion.

In a further embodiment, a post-framework reactant is selected to modulate the gas sorption properties of a MOF of the disclosure. In another embodiment, a post-framework reactant is selected to promote or increase greenhouse gas sorption of a MOF disclosed herein. In another embodiment, a post-framework reactant is selected to promote or increase hydrocarbon gas sorption of a MOF of the disclosure.

In yet a further embodiment, a post-framework reactant is selected to increase or add catalytic efficiency to a MOF disclosed herein.

In another embodiment, a post-framework reactant is selected so that organometallic complexes can be tethered to a MOF of the disclosure. Such tethered organometallic complexes can be used, for example, as heterogeneous catalysts.

In a particular embodiment, a MOF of the disclosure can be used for a variety of applications, including for catalysis, gas storage, gas separation, or water storage and release.

In one embodiment, a gas storage or gas separation material comprising a MOF of the disclosure is provided. Advantageously, a MOF of the disclosure includes a number of adsorption sites for storing and/or separating gas molecules. Suitable examples of such gases include, but are not limited to, gases comprising ammonia, argon, methane, propane, carbon dioxide, carbon monoxide, sulfur dioxide, hydrogen sulfide, phosphine, nitrous oxide, hydrogen, oxygen, nitrogen, fluorine, chlorine, helium, carbonyl sulfide, and combinations thereof. In a particularly useful variation, a MOF disclosed herein is a hydrogen storage material that is used to store hydrogen ($H_2$). In another particularly useful variation, a MOF disclosed herein is a carbon dioxide storage material that may be used to separate carbon dioxide from a gaseous mixture. In yet another particularly useful variation, a MOF disclosed herein is a methane storage material that may be used to separate methane from a gaseous mixture.

The disclosure also provides an apparatus and method for separating one or more components from a multi-component gas using a separation system having a feed side and an effluent side separated by a MOF of the disclosure. The apparatus may comprise a column separation format.

"Natural gas" refers to a multi-component gas obtained from a crude oil well (associated gas) or from a subterranean gas-bearing formation (non-associated gas). The composition and pressure of natural gas can vary significantly. A typical natural gas stream contains methane as a significant component. The natural gas will also typically contain ethane, higher molecular weight hydrocarbons, one or more acid gases (such as carbon dioxide, hydrogen sulfide, carbonyl sulfide, carbon disulfide, and mercaptans), and minor amounts of contaminants such as water, nitrogen, iron sulfide, wax, and crude oil. In a particular embodiment, a MOF of the disclosure can be used as an adsorbent for methane. In a certain embodiment, a MOF disclosed herein can be used to separate and/or store one or more gases from a natural gas stream. In another embodiment, a MOF disclosed herein can be used to separate and/or store methane from a natural gas stream. In yet another embodiment, a MOF disclosed herein can be used to separate and/or store methane from a town gas stream. In yet another embodiment, a MOF disclosed herein can be used to separate and/or store methane from a biogas stream. In a certain embodiment, a MOF disclosed herein can be used to separate and/or store methane from a syngas stream. In an alternate embodiment, a MOF disclosed herein can be used to separate and/or store hexane isomers from a mixed gas stream.

In a particular embodiment, a MOF disclosed herein is part of a device. In another embodiment, a gas separation device comprises a MOF of the disclosure. In a further embodiment, a gas separation device used to separate one or more component gases from a multi-component gas mixture comprises a MOF disclosed herein. Examples of gas separation and/or gas storage devices include, but are not limited to, purifiers, filters, scrubbers, pressure swing adsorption devices, molecular sieves, hollow fiber membranes, ceramic membranes, cryogenic air separation devices, and hybrid gas separation devices. In a certain embodiment, a gas separation device used to separate one or more gases with high electron density from gas mixture comprises a MOF of the disclosure. In a further embodiment, a gas separation device used to separate methane, nitrogen, carbon dioxide, of water from a mixed gas stream comprises a MOF of the disclosure.

In a particular embodiment of the disclosure, a gas storage material comprises a MOF disclosed herein. A gas that may be stored or separated by the methods, compositions and systems of the disclosure includes gases such as ammonia, argon, methane, propane, carbon dioxide, carbon monoxide, sulfur dioxide, hydrogen sulfide, phosphine, nitrous oxide, hydrogen, oxygen, nitrogen, fluorine, chlorine, helium, carbonyl sulfide, and combinations thereof. In particularly useful variation, a gas binding material is a carbon dioxide binding material that may be used to separate carbon dioxide from a gaseous mixture. In another particularly useful variation a gas storage material is a hydrogen storage material that is used to store hydrogen ($H_2$). In another particularly useful variation, a gas storage material is a carbon dioxide storage material that may be used to separate methane from a gaseous mixture.

In yet a further embodiment, a MOF disclosed herein can be used to separate and/or store one or more gases selected from the group comprising ammonia, argon, methane, propane, carbon dioxide, carbon monoxide, sulfur dioxide, hydrogen sulfide, phosphine, nitrous oxide, hydrogen, oxygen, nitrogen, fluorine, chlorine, helium, and carbonyl sulfide. In yet another embodiment, a MOF disclosed herein can be used to separate and/or store methane or hydrogen. In a certain embodiment, a MOF disclosed herein can be used to separate and/or store methane. In an embodiment, a MOF disclosed herein can be used to separate and/or store $CO_2$.

In another embodiment, a gas storage device comprises a MOF disclosed herein. In a further embodiment, a gas storage device used to adsorb and/or absorb one or more component gases from a multi-component gas mixture comprises a MOF disclosed herein. In a certain embodiment, a gas storage device used to adsorb and/or absorb methane, hydrogen, carbon dioxide, or water from gas mixture comprises a MOF disclosed herein.

In a certain embodiment, a MOF of the disclosure can be used as heterogeneous catalysts. A MOF can be synthesized to have catalytic activity or be functionalized post synthetically with a post-framework reactant to become catalytic. Catalytic activities would include, but are not limited to, hydrolysis reactions, oxidations, reductions, ring closure reactions, metathesis reactions, and isomerizations.

The disclosure also provides methods using a MOF disclosed herein. In a certain embodiment, a method to separate or store one or more gases comprises contacting one or more gases with a MOF of the disclosure. In a further embodiment, a method to separate or store one or more gases from a mixed gas mixture comprises contacting the gas mixture with a MOF disclosed herein. In a certain embodiment, a method to separate or store one or more gases from a fuel gas stream comprises contacting the fuel gas stream with a MOF disclosed herein. In a further embodiment, a method to separate or store methane from a natural gas stream comprises contacting the natural gas stream with a MOF disclosed herein. In yet another embodiment, a method to separate or store water from the exhaust of a combustion engine comprises contacting the exhaust with a MOF disclosed herein. In a certain embodiment, a method to separate or store one or more gases from flue-gas comprises contacting the flue-gas with a MOF disclosed herein.

Sorption is a general term that refers to a process resulting in the association of atoms or molecules with a target material. Sorption includes both adsorption and absorption.

Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

MOFs of the disclosure can be used as standard compounds for sorption instruments, and obtained results would be helpful to improve various industrial plants (i.e. separation or recovery of chemical substance).

In a variation of this embodiment, the gaseous storage site comprises a MOF with a pore which has been functionalized with a group having a desired size or charge. In a refinement, this activation involves removing one or more chemical moieties (guest molecules) from a MOF disclosed herein. Typically, such guest molecules include species such as water, solvent molecules contained within a MOF disclosed herein, and other chemical moieties having electron density available for attachment.

A MOFs used in the embodiments of the disclosure include a plurality of pores for gas adsorption. In one variation, the plurality of pores has a unimodal size distribution. In another variation, the plurality of pores have a multimodal (e.g., bimodal) size distribution.

The following examples are intended to illustrate but not limit the disclosure. While they are typical of those that might be used, other procedures known to those skilled in the art may alternatively be used.

EXAMPLES

Example 1: mm-MOFs

General Procedure for Preparing Mm-MOF-74 Compounds 2,5-dihydroxyterephthalic acid ($H_4DOT$), cobalt nitrate hexahydrate [$Co(NO_3)_2 \cdot 6H_2O$], magnesium nitrate hexahydrate [$Mg(NO_3)_2 \cdot 6H_2O$], nickel nitrate hexahydrate [$Ni(NO_3)_2 \cdot 6H_2O$], zinc nitrate hexahydrate [$Zn(NO_3)_2 \cdot 6H_2O$], manganese nitrate tetrahydrate [$Mn(NO_3)_2 \cdot 4H_2O$], strontium nitrate [$Sr(NO_3)_2$], iron acetate [$Fe(OAc)_2$], calcium nitrate tetrahydrate [$Ca(NO_3)_2 \cdot 4H_2O$], barium nitrate [$Ba(NO_3)_2$], and cadmium acetate dihydrate [$Cd(OAc)_2 \cdot 2H_2O$], N,N-dimethylformamide (DMF), ethanol (EtOH), and methanol (MeOH) were purchased from Aldrich Chemical Co.

mm-MOF-74 compounds were synthesized using varying amounts of metal salts combined with $H_4DOT$. The solid reagents were then dissolved in DMF/EtOH/water (in a 15:1:1 ratio respectively) and heated at 120° C. for 20-24 h. The resulting crystals were soaked and washed, first with 75 mL of fresh DMF solvent for 5 exchanges over a 3 day period, and then with 180 mL of anhydrous MeOH for 12 exchanges over a 4 day period. The porous MOF compounds were then activated to remove all solvent by evacuating under vacuum (100-200 mTorr) overnight, and then heating stepwise under vacuum at 4° C./min to 80° C. and held at that temperature for 1 h, then at 4° C./min to 100° C. and held for 1 h, then at 4° C./min to 150° C. and held for 1 h, then at 4° C./min to 200° C. and held for 1 h, and lastly at 4° C./min to 250° C. held for 10 h (30 mTorr). Synthesis of each MM-MOF-74 compound was repeated three separate times. The PXRD pattern of each sample was checked to match the simulated MOF-74 powder pattern. The metal values were recorded by inductively coupled plasma optical emission (ICP-OES) spectroscopy. The averaged values for the three experiments for each compound is reported with standard errors in Table 1.

Elemental Analysis of MM-MOF-74 Compounds.

All measurements for the analysis of carbon, hydrogen, and nitrogen were taken on a Thermo (Carlo Erba) Flash EA112 Combustion CHNS analyzer using 2-3 mg of a mm-MOF-74 sample.

Metal detection for all samples was carried out on a TJA radial IRIS 1000 ICP-OES spectroscope with a charge injection device array of 512×512 pixels of a continuous wavelength detector. All solid samples (0.5-1 mg) were first digested using 200 microliters of fuming nitric acid purchased from Aldrich Chemical Co., and then the samples were diluted with 2% nitric acid to a total volume of 10 mL in a volumetric flask. The solutions were then transferred to low density polyethylene tubes purchased from Fisher Scientific International Inc. The solution, 2% nitric acid in water, was prepared by using fuming nitric acid purchased from Aldrich Chemical Co. and ultrapure water. The solid MOF samples immediately dissolved upon treatment with 2% nitric acid. All glassware for ICP-OES was rinsed thoroughly for a minimum of five times with ultrapure water. Standards were prepared from Inorganic Ventures' multi-element standard solutions of Mg, Ca, Sr, Ba, Mn, Fe, Co, Ni, Zn, and Cd. R.F. power was 1150 watts, auxiliary flow was 0.5 L/min, nebulizer flow was 32.06 psi, pump rate was 70 rpm, CID temperature was −41° C., and the FPA temperature was 28.3° C.

Relative amounts (moles) of metals in the empirical formula were determined from experimental weight percent values. The linker, DOT, has a total anionic charge of four, with a minus charge on each carboxylate group and a minus charge on each hydroxyl group. Charge balance was achieved by assuming all metals were divalent and constraining the total moles of metals to 1.0. The empirical equations were then fit by varying the number of water molecules.

Powder X-Ray Diffraction Analysis of MM-MOF-74 Compounds.

All PXRD patterns were collected with a Bruker AXS D8 Advance diffractometer at 40 kV, 40 mA using Cu Kα radiation ($\lambda = 1.5406$ Å). The PXRD pattern for each compound was compared to a simulated MOF-74 PXRD pattern. The simulated MOF-74 PXRD pattern was calculated using the software Powder Cell v. 2.2.

Synthesis of MM-MOF-74s (Mg, Co) M2M-MOF-74, $Mg_{0.428}Co_{1.572}(DOT) \cdot (H_2O)_{8.2}$ $H_4DOT$ (30 mg, $1.5 \times 10^{-4}$ mol), $Mg(NO_3)_2 \cdot 6H_2O$ (58.2 mg, $2.27 \times 10^{-4}$ mol), $Co(NO_3)_2 \cdot 6H_2O$ (66.1 mg, $2.27 \times 10^{-4}$ mol) were sonicated and dissolved in 10 mL DMF, 0.6 mL EtOH, and 0.6 mL $H_2O$ in a 20-mL scintillation vial. The vial was sealed tightly and placed in an isothermal oven at 120° C. for 20 h for the completion of the solvothermal reaction. The resulting as-synthesized product was a red microcrystalline powder. Different sizes of rod shaped single crystals and aggregates were seen under an optical microscope. The PXRD pattern of the synthesized compound matches the simulated MOF-74 powder diffraction pattern. Elemental Analysis (activated): Calculated for $Mg_{0.428}Co_{1.572}CH_{18.4}O_{14.2}=Mg_{0.428}Co_{1.572}(DOT)$. $(H_2O)_{8.2}$: C, 21.60; H, 4.17; N, 0.00. Found (%): C, 21.18; H, 4.12; N, <0.1.

(Mg, Co, Ni, Zn) M4M-MOF-74, $Mg_{0.190}Co_{0.612}Ni_{0.562}Zn_{0.636}(DOT).(H_2O)_{8.4}$:

$H_4DOT$ (30 mg, $1.5\times10^{-4}$ mol), $Mg(NO_3)_2.6H_2O$ (30.7 mg, $1.20\times10^{-4}$ mol), $Co(NO_3)_2.6H_2O$ (34.9 mg, $1.20\times10^{-4}$ mol), $Ni(NO_3)_2.6H_2O$ (34.9 mg, $1.20\times10^{-4}$ mol), $Zn(NO_3)_2.6H_2O$ (35.7 mg, $1.20\times10^{-4}$ mol) were sonicated and dissolved in 10 mL DMF, 0.6 mL EtOH, and 0.6 mL $H_2O$ in a 20-mL scintillation vial. The vial was sealed tightly and placed in an isothermal oven at 120° C. for 24 h for the completion of the solvothermal reaction. The resulting as-synthesized product was an orange microcrystalline powder. Different sizes of rod shaped single crystals and aggregates were seen under an optical microscope. The PXRD pattern of the synthesized compound matches the simulated MOF-74 powder diffraction pattern. Elemental Analysis (activated): Calculated for $Mg_{0.190}Co_{0.612}Ni_{0.562}Zn_{0.636}C_8H_{18.8}O_{14.4}=Mg_{0.190}Co_{0.612}Ni_{0.562}Zn_{0.636}(DOT)$. $(H_2O)_{8.4}$(%): C, 20.86; H, 4.11; N, 0.00. Found (%): C, 20.37; H, 3.72; N, <0.1.

(Mg, Sr, Mn, Co, Ni, Zn) M6M-MOF-74, $Mg_{0.124}Sr_{0.004}Mn_{0.212}Co_{0.592}Ni_{0.528}Zn_{0.540}(DOT)$. $(H_2O)_{8.2}$:

$H_4DOT$ (30 mg, $1.5\times10^{-4}$ mol), $Mg(NO_3)_2.6H_2O$ (25.6 mg, $9.98\times10^{-5}$ mol), $Sr(NO_3)_2$ (21.2 mg, $1.00\times10^{-4}$ mol), $Mn(NO_3)_2.4H_2O$ (25.1 mg, $1.00\times10^{-4}$ mol), $Co(NO_3)_2.6H_2O$ (29.1 mg, $1.00\times10^{-4}$ mol), $Ni(NO_3)_2.6H_2O$ (29.1 mg, $1.00\times10^{-4}$ mol), $Zn(NO_3)_2.6H_2O$ (29.7 mg, $9.98\times10^{-5}$ mol) were sonicated and dissolved in 10 mL DMF, 0.6 mL EtOH, and 0.6 mL $H_2O$ in a 20-mL scintillation vial. The vial was sealed tightly and placed in an isothermal oven at 120° C. for 22 h for the completion of the solvothermal reaction. The resulting as-synthesized product was a green-black microcrystalline powder. Crystals were too small to be seen under an optical microscope. The PXRD pattern of the synthesized compound matches the simulated MOF-74 powder diffraction pattern. Elemental Analysis (activated): Calculated for $Mg_{0.124}Sr_{0.004}Mn_{0.212}Co_{0.592}Ni_{0.528}Zn_{0.540}C_8H_{18.4}O_{14.2}=Mg_{0.124}Sr_{0.004}Mn_{0.212}Co_{0.592}Ni_{0.528}Zn_{0.540}(DOT)$. $(H_2O)_{8.2}$(%): C, 20.98; H, 4.05; N, 0.00. Found (%): C, 20.89; H, 3.61; N, <0.1.

(Mg, Ca, Sr, Mn, Fe, Co, Ni, Zn) M8M-MOF-74, $Mg_{0.268}Ca_{0.034}Sr_{0.048}Mn_{0.258}Fe_{0.314}Co_{0.432}Ni_{0.392}Zn_{0.254}(DOT).(H_2O)_{8.2}$:

$H_4DOT$ (30 mg, $1.5\times10^{-4}$ mol), $Mg(NO_3)_2.6H_2O$ (14.6 mg, $5.69\times10^{-5}$ mol), $Ca(NO_3)_2.4H_2O$ (13.5 mg, $5.72\times10^{-5}$ mol), $Sr(NO_3)_2$ (12.1 mg, $5.72\times10^{-5}$ mol), $Mn(NO_3)_2.4H_2O$ (14.3 mg, $5.70\times10^{-5}$ mol), $Fe(OAc)_2$ (9.9 mg, $5.7\times10^{-5}$ mol), $Co(NO_3)_2.6H_2O$ (16.5 mg, $5.67\times10^{-5}$ mol), $Ni(NO_3)_2.6H_2O$ (16.5 mg, $5.67\times10^{-5}$ mol), $Zn(NO_3)_2.6H_2O$ (16.7 mg, $5.61\times10^{-5}$ mol) were sonicated and dissolved in 10 mL DMF, 0.6 mL EtOH, and 0.6 mL $H_2O$ in a 20-mL scintillation vial. The vial was sealed tightly and placed in an isothermal oven at 120° C. for 24 h for the completion of the solvothermal reaction. The resulting as-synthesized product was a black microcrystalline powder. Crystals were too small to be seen under an optical microscope. The PXRD pattern of the synthesized compound matches the simulated MOF-74 powder diffraction pattern. Elemental Analysis (activated): Calculated for $Mg_{0.268}Ca_{0.034}Sr_{0.048}Mn_{0.258}Fe_{0.314}Co_{0.432}Ni_{0.392}Zn_{0.254}C_8H_{18.4}O_{14.2}=Mg_{0.268}Ca_{0.034}Sr_{0.048}Mn_{0.258}Fe_{0.314}Co_{0.432}Ni_{0.392}Zn_{0.254}(DOT)$. $(H_2O)_{8.2}$(%): C, 21.49; H, 4.06; N, 0.00. Found (%): C, 20.96; H, 4.12; N, <0.1.

(Mg, Ca, Sr, Ba, Mn, Fe, Co, Ni, Zn, Cd) M10M-MOF-74, $Mg_{0.269}Ca_{0.022}Sr_{0.030}Ba_{0.075}Mn_{0.234}Fe_{0.422}Co_{0.272}Ni_{0.282}Zn_{0.199}Cd_{0.19}(DOT).(H_2O)$ 7.8:

$H_4DOT$ (30 mg, $1.5\times10^{-4}$ mol), $Mg(NO_3)_2.6H_2O$ (11.6 mg, $4.52\times10^{-5}$ mol), $Ca(NO_3)_2.4H_2O$ (10.6 mg, $4.49\times10^{-5}$ mol), $Sr(NO_3)_2$ (9.6 mg, $4.5\times10^{-5}$ mol), $Ba(NO_3)_2$ (11.8 mg, $4.52\times10^{-5}$ mol), $Mn(NO_3)_2.4H_2O$ (11.3 mg, $4.50\times10^{-5}$ mol), $Fe(OAc)_2$ (7.9 mg, $4.5\times10^{-5}$ mol), $Co(NO_3)_2.6H_2O$ (13.2 mg, $4.54\times10^{-5}$ mol), $Ni(NO_3)_2.6H_2O$ (13.2 mg, $4.54\times10^{-5}$ mol), $Zn(NO_3)_2.6H_2O$ (13.4 mg, $4.50\times10^{-5}$ mol), $Cd(OAc)_2.2H_2O$ (12.0 mg, $4.50\times10^{-5}$ mol) were sonicated and dissolved in 10 mL DMF, 0.6 mL EtOH, and 0.6 mL $H_2O$ in a 20-mL scintillation vial. The vial was sealed tightly and placed in an isothermal oven at 120° C. for 24 h for the completion of the solvothermal reaction. The resulting as-synthesized product was a black microcrystalline powder. Crystals were too small to be seen under an optical microscope. The PXRD pattern of the synthesized compound matches the simulated MOF-74 powder diffraction pattern. Elemental Analysis (activated): Calculated for $Mg_{0.269}Ca_{0.022}Sr_{0.030}Ba_{0.075}Mn_{0.234}Fe_{0.422}Co_{0.272}Ni_{0.282}Zn_{0.199}Cd_{0.196}C_8H_{17.6}O_{13.8}=Mg_{0.269}Ca_{0.022}Sr_{0.030}Ba_{0.075}Mn_{0.234}Fe_{0.422}Co_{0.272}Ni_{0.282}Zn_{0.199}Cd_{0.196}(DOT).(H_2O)$ 7.8(%): C, 20.93; H, 3.86; N, 0.00. Found (%): C, 21.41; H, 3.67; N, <0.1.

Scanning Electron Microscopy Imaging (SEM).

All MM-MOF-74 samples were prepared for SEM by dispersing the material onto a double sided adhesive conductive carbon tape that was attached to a flat aluminum sample holder. The samples were imaged at a working distance of 5-6 mm with accelerating voltage of 10 kV using a low vacuum detector (LVD) on an FEI Nova NanoSEM 230. Several samples of each MM-MOF-74 compound were imaged and compared. Multiple regions of each compound were seen to have crystalline material of the same morphology in varying sizes and aggregations.

Thermogravimetric Analysis (TGA).

TGA measurements for all MM-MOF-74 samples were collected using a Perkin Elmer Pyris Diamond TG/DTA. Samples were heated at a constant rate of 5° C./min in a continuous air flow atmosphere (200 mL/min flow rate) on a platinum pan. The samples were activated prior to sample loading and weight stabilization, which was done in air. The TGA profiles for MM-MOF-74 compounds are similar to those of the single-metal MOF-74 compounds.

The first weight loss (100-270° C.) is attributed to the removal of occluded and coordinated water molecules. The second weight loss (approximately 300° C.) is related to the decomposition of organic linkers in air and the residual weight percent is assigned to the remaining metal oxides.

The weight percent of water molecules observed in the TGA curve (calculated value) for M2M-, M4M-, M6M-, M8M-, and M10M-MOF-74 are found to be 31.5% (33.2%), 29.9% (32.9%), 29.1% (32.3%), 32.0% (32.8%), and 34.3% (30.6%), respectively. If MgO, CaO, SrO, BaO, $MnO_2$, $Fe_2O_3$, CoO, NiO, ZnO, and CdO are selectively formed as metal oxide residues, the final weight percent of the residue (calc. value) for M2M-, M4M-, M6M-, M8M-, and M10M-MOF-74 is estimated to be 30.6% (30.4%), 34.6% (32.0%), 33.0% (33.1%), 36.3% (32.7%), and 34.0% (35.6%), respectively. The observed values for the first weight loss and final metal oxide residues are in good agreement with the calculated values.

$N_2$ Adsorption Measurements.

The porosities of the M2M-, M4M-, M6M-, M8M-, and M10M-MOF-74 were investigated using a Quantachrome Autosorb-1 volumetric gas adsorption analyzer. All samples were activated and loaded into the sample holder in an argon glovebox. The $N_2$ adsorption measurements were carried out at 77 K, using a liquid $N_2$ bath. Ultra-high-purity grade $N_2$ and He (99.999% purity) were used throughout the adsorption experiments.

X-Ray Energy Dispersive Spectroscopy (EDS).

All MM-MOF-74 compounds for EDS were analyzed were prepared in the same way as for SEM in an FEI Nova NanoSEM 230 operated at 15 kV with Thermo Fisher Scientific Noran System Six Energy Dispersive X-ray Spectrometer. The metals were identified for localized regions using the point and shoot mode. The samples were all analyzed at several different areas that are not closely neighboring one another to get a survey of the metals in the sample. Mapping of the metals and oxygen for some of the compounds were also taken using spectral mapping mode. Table 1 presents normalized ratios.

Example 2: Multi-Linker MOF-74

Synthesis of organic linkers—General: All reactions were carried out under nitrogen unless otherwise noted. Tetrahydrofuran (THF) and dichloromethane ($CH_2Cl_2$) were treated with a Grubbs-type apparatus prior to use. Anhydrous N,N-dimethylformamide (DMF), and methanol were obtained from EMD Millipore Chemicals. Other solvents and reagents were obtained from commercial sources and used without further purification. $^1H$ and $^{13}C\{^1H\}$ NMR spectra were acquired on a Bruker ARX-500 (500 MHz), DRX-500 (500 MHz), or AVB-400 (400 MHz) spectrometer at 297-300 K, and chemical shifts were calculated using the solvent resonances as internal standards ($^1H$: 7.26 ppm for $CHCl_3$, 2.05 ppm for acetone-$d_6$, 2.50 ppm for DMSO; $^{13}C\{^1H\}$: 77.00 ppm for $CDCl_3$, 29.84 ppm for acetone-$d_6$, 39.51 ppm for DMSO-$d_6$). Infrared spectra were recorded on a Bruker ALPHA Platinum ATR-FTIR Spectrometer equipped with a single reflection diamond ATR module, and wavenumbers are reported in $cm^{-1}$ with peak descriptions: s (strong), m (medium), w (weak), br (broad), sh (shoulder). High Resolution Electrospray Ionization mass (HR-ESI) was acquired on an Finnigan LTQ FT (Thermo Electron Corporation) instrument, using negative mode and by direct injection of methanol solutions of the samples using syringe pump with a flow rate of 5 µL $min^{-1}$. Column chromatography was performed on silica gel purchased from Sorbent Technologies (standard grade, 60 Å, 40-63 µm). Analytical thin layer chromatography (TLC) was performed on Whatman 250 µm-thick silica gel 60 plates with a fluorescent indicator. Visualization of TLC spots was accomplished with UV light at 254 nm.

Procedures and Spectral Data.

Synthesis of organic linkers 5a-5d was started with Miyaura borylation of commercially available iodide 1. The resulting pinacol borate 2 was then subjected to the two fold Suzuki coupling with dibromide 3a-3d to give the corresponding dimethyl terphenyldicarboxylate derivatives 4a-4d. The target linkers were obtained by saponification of 4a-4d followed by, in the case of aniline derivative 5b, thermolysis of the Boc protecting group. The procedure is summarized in Scheme 1.

Scheme 1:

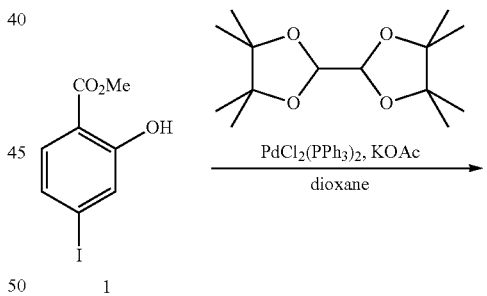

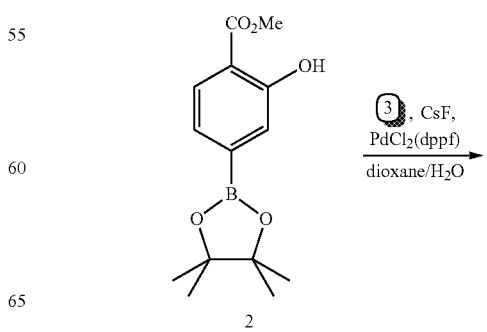

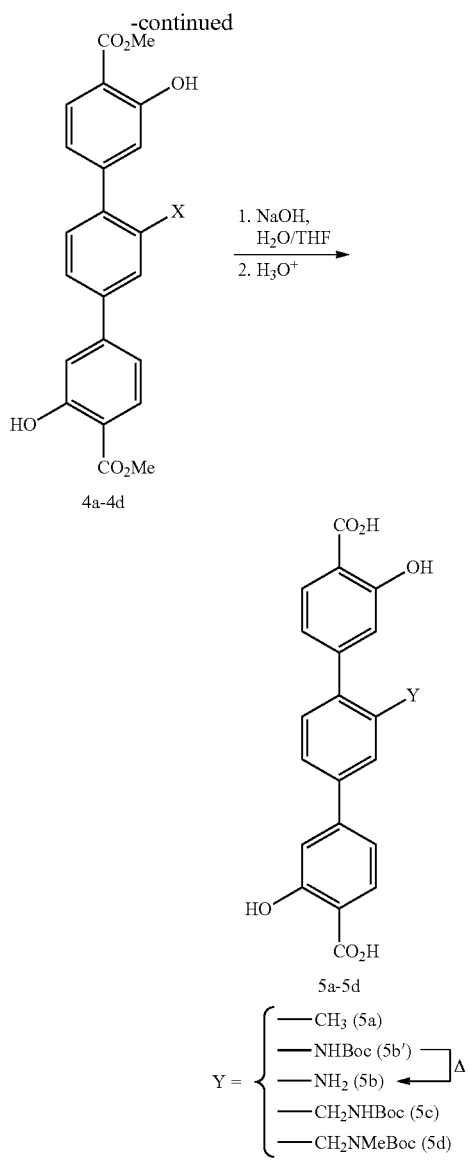

4a-4d

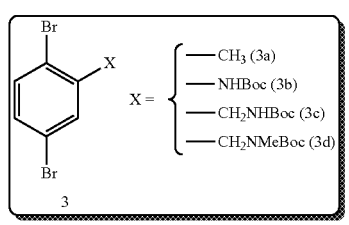

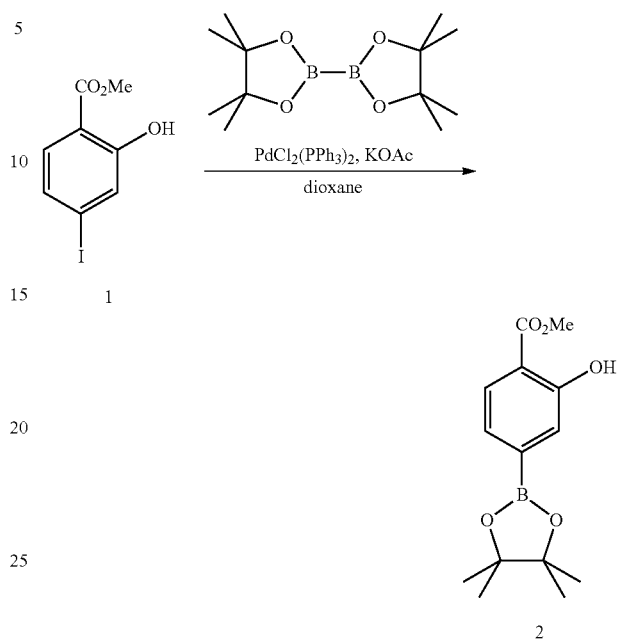

2

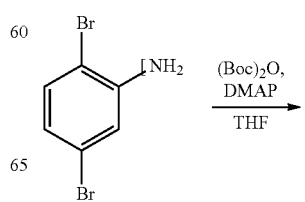

General procedure 2 (saponification). To a solution of the required ester (1.0 relative mol amount) in THF was added a solution of NaOH (10 relative mol amount) in H$_2$O to obtain a final concentration of 0.2 M for the ester (equal volumes of H$_2$O and THF). The resulting solution was stirred vigorously at 50° C. until the reaction completes (progress periodically checked by TLC). After cooled down to room temperature, THF was removed under vacuum to give typically slightly yellow solution. While being stirred, the aqueous layer was acidified with dilute HCl (1-3 M) and the resulting precipitate was collected by vacuum filtration, washed with ample H$_2$O, and dried in air for 24 h then in vacuo for 6 h to provide the corresponding hydrolysed product as typically a white powder.

Scheme 2: Synthetic path for 3-hydroxy-(methoxycarbonyl)phenylboronic acid pinacol ester (2):

Dioxane (450 mL) was added to a flask containing iodide 1 (25.0 g, 90.0 mmol), bis(pinacolato)diboron (25.1 g, 98.8 mmol), KOAc (29.1 g, 297 mmol), and PdCl$_2$(PPh$_3$)$_2$ (1.26 g, 1.80 mmol). The resulting suspension was deoxygenated by nitrogen bubbling at room temperature for 30 min, then immersed in oil bath preheated to 120° C., and stirred at reflux for 16 h. After cooled down to room temperature, the mixture was filtered to remove the insoluble material using AcOEt to rinse the filter cake. The filtrate was evaporated to give brown oil which solidified slowly at room temperature. The crude product was purified by flash silica gel column chromatography (hexanes/AcOEt, 10:1) followed by recrystallization from hot hexanes to provide compound 2 as colorless crystals (20.3 g, 73.1 mmol, 81%). $^1$H NMR (400 MHz, CDCl3), [ppm]: 1.34 (s, 12H), 3.94 (s, 3H), 7.27 (d, J=8.1 Hz, 1H), 7.41 (s, 1H), 7.80 (d, J=7.9 Hz, 1H), 10.6 (s, 1H); $^{13}$C{$^1$H}NMR (100 MHz, CDCl$_3$), [ppm]: 24.8, 52.3, 84.2, 114.2, 123.8, 124.7, 128.9, 160.7, 170.5; (Carbon directly bonded to boron was not observed). IR (ATR), v$^-$max [cm$^{-1}$]: 3177 (br), 2982 (w), 1676 (m), 1619 (w), 1557 (w), 1502 (w), 1438 (w), 1371 (sh), 1359 (s), 1329 (s), 1282 (m), 1220 (m), 1192 (m), 1169 (sh), 1136 (s), 1099 (s) 961 (w), 920 (m), 850 (m), 821 (w), 788 (s), 712 (s), 638 (m), 663 (m), 562 (m), 547 (m), 500 (w), 467 (w).

Scheme 3: Synthetic path for $^t$butyl-N-(2,5-dibromophenyl)carbamate (3b):

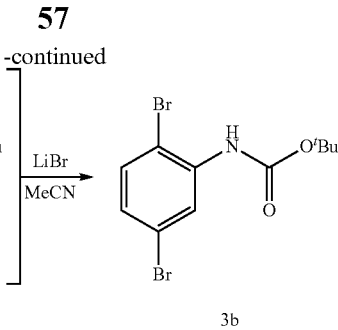

3b 2,5-Dibromoaniline (1.00 g, 3.99 mmol) was dissolved in THF (10 mL). After addition of di-tbutyl dicarbonate (2.60 g, 11.9 mmol) and 4-dimethylaminopyridine (49.1 mg, 0.402 mmol), the solution was stirred at 40° C. for 5 h. The reaction mixture was cooled down to room temperature and evaporated to dryness to give brown oil. Acetonitrile (40 mL) and LiBr (1.07 g, 12.3 mmol) were added to the oil, and the resulting suspension was stirred at 65° C. for 8 h before cooled down to room temperature then evaporated to dryness. The crude product was subjected to flash silica gel column chromatography (hexanes/AcOEt, 20:1) to provide compound 3b as a slightly yellow solid (1.24 g, 3.41 mmol, 85%). The material was subjected to the next step without further purification. $^1$H NMR (400 MHz, CDCl$_3$), [ppm]: 1.53 (s, 9H), 6.99 (br s, 1H), 7.10 (dd, J=8.5, 2.4 Hz, 1H), 7.33 (d, J=8.5 Hz, 1H), 8.39 (d, J=2.1 Hz, 1H); $^{13}$C{$^1$H} NMR (100 MHz, CDCl$_3$), [ppm]: 28.2, 81.6, 110.5, 122.0, 122.5, 126.6, 133.1, 137.4, 151.9.

Scheme 4. Synthesis path for tbutyl-2,5-dibromobenzylcarbamate (3c):

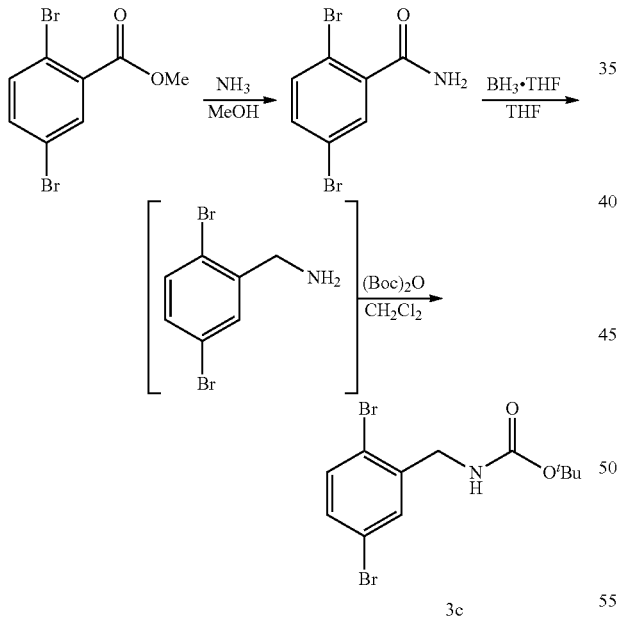

3c

Methyl 2,5-dibromobenzoate (10.1 g, 34.4 mmol) was dissolved in 7 M NH$_3$ solution in methanol (100 mL) in air. The resulting solution was evenly separated to ten 20-mL scintillation vials, and stirred at room temperature for 20 h with the caps tightly closed. The reaction mixtures were combined and filtered to collect the white precipitate, which was then dispersed in hexanes (200 mL), recollected by filtration, and dried in vacuo to give 2,5-dibromobenzamide (9.44 g, 33.8 mmol, 98%). $^1$H NMR (400 MHz, acetone-d6), [ppm]: 7.04 (br s, 1H), 7.34 (br s, 1H), 7.51 (dd, J=8.5, 2.4 Hz, 1H), 7.58 (d, J=8.5 Hz, 1H), 7.62 (d, J=2.4 Hz, 1H); $^{13}$C{$^1$H} NMR (100 MHz, acetone-d6), [ppm]: 118.8, 121.5, 132.4, 134.4, 135.8, 142.0, 168.2.

To a flask containing 2,5-dibromobenzamide (3.05 g, 10.9 mmol) was added 1 M BH$_3$ solution in THF (30 mL, 30 mmol), which was then stirred at reflux for 24 h before quenched by adding conc. HCl (3 mL). The solution was further refluxed for 2 h before cooled down to room temperature and basified to pH~10 by adding sat. Na$_2$CO$_3$. The reaction was partitioned between AcOEt (30 mL) and water (15 mL). The organic phase was isolated, and the aqueous phase was extracted with CH$_2$Cl$_2$ (3×30 mL). The combined organic phase was dried over Na$_2$SO$_4$, filtered, and evaporated to give a light yellow liquid. The liquid was dissolved in CH$_2$Cl$_2$ (15 mL), to which di-tbutyl dicarbonate (2.65 mL, 11.5 mmol) was added. The solution was stirred for 2.5 h at room temperature, before addition of ethanolamine (0.33 mL). After further stirring at room temperature for 1 h, the reaction mixture was partitioned between CH$_2$Cl$_2$ (15 mL) and water (15 mL). The organic phase was isolated and the aqueous phase was extracted with CH$_2$Cl$_2$ (3×15 mL). The combined organic layer was dried over Na$_2$SO$_4$, filtered, and evaporated to give light yellow oil, which was purified by flash silica gel column chromatography (CH$_2$Cl$_2$/hexanes/AcOEt, 20:30:1). Compound 3c was obtained as a white powder (2.55 g, 6.99 mmol, 64% from 2,5-dibromobenzoic acid). $^1$H NMR (400 MHz, CDCl$_3$), [ppm]: 1.46 (s, 9H), 4.33 (d, J=6.0 Hz, 2H), 5.06 (br s, 1H), 7.24 (dd, J=8.4, 2.2 Hz, 1H), 7.38 (d, J=8.4 Hz, 1H), 7.48 (d, J=2.3 Hz, 1H); $^{13}$C{$^1$H}NMR (100 MHz, CDCl$_3$), [ppm]: 28.3, 44.5, 80.0, 121.5, 121.8, 131.8, 132.1, 134.0, 140.0, 155.7; IR (ATR), v$^-$max [cm$^{-1}$]: 3344 (m), 3086 (w), 3065 (w), 3009 (w), 2979 (w), 2971 (w), 2938 (w), 1682 (s), 1514 (s), 1461 (m), 1428 (m), 1392 (m), 1365 (m), 1303 (m), 1273 (s), 1251 (s), 1234 (m), 1195 (m), 1159 (s), 1083 (m), 1041 (w), 1026 (s), 930 (m), 918 (m), 886 (m), 851 (m), 811 (s), 784 (m), 768 (m), 726 (w), 611 (m), 547 (w), 511 (m), 459 (m), 443 (s).

Scheme 5.
Synthesis path for $^t$butyl-2,5,dibromobenzyl (methyl) crbamate (3d):

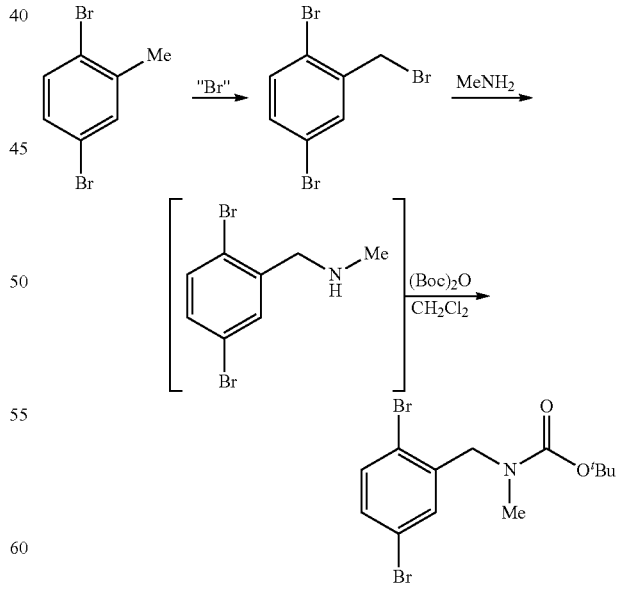

3d

N-Bromosuccinimide (1.78 g, 10.0 mmol) was added to a 200 mL two necked round bottom flask and the atmosphere was replaced from air to nitrogen. Anhydrous CH$_2$Cl$_2$ (80 mL) was then added to the flask and the solution was cooled to 0° C. Once the temperature was reached, ZrCl$_4$ (118 mg, 0.500 mmol) and 2,5-dibromotoluene (1.38 mL, 10.0 mmol) were added to the solution. The reaction was stirred 48 h from 0° C. to room temperature and then quenched by adding a saturated aqueous solution of NaHCO$_3$ (20 mL) The organic phase was separated and extracted with saturated aqueous NaCl solution (3×20 mL). The organic phase was dried over Na$_2$SO$_4$, filtered, and evaporated to give a brown/yellow liquid, which was purified by silica gel column chromatography (hexanes/CH$_2$Cl$_2$, 60:40). 2-(Bromomethyl)-1,4-dibromobenzene was obtained as a white powder (2.17 g, 6.60 mmol, 66% from 2,5-dibromotoluene). $^1$H NMR (400 MHz, CDCl$_3$), [ppm]: 4.53 (s, 2H), 7.29 (dd, J=8.5, 2.3 Hz, 1H), 7.43 (d, J=8.5 Hz, 1H), 7.59 (d, J=2.4 Hz, 1H). This intermediate was utilized in the next step without further purification.

To a 200 mL flask containing 2-(bromomethyl)-1,4-dibromobenzene (1.13 g, 3.40 mmol), were added 60 mL of THF and 1.8 mL of an aqueous methylamine solution (40 wt. %). The reaction was stirred at room temperature 18 h under nitrogen. The solvent was then removed under reduced pressure and the residue was partitioned in 110 mL of a mixture of CH$_2$Cl$_2$/15 wt. % NaHCO$_3$ in deionized water (60:50). The aqueous fraction was washed with CH$_2$Cl$_2$ (2×30 mL) and the organic fractions were collected, dried over anhydrous Na$_2$SO$_4$ and filtered. The solvent was evaporated under reduced pressure and the yellow oil was utilized in the next step without further purification.

The liquid was dissolved in CH$_2$Cl$_2$ (80 mL), to which di-tbutyl dicarbonate (1.48 mL, 6.42 mmol) was added. The solution was stirred for 18 h at room temperature and under nitrogen, before addition of ethanolamine (0.33 mL). After further stirring at room temperature for 3 h, the reaction mixture was partitioned between CH$_2$Cl$_2$ (15 mL) and water (15 mL). The organic phase was isolated and the aqueous phase was extracted with CH$_2$Cl$_2$ (3×15 mL). The combined organic layer was dried over Na$_2$SO$_4$, filtered, and evaporated to give light yellow oil, which was purified by flash silica gel column chromatography (CH$_2$Cl$_2$/AcOEt, 100:1). Compound 3d was obtained as a white powder (1.15 g, 3.00 mmol, 88% from 2-(bromomethyl)-1,4-dibromobenzene). $^1$H NMR (400 MHz, CDCl$_3$), [ppm]: 1.47 (d, J=34.4 Hz, 9H), 2.90 (d, J=20.1 Hz, 3H), 4.47 (d, J=50.3 Hz, 2H), 7.26 (m, 2H), 7.48 (d, J=8.3 Hz, 1H).

Scheme 6. Synthetic path for organic linker 5a:

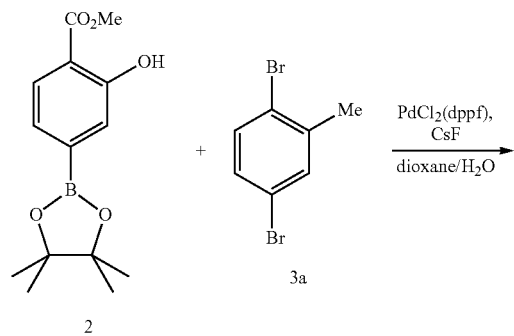

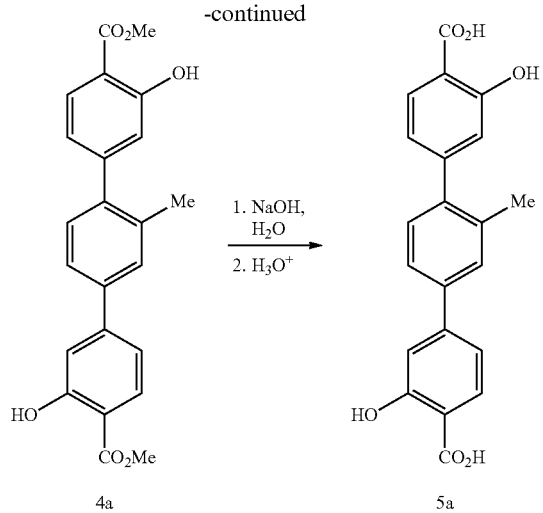

Boronate 2 (4.67 g, 16.8 mmol) and dibromide 3a (1.10 mL, 7.98 mmol) were subjected to Suzuki-Miyaura coupling. After cooling down to room temperature, the reaction mixture was partitioned between CH$_2$Cl$_2$ (300 mL) and 10% NH$_4$Cl (60 mL). The organic layer was isolated and the aqueous layer was extracted with CH$_2$Cl$_2$ (2×60 mL). The organic layers were combined, dried over Na$_2$SO$_4$, filtered, and evaporated in vacuo to provide a dark brown solid, which was then subjected to a filtration through a pad of silica gel (CH$_2$Cl$_2$). The filtrate was evaporated in vacuo and the resulting light yellow solid was recrystallized from hot toluene to provide 4a as white needles (2.72 g, 6.94 mmol, 87%). $^1$H NMR (500 MHz, CDCl$_3$), [ppm]: 2.35 (s, 3H), 3.98 and 3.99 (two s, 6H in total), 6.88 (dd, J=6.9, 1.4 Hz, 1H), 6.99 (d, J=1.3 Hz, 1H), 7.16 (dd, J=8.2, 1.5 Hz, 1H), 7.25 (d, J=1.4 Hz, 1H), 7.31 (d, J=7.8 Hz, 1H), 7.50 (d, J=7.9 Hz, 1H), 7.53 (s, 1H), 7.89 (d, J=7.9 Hz, 1H), 7.90 (d, J=8.1 Hz, 1H), 10.83 and 10.84 (two s, 2H in total); $^{13}$C{$^1$H} NMR (126 MHz, CDCl$_3$), [ppm]: 20.5, 52.3, 52.3, 111.1, 111.2, 115.7, 118.1, 118.1, 120.4, 124.7, 129.3, 129.7, 129.9, 130.3, 135.8, 139.2, 140.8, 148.0, 149.1, 161.3, 161.8, 170.5.

Compound 4a (2.43 g, 6.20 mmol) was hydrolyzed as described above using 3 M HCl for acidification to attain a pH<2. After drying, linker 5a was obtained as an off-white powder (2.08 g, 5.71 mmol, 92%). $^1$H NMR (400 MHz, DMSO-d6), [ppm]: 2.32 (s, 3H), 6.72-6.74 (overlapping s and dd, J=5.9, 1.5 Hz, 2H), 7.07-7.09 (two m, 2H), 7.27 (d, 7.9 Hz, 1H), 7.53 (dd, J=7.9, 1.4 Hz, 1H), 7.60 (s, 1H), 7.79-7.83 (two m, 2H); $^{13}$C{$^1$H} NMR (100 MHz, DMSO-d6), [ppm]: 20.3, 114.1, 115.8, 116.6, 116.9, 118.2, 124.3, 128.8, 129.8, 130.0, 130.7, 135.3, 138.7, 140.6, 144.3, 145.6, 161.9, 162.4, 171.9; IR (ATR), v$^-$max [cm$^{-1}$]: 3355 (br w), 3396 (br w), 3015 (w), 2944 (w), 2914 (w), 2859 (w), 1650 (m), 1621 (m), 1577 (s), 1515 (m), 1481 (m), 1435 (m), 1404 (m), 1358 (m), 1330 (m), 1291 (m), 1259 (m), 1206 (m), 1159 (m), 903 (m), 816 (m), 780 (s), 700 (m), 577 (m), 445 (w), 427 (w); MS (HR-ESI), m/z calcd. for C$_{21}$H$_{15}$O$_6$ [M-H]$^-$ 363.0869. found 363.0869.

Scheme 7. Synthetic path for organic linker 5b:

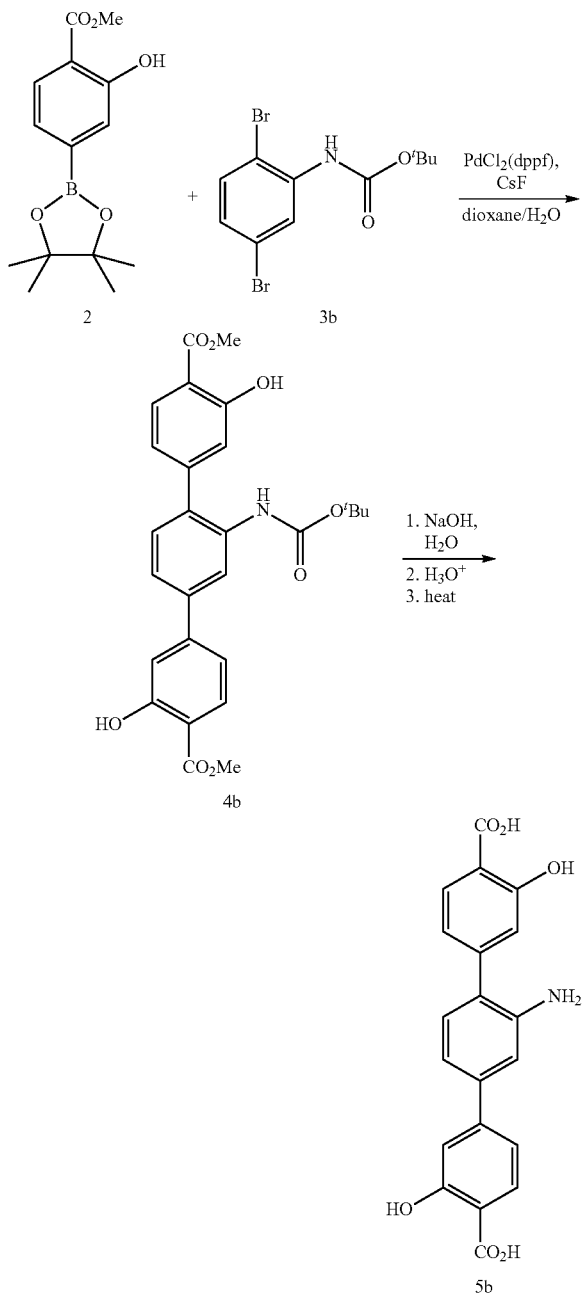

over a period of 40 min. Hexanes (10 mL) was added dropwise to form additional precipitate before the precipitate was collected by filtration then rinsed by toluene/hexanes (1:1, 40 mL) then hexanes (40 mL). The filtrate was evaporated and the resulting yellow solid was subjected to recrystallization in the same manner as above using 2 mL of toluene and 2 mL of hexanes. The first and second crops were combined and dried under vacuum to provide compound 4b as a white powder (1.04 g, 2.10 mmol, 82%). $^1$H NMR (500 MHz, CDCl$_3$), [ppm]: 1.48 (s, 9H), 3.97 and 3.98 (two s, 6H in total), 6.59 (s, 1H), 6.92 (dd, J=8.1, 1.5 Hz, 1H), 7.02 (d, J=1.4 Hz, 1H), 7.20 (dd, J=8.3, 1.6 Hz, 1H), 7.26 (d, J=8.0 Hz, 1H), 7.27 (d, J=1.5 Hz, 1H), 7.34 (dd, J=8.0, 1.6 Hz, 1H), 7.87 (d, J=8.2 Hz, 1H), 7.94 (d, J=8.1 Hz, 1H), 8.44 (s, 1H), 10.81 (s, 1H), 10.90 (s, 1H); $^{13}$C{$^1$H} NMR (126 MHz, CDCl$_3$), [ppm]: 28.2, 52.3, 52.4, 80.9, 111.3, 111.8, 115.8, 118.1, 118.3, 118.7, 120.0, 121.8, 130.0, 130.2, 130.2, 130.7, 135.6, 140.4, 145.5, 147.7, 152.6, 161.7, 161.9, 170.2, 170.4.

Compound 4b (0.485 g, 0.983 mmol) was hydrolyzed as described above using 1 M HCl for acidification to attain a pH6. After drying, the resulting white powder was heated under nitrogen at 180° C. for 2.5 h to remove tert-butyloxycarbonyl moieties to provide linker 5b as a yellow powder (0.248 mg, 0.679 mmol, 69%). $^1$H NMR (400 MHz, DMSO-d6), [ppm]: 6.98 (dd, J=8.0, 1.5 Hz, 1H), 7.03-7.05 (overlapping s and dd, 2H), 7.12-7.15 (overlapping peaks, 3H), 7.18 (dd, J=8.3, 1.6 Hz, 1H), 7.85 and 7.87 (two s, 2H); $^{13}$C{$^1$H} NMR (126 MHz, CDCl$_3$), [ppm]: 111.5, 111.9, 113.9, 114.4, 115.5, 116.7, 117.5, 119.7, 124.7, 130.6, 130.7, 130.8, 139.3, 145.6, 146.7, 147.4, 161.4, 161.4, 171.8, 171.8; IR (ATR), v$^-$max [cm$^{-1}$]: 3349 (br w), 2991 (br m), 2848 (br m), 2554 (br w), 1652 (s), 1616 (s), 1561 (m), 1483 (m), 1451 (s), 1433 (s), 1347 (m), 1259 (s), 1228 (s), 1201 (s), 1161 (s), 1100 (m), 1022 (w), 964 (m), 904 (m), 861 (m), 806 (w), 774 (s), 693 (m), 671 (m), 651 (w), 637 (w), 594 (w), 578 (w), 539 (w), 517 (w), 495 (w), 478 (w), 447 (w); MS (HR-ESI), m/z calcd. for C$_{20}$H$_{14}$NO$_6$ [M-H]$^-$ 364.0821. found 364.0822.

Scheme 8. Synthetic path for organic linker 5c:

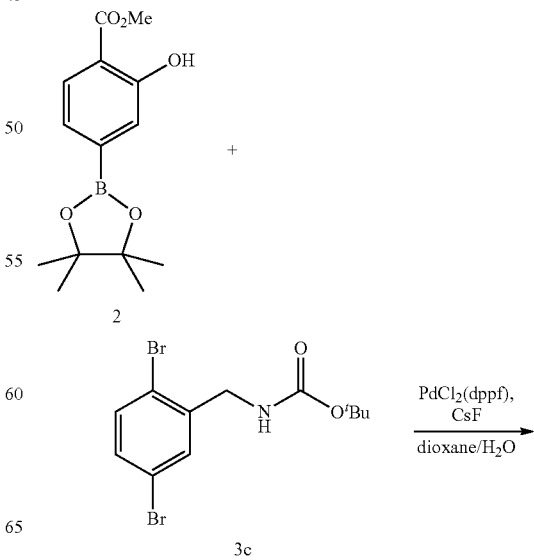

Boronate 2 (1.50 g, 5.39 mmol) and dibromide 3b (0.901 g, 2.57 mmol) were subjected to Suzuki-Miyaura coupling. After cooled down to room temperature, the reaction mixture was partitioned between AcOEt (100 mL) and 10% NH$_4$Cl (50 mL). The organic layer was isolated and the aqueous layer was extracted with AcOEt (3×50 mL). The organic layers were combined, washed with brine (50 mL), dried over Na$_2$SO$_4$, filtered, and evaporated in vacuo to provide a dark grey solid, which was then subjected to flash silica gel chromatography [CH$_2$Cl$_2$, then CH$_2$Cl$_2$/AcOEt (50:1)]. The fractions containing compound 4b were collected and evaporated in vacuo. The resulting light yellow solid was dissolved in hot toluene (10 mL) and the solution was cooled to room temperature to form white precipitates

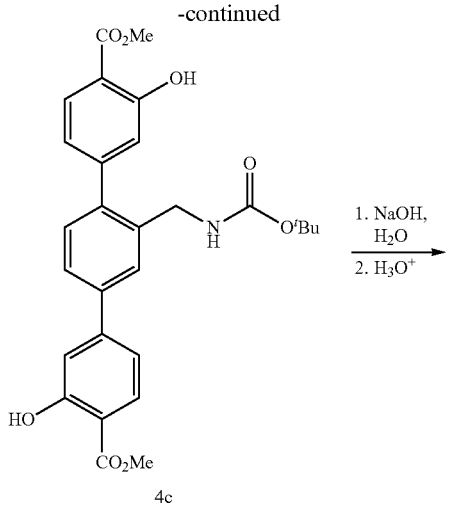

Boronate 2 (3.20 g, 11.5 mmol) and dibromide 3c (2.01 g, 5.51 mmol) were subjected to Suzuki-Miyaura coupling. After cooling to room temperature, the reaction mixture was partitioned between AcOEt (200 mL) and 10% NH$_4$Cl (50 mL). The organic layer was isolated and the aqueous layer was extracted with AcOEt (3×25 mL) The organic layers were combined, washed with brine (50 mL), dried over Na$_2$SO$_4$, filtered, and evaporated in vacuo to provide a black solid, which was then subjected to flash silica gel chromatography [CH$_2$Cl$_2$, then CH$_2$Cl$_2$/AcOEt (50:1)]. The fractions containing compound 4c were collected and evaporated in vacuo. The resulting light yellow solid was dissolved in toluene (20 mL), to which hexanes (20 mL) was added dropwise to form a white precipitate. The precipitate was collected by filtration, rinsed with toluene/hexanes (1:1, 10 mL), then dried in vacuo to provide pure 4c as a white powder (2.14 g, 4.21 mmol, 76%). $^1$H NMR (400 MHz, CDCl$_3$), [ppm]: 1.42 (s, 9H), 3.97 (s, 6H), 4.33 (d, J=3.5 Hz, 2H), 4.79 (s, 1H), 6.85 (d, J=7.8 Hz, 1H), 6.94 (s, 1H), 7.14 (d, J=7.9 Hz, 1H), 7.29 (s, 1H), 7.29 (d, J=7.7 Hz, 1H), 7.55 (d, J=7.3 Hz, 1H), 7.68 (s, 1H), 7.87-7.90 (two overlapping d, 2H), 10.82 and 10.84 (two s, 2H); $^{13}$C{$^1$H} NMR (100 MHz, CDCl$_3$), [ppm]: 28.3, 42.3, 52.3, 52.3, 79.6, 111.4, 111.4, 115.7, 117.9, 118.0, 120.2, 126.0, 127.0, 129.9, 130.2, 130.3, 136.6, 139.6, 140.2, 147.6, 147.9, 155.7, 161.4, 161.8, 170.3, 170.4.

Compound 4c (2.10 g, 4.15 mmol) was hydrolyzed as described above to provide linker 5c as an off-white powder (1.88 g, 3.92 mmol, 95%). $^1$H NMR (500 MHz, DMSO-d6), [ppm]: 1.20 and 1.37 (two s, 9H), 4.16 (d, J=5.9 Hz, 2H), 6.94 (d, J=8.3 Hz, 1H), 6.96 (s, 1H), 7.25 and 7.27 (overlapping s and d, 2H), 7.33 (d, J=8.0 Hz, 1H), 7.49 (t, J=5.9 Hz, 1H), 7.68 (d, J=7.9 Hz, 1H), 7.85 (d, J=8.0 Hz, 1H), 7.90 (d, J=8.7 Hz, 1H); $^{13}$C{$^1$H} NMR (126 MHz, DMSO-d6), [ppm]: 28.3, 41.3, 78.0, 112.1, 112.3, 114.7, 117.5, 117.6, 120.3, 125.4, 126.2, 130.1, 130.3, 131.1, 137.7, 138.3, 139.5, 146.7, 147.2, 155.8, 161.0, 161.6, 171.9; IR (ATR), v$^-$max [cm$^{-1}$]: 3400-2700 (br w), 2976 (w), 2931 (w), 2871 (w), 2567 (w), 1659 (s), 1619 (s), 1563 (m), 1500 (m), 1480 (m), 1454 (m), 1434 (m), 1394 (w), 1366 (m), 1340 (m), 1251 (s), 1202 (s), 1158 (s), 1097 (m), 1046 (w), 1027 (w), 905 (m), 875 (m), 844 (w), 816 (m), 778 (s), 692 (m), 595 (w), 569 (w), 510 (w), 456 (w); MS (HR-ESI), m/z calcd. for C$_{26}$H$_{24}$NO$_8$ [M-H]$^-$ 478.1502. found 478.1499.

Scheme 9. Synthetic path for organic linker 5d:

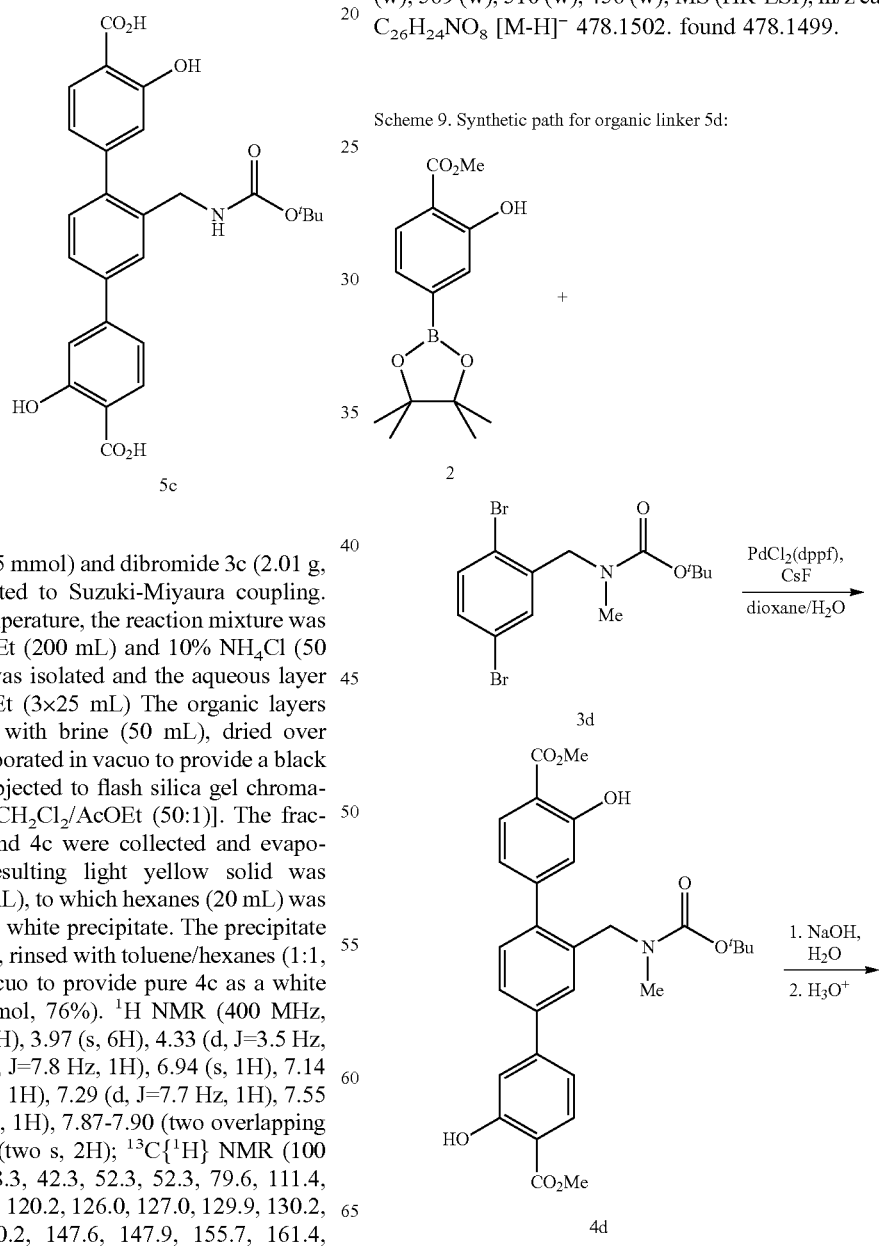

-continued

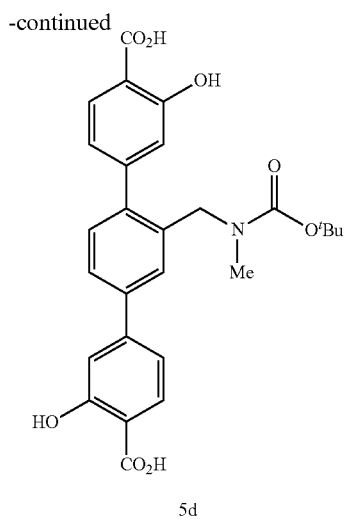

5d

Boronate 2 (1.2 g, 4.3 mmol) and dibromide 3d (0.80 g, 2.1 mmol) were subjected to Suzuki-Miyaura coupling. After cooling to room temperature, the reaction mixture was partitioned between $CH_2Cl_2$ (300 mL) and 10% $NH_4Cl$ (60 mL). The organic layer was isolated and the aqueous layer was extracted with $CH_2Cl_2$ (2×60 mL). The organic layers were combined, dried over $Na_2SO_4$, filtered, and evaporated in vacuo to provide a dark brown solid, which was then subjected to a filtration through a pad of silica gel ($CH_2Cl_2$). The filtrate was evaporated in $^{vacuo}$ and the resulting light yellow solid was subjected to flash silica gel chromatography [hexanes/AcOEt (90:10)]. Solvent evaporation in $^{vacuo}$ to provide pure 4d as a white powder (1.0 g, 1.9 mmol, 90%). $^1$H NMR (400 MHz, $CDCl_3$), [ppm]: 1.45 (d, J=19.7 Hz, 9H), 2.72 (d, J=29.3 Hz, 3H), 3.98 (s, 6H), 4.48 (d, J=24.4 Hz, 2H), 6.83 (d, J=6.9 Hz, 1H), 6.94 (s, 1H), 7.13 (d, J=8.0 Hz, 1H), 7.23, (s, 1H), 7.31 (d, J=7.9 Hz, 1H), 7.55 (m, 2H), 7.90 (m, 2H), 10.83 (s, 2H).

Compound 4d (0.98 g, 1.9 mmol) was hydrolyzed as described above. After drying, linker 5d was obtained as an off-white powder (0.83 g, 1.7 mmol, 90%). $^1$H NMR (400 MHz, $CDCl_3$), [ppm]: 1.31 (d, J=42.2, 9H), 2.65 (s, 3H), 4.44 (s, 2H), 6.90 (m, 2H), 7.23 (m, 2H), 7.35 (d, J=7.9 Hz, 1H), 7.52 (s, 1H), 7.70 (dd, J=7.9, 1.7 Hz, 1H), 7.87 (m, 2H); $^{13}C\{^1H\}$ NMR (126 MHz, $CDCl_3$), [ppm]: 27.90, 34.36, 54.90, 78.78, 112.16, 112.27, 114.63, 117.25, 117.51, 119.99, 125.68, 130.28, 131.04, 138.48, 146.54, 147.04, 160.90, 161.55, 171.72, 171.77. IR (ATR), v⁻max [cm⁻¹]: 3400-2700 (br w), 2986 (w), 2933 (w), 2857 (w), 2560 (w), 1657 (s), 1641 (s), 1564 (m), 1500 (m), 1482 (m), 1454 (s), 1420 (m), 1321 (m), 1315 (m), 1256 (s), 1210 (s), 1149 (s), 910 (m), 901 (m), 822 (m), 782 (s), 694 (m), 602 (w), 570 (w), 508 (m), 448 (w), 424 (w); MS (HR-ESI), m/z calcd. for $C_{27}H_{26}NO_8$ [M-H]⁻ 492.1658. found 492.1655.

Functionalized IRMOF-74-III Compounds were Prepared as Follows:

$Mg(NO_3)_2 \cdot 6H_2O$ (160 mg, 0.62 mmol) and the organic linker (0.188 mmol) were added into a 20-mL scintillation vials and dissolved with 15 mL of DMF. The vial was sonicated for 10 minutes and 1.0 mL of methanol followed by 1.0 mL of deionized water, were added to this solution. The vial was sonicated again for 10 minutes and the sealed vial with the resulting clear solutions, was placed into an isothermal oven at 120° C. for 20 h. After cooling down to room temperature, the solution was removed by syringe and the solid was immersed in 10 mL of DMF for 3 h. The liquid was then decanted and process repeated three times per day for 3 days. This whole protocol was repeated with methanol during 2 days to obtain the solid with washed interior. The solvent within the pores of the resulting solid was removed under dynamic vacuum initially at room temperature and then by heating at 120° C. for 8 h. The guest free samples were analyzed by PXRD and their surface area was determined by nitrogen adsorption experiments.

IRMOF-74-III-$CH_3$:

The synthesis was performed as above, yielding 90% of white crystals. PXRD was collected on activated sample (guest free). The high degree of correspondence between the sample pattern and that of the simulated model indicates that the bulk material has the same crystal structure as the predicted by simulation. To determine the presence of functional groups in the MOF pores, $^1$H NMR of digested samples was performed in 50 mM DCl in a DMSO-d6/D2O mixture.

IRMOF-74-III-$NH_2$:

Due to the lower solubility of the organic linker in comparison with other linkers reported here, the procedure for this MOF synthesis was slightly modified. $Mg(NO_3)_2 \cdot 6H_2O$ (160 mg, 0.62 mmol) and the organic linker 5b (68.7 mg, 0.188 mmol) were added into a 20-mL scintillation vials and dissolved with 15 mL of DMF. The vial was sonicated for 10 minutes and 2.5 mL of methanol followed by 2.5 mL of deionized water were added to this solution. The vial was sonicated again for 10 minutes and the sealed vial with the resulting clear solutions, was placed into an isothermal oven at 120° C. for 20 h. Yellow crystals were obtained in 84% reaction yield. PXRD was collected on activated sample (guest free). The high degree of correspondence between the sample pattern and that of the simulated model indicates that the bulk material has the same crystal structure as the predicted by simulation. To determine the presence of functional groups in the MOF pores, $^1$H NMR of digested samples was performed in 50 mM DCl in a DMSO-d6/D2O mixture. The absence of aliphatic signals and the correspondence of the aromatic proton integrals confirm the presence of —$NH_2$ functional group in the framework. IR (ATR), v⁻max [cm⁻¹]: 3330 (br w), 3027 (br w), 1608 (s), 1577 (s), 1524 (m), 1440 (s) 1418 (s), 1372 (m), 1219 (m) 930 (m), 793 (m), 709 (m), 610 (m).

IRMOF-74-III-$CH_2NHBoc$:

The synthesis was realized according to the general procedure above, yielding 81% of pale yellow crystals. PXRD was collected on activated sample (guest free). The high degree of correspondence between the sample pattern and that of the simulated model indicates that the bulk material has the same crystal structure as the predicted by simulation. To determine the presence of functional groups in the MOF pores, $^1$H NMR of digested samples was performed in 50 mM DCl in a DMSO-d6/D2O mixture. The resonance peaks at 1.35 ppm (d, 9H) and 4.14 ppm (s, 2H) corresponding to the Boc protecting group and benzyl amine (—$CH_2$—) respectively; confirm the presence of —$CH_2NHBoc$ functional group in the framework. IR (ATR), v⁻max [cm⁻¹]: 3360 (br w), 2979 (w), 1692 (s), 1585 (s), 1516 (m), 1433 (s) 1372 (s), 1250 (w), 1219 (m) 1159 (m), 1045 (w), 922 (m), 892 (w), 831 (m), 793 (m), 709 (m), 610 (m).

IRMOF-74-III-$CH_2NMeBoc$:

The synthesis was realized according to the general procedure above, yielding 81% of pale yellow crystals. PXRD was collected on activated sample (guest free). The high degree of correspondence between the sample pattern and that of the simulated model indicates that the bulk material has the same crystal structure as the predicted by simulation. To determine the presence of functional groups in the MOF pores, $^1$H NMR of digested samples was performed in 50 mM DCl in a DMSO-d6/D$_2$O mixture. The resonance peaks at 1.27 ppm (d, 9H), 2.63 ppm (s, 3H) and 4.42 ppm (s, 2H) corresponding to the Boc protecting group, N—CH$_3$ and benzyl amine —CH$_2$— respectively; confirm the presence of —CH$_2$NMeBoc functional group in the framework. IR (ATR), v$^-$max [cm$^{-1}$]: 3360 (br w), 2979 (m), 2926 (m), 1661 (m), 1600 (sh), 1577 (s), 1432 (s), 1402 (m) 1372 (m), 1257 (m), 1218 (m) 1151 (m), 967 (w), 930 (m), 876 (w), 830 (m), 792 (m), 709 (m), 571 (w).

The functionalized IRMOF-74-III crystals were subjected to solvent washing procedure. The compounds were transferred using a glass pipette into a 10 mL reaction tube containing 3 mL of 2-ethyl-1-hexanol, 150 μL of ethylene glycol and 150 μL of deionized water. The heterogeneous mixture was subjected to 230° C. microwave heating for 10 minutes. The mixture was allowed to cool down to room temperature and the DMF and methanol solvent washing procedure was repeated. The obtained microcrystalline samples were analyzed by PXRD and $^1$HNMR after digestion.

IRMOF-74-III-CH$_2$NH$_2$:

The Boc protecting group was removed by microwave heating. The yellow crystals of IRMOF-74-III-CH$_2$NH$_2$ were recovered in 98% reaction yield. PXRD was collected on activated sample (guest free). The high degree of correspondence between the sample pattern and that of the sample before the deprotection procedure indicates that the bulk material remains crystalline and with the same underlying topology after the post-synthetic deprotection. The successful Boc-deprotection was confirmed by the absence of the Boc resonance peak at 1.35 ppm in the $^1$H NMR of digested samples in 50 mM DCl in a DMSO-d6/D2O mixture. IR (ATR), v$^-$max [cm$^{-1}$]: 3024 (br w), 2940 (w), 1607 (sh), 1584 (s), 1516 (sh), 1440 (s) 1402 (sh), 1371 (s), 1325 (m), 1264 (w), 1219 (m), 1158 (w), 967 (w), 929 (m), 884 (w), 837 (m), 792 (m), 708 (m), 610 (m), 571 (w).

IRMOF-74-III-CH$_2$NHMe:

The Boc group was removed by microwave heating. The strong yellow crystals of IRMOF-74-III-CH$_2$NHMe were recovered in 94% reaction yield. PXRD was collected on activated sample (guest free). The high degree of correspondence between the sample pattern and that of the sample before the deprotection procedure indicates that the bulk material remains crystalline and with the same underlying topology after the post-synthetic deprotection. The successful Boc-deprotection was confirmed by the absence of the Boc resonance peak at 1.27 ppm in the $^1$H NMR of digested samples in 50 mM DCl in a DMSO-d6/D2O mixture. IR (ATR), v$^-$max [cm$^{-1}$]: 3064 (br w), 1608 (m), 1585 (s), 1524 (sh), 1440 (s) 1410 (m), 1372 (m), 1326 (w), 1257 (w), 1219 (m), 1151 (w), 978 (w), 922 (m), 884 (w), 831 (m), 793 (m), 709 (m), 610 (m), 572 (w).

Figure 18:
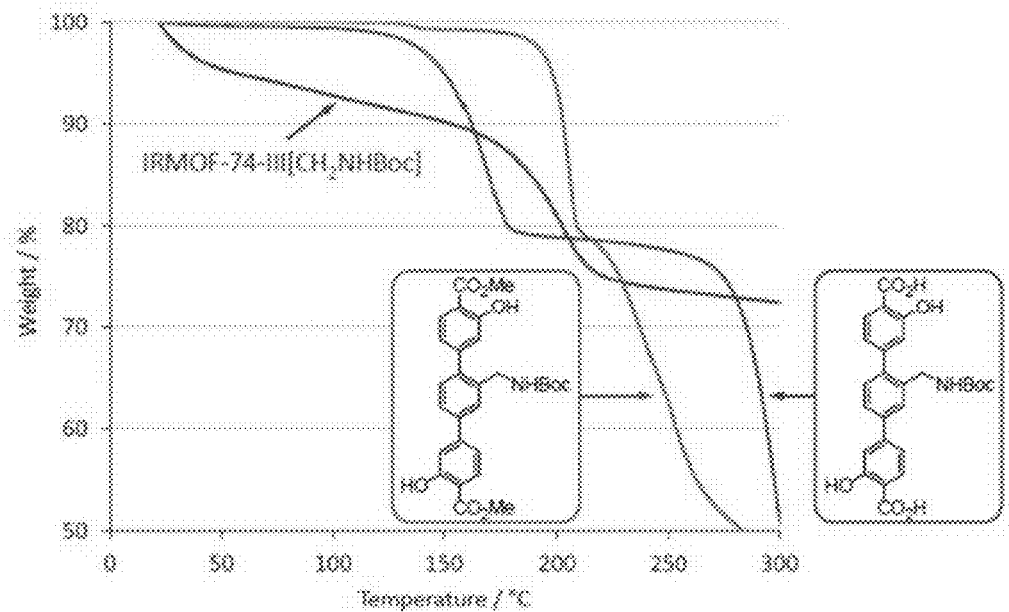
FIG. 18 provides thermogravimetric analysis (TGA) data for IRMOF-74-III[CH$_2$NHBoc] indicating that a higher temperature is required for deprotection.
Figure 19:
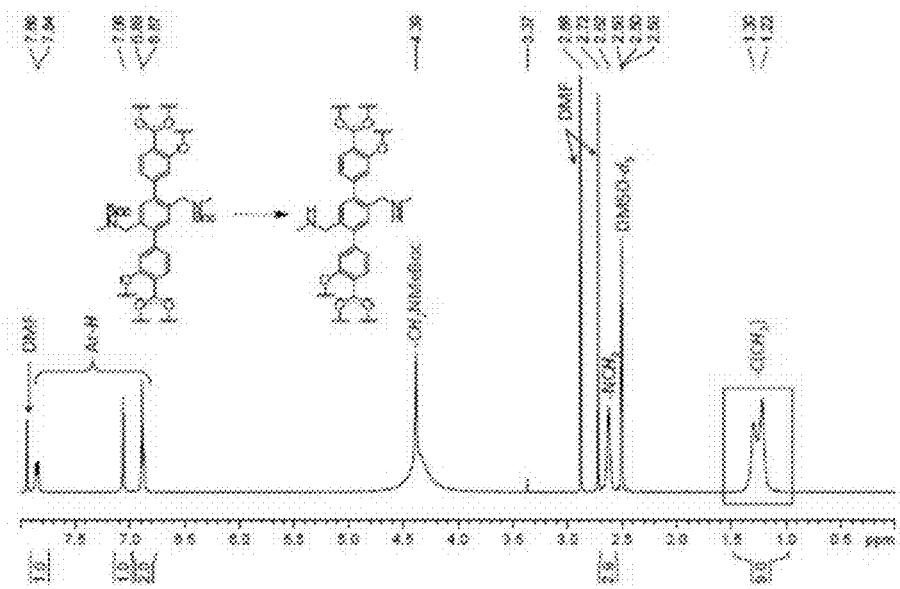
FIG. 19 presents an $^1$H NMR spectrum of digested IRMOF-74-III[(CH$_2$NHMeBoc)$_2$] at 400 MHz, using DMSO-d$_6$+DCl/D$_2$O. The NMR spectrum indicates the peak location for a Boc protected N-linked group and a peak indicating the Boc group's removal from the N-linked group.
Figure 20:
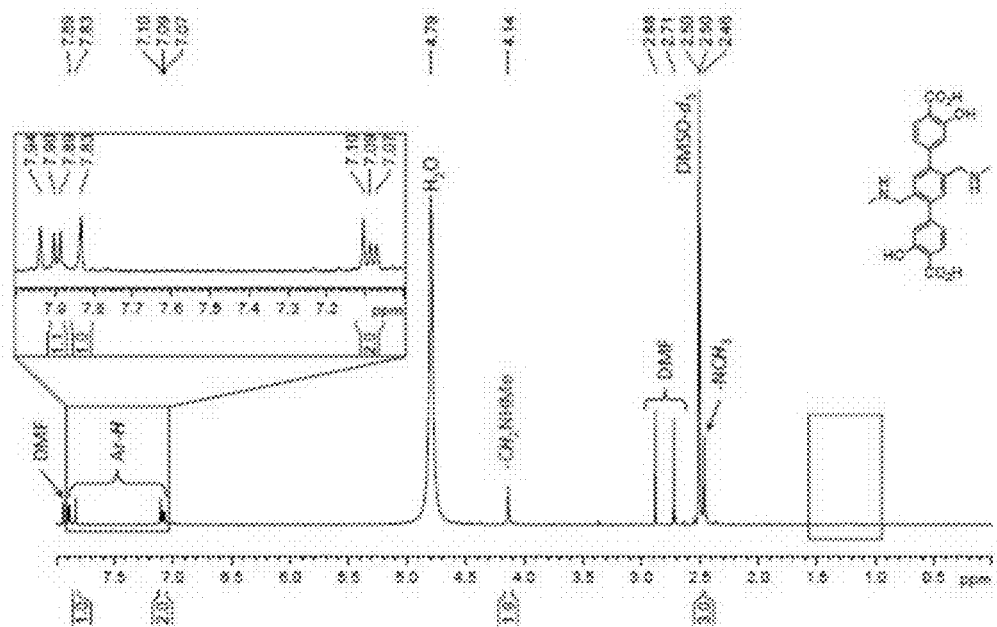
FIG. 20 presents an $^1$H NMR spectrum of deprotected IRMOF-74-III[(CH$_2$NHMeBoc)$_2$] at 500 MHz, using DMSO-d$_6$+DCl/D$_2$O. The NMR spectrum indicates the complete, clean removal of Boc groups was achieved by µ-wave heating at 230° C. in DMF.
Figure 21:
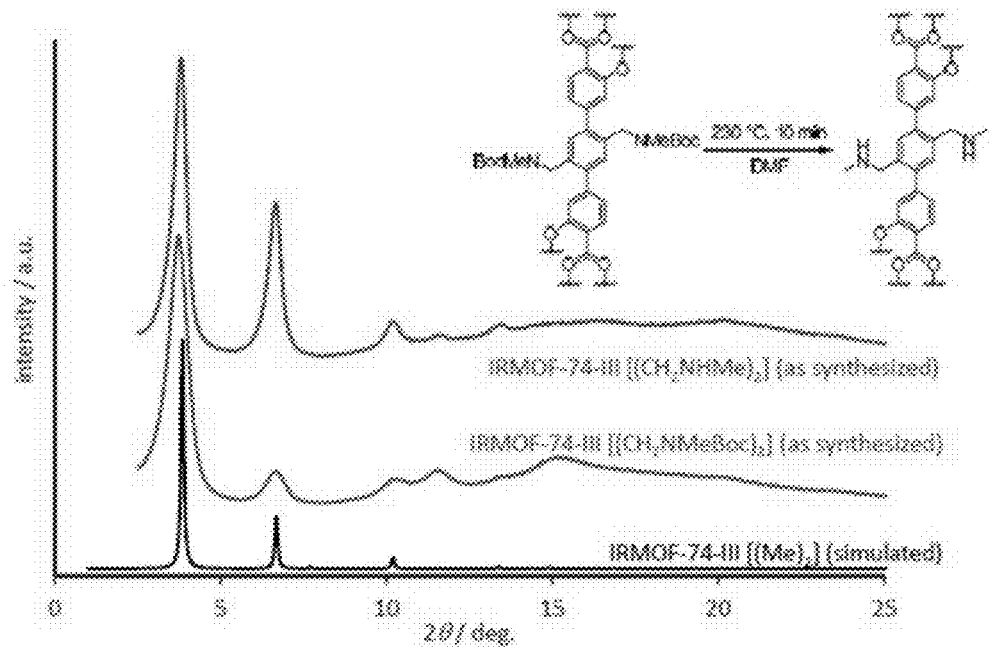
FIG. 21 provides PXRD tracings indicating that the deprotection of IRMOF-74-III[(CH$_2$NHMe)$_2$] in DMF at 230° C. for 10 minutes provides a still crystalline deprotected IRMOF-74-III[(CH$_2$NHMe)$_2$].
Figure 22:
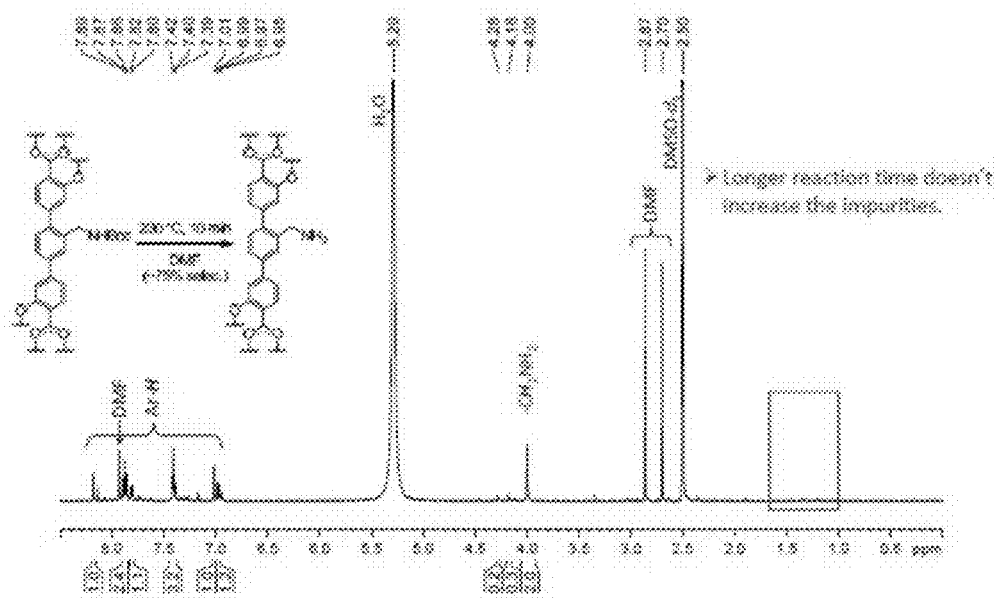
FIG. 22 presents an $^1$H NMR spectrum of digested IRMOF-74-III[CH$_2$NHBoc] at 500 MHz, using DMSO-d$_6$+DCl/D$_2$O. The NMR indicates that the removal of the BOC group of IRMOF-74-III[CH$_2$NHBoc] using DMF at 230° C. for 10 minutes is less effective than the deprotection of the Boc groups for IRMOF-74-III[(CH$_2$NHBoc)$_2$].
Figure 23:
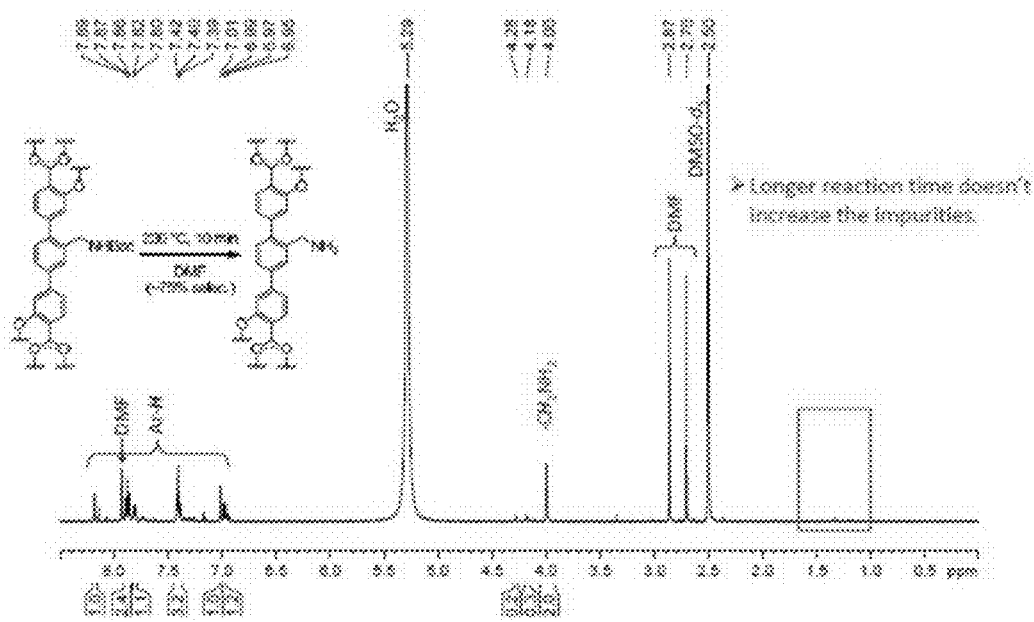
FIG. 23 presents an $^1$H NMR spectrum of digested IRMOF-74-III[CH$_2$NH$_2$] at 400 MHz, using DMSO-d$_6$+DCl/D$_2$O. The NMR indicates that a 2-ethyl-1-hexanol/ethylene glycol/water mixed solvent system allows for complete removal of the Boc protecting group.
Figure 24:
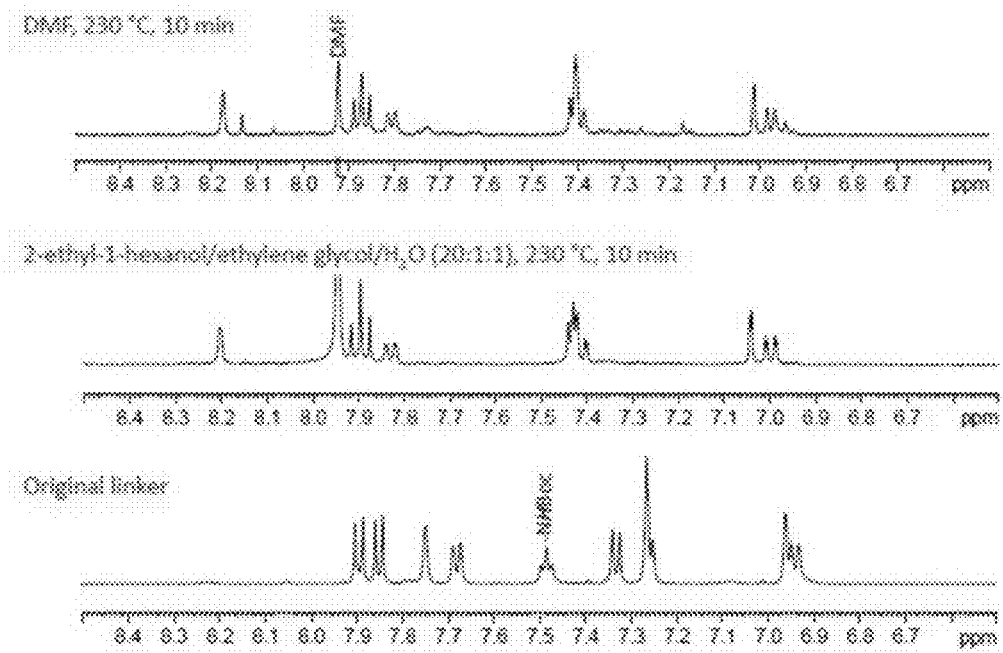
FIG. 24 presents an $^1$H NMR spectrum demonstrating the clean deprotection of the Boc protecting group of IRMOF-74-III[CH$_2$NHBoc](DMSO-d$_6$+DCl/D$_2$O) using 2-ethyl-1-hexanol/ethylene glycol/water mixed-solvent system at 230° C. for 10 minutes.
Figure 25:
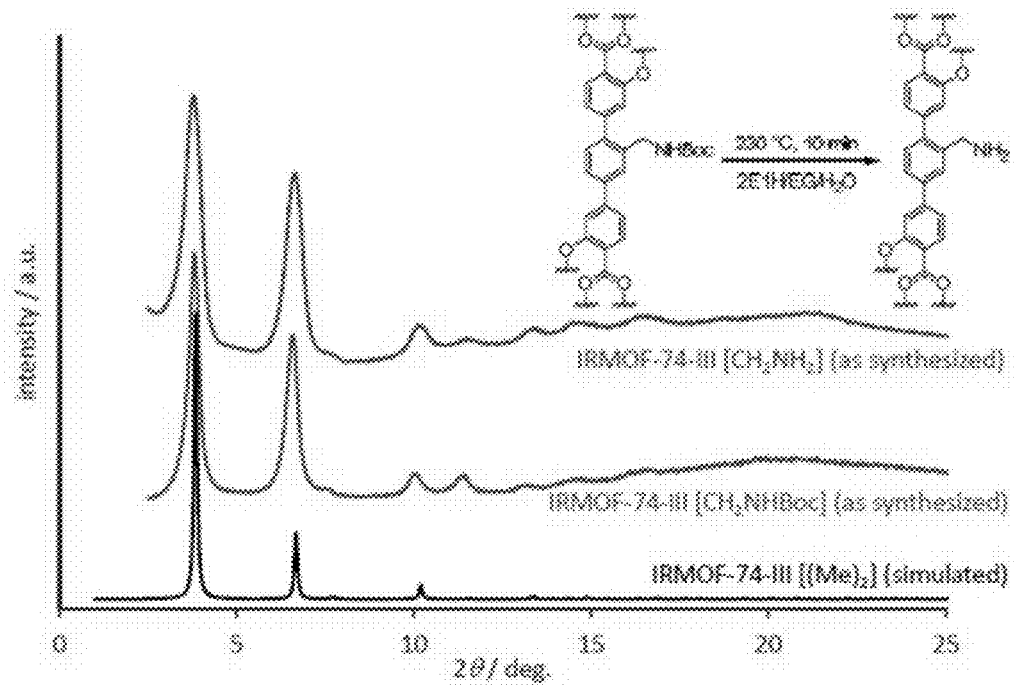
FIG. 25 provides PXRD tracings indicating that the IRMOF-74-III frameworks are still crystalline post deprotection using a 2-ethyl-1-hexanol/ethylene glycol/water mixed-solvent system at 230° C. for 10 minutes.
Figure 26:
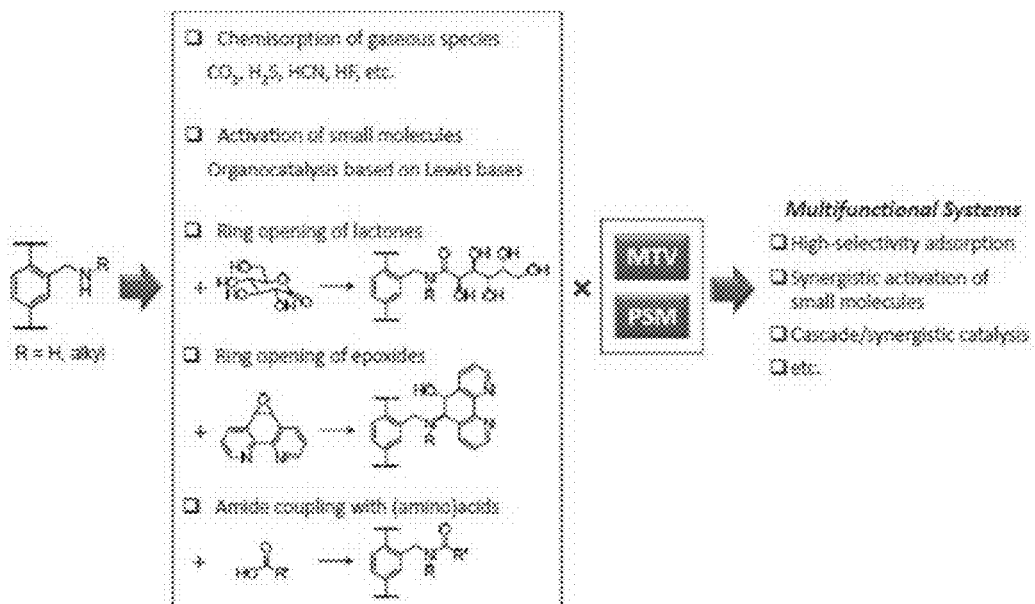
FIG. 26 demonstrates the scope of the alkylamine functionality and examples of reactions that can lead to additional multifunctional framework systems.
Figure 27:
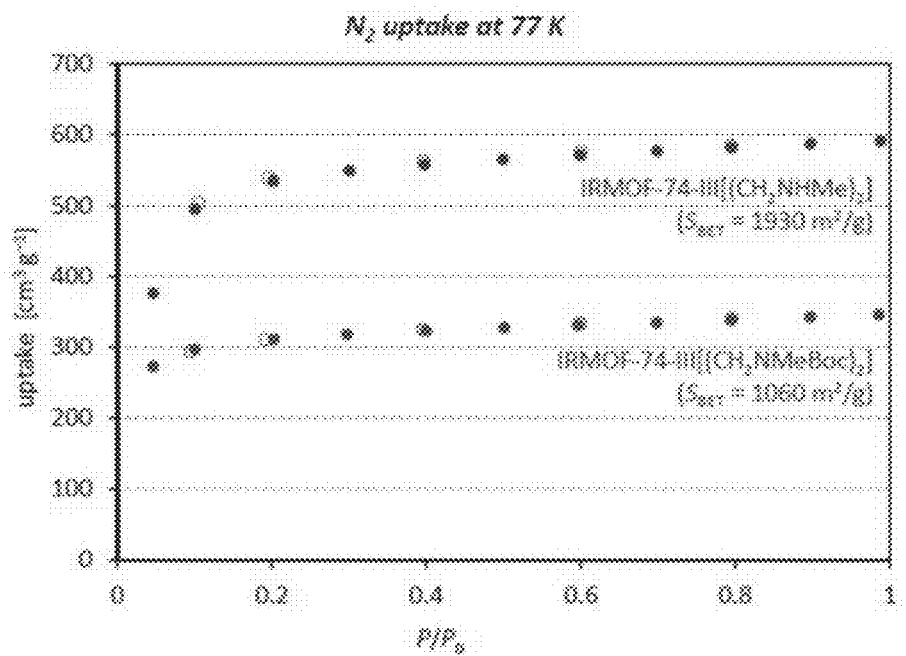
FIG. 27 presents an N$_2$-isotherm at 77K demonstrating reasonable N$_2$ uptake by IRMOF-74-III[(CH$_2$NHMe)$_2$)]. Activation procedure: was with DMF, solvent exchange to MeOH, and evacuate at room temperature for 12 hour and then 100° C. for 12 hours.
Figure 28:
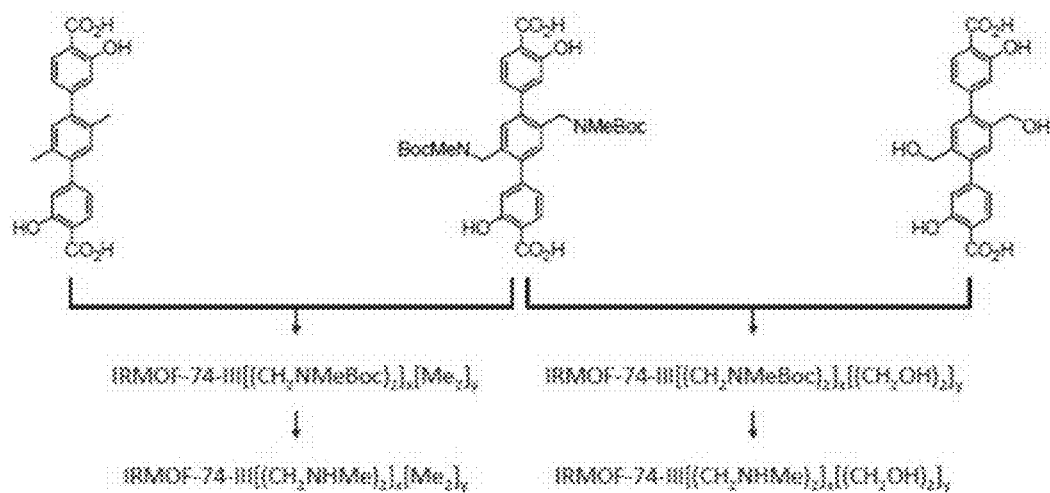
FIG. 28 presents that N-Boc deprotection was successful for mixed linker systems.
Figure 29:
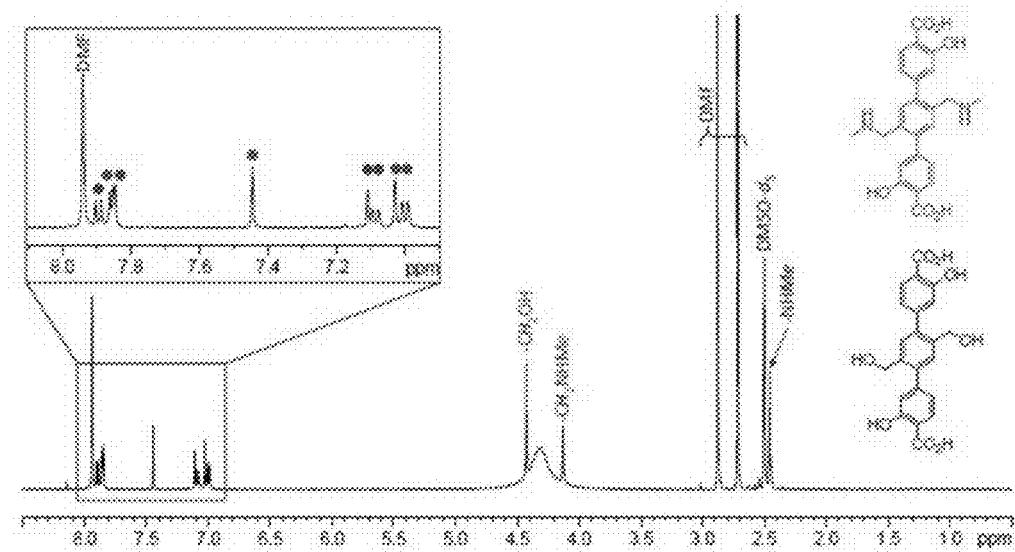
FIG. 29 presents an $^1$H NMR spectrum of IRMOF-74-III [(CH$_2$NHMe)$_2$][(CH$_2$OH)$_2$] at 500 MHz, using DMSO-d$_6$+DCl/D$_2$O. The NMR indicates the clean removal of the Boc protecting groups.

Additional MOFs of the disclosure were synthesized by following the reaction schemes presented in FIGS. 7, 10, 11, and 17. These MOFs as well as other MOFs of the disclosure (e.g., see FIG. 8(A) and FIG. 9) were characterized by NMR (e.g., see FIGS. 13-16, 19, 20, 22-24 and 29), by PXRD (e.g., see FIG. 8(B), 12, 21 and 25) by TGA (e.g., FIG. 18) or by isotherms with N$_2$ (e.g., FIG. 27).

Nitrogen Adsorption Measurements.

Figure 30:
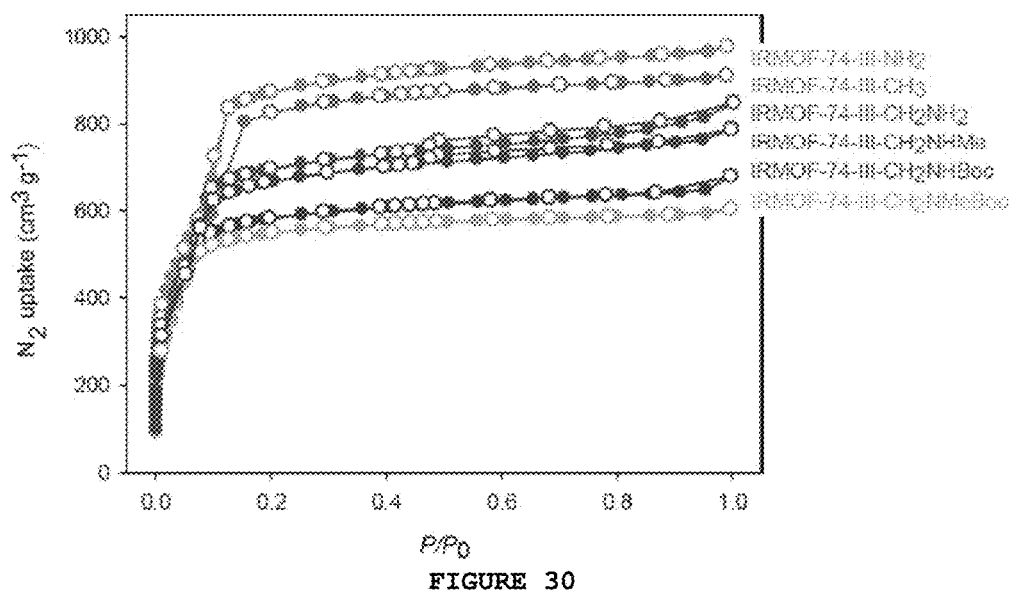
FIG. 30 shows nitrogen adsorption isotherms for functionalized IRMOF-74-III measured at 77 K. IRMOF-74-III-CH$_3$, IRMOF-74-III-NH$_2$, IRMOF-74-III-CH$_2$NHBoc, IRMOF-74-III-CH$_2$NH$_2$, IRMOF-74-III-CH$_2$NMeBoc, and IRMOF-74-III-CH$_2$NHMe.

BET surface area reflects the geometrical surface of MOF materials; therefore, bulky functionalities may create more accessible surface. FIG. 30 shows nitrogen absorption isotherms for functionalized IRMOF-74s of the disclosure.

TABLE 3

Summary of pore volumes and surface areas for IFMOF-74-IIIs of the disclosure:

| IRMOF-74-III | Pore Volume (cm$^3$ g$^{-1}$) | BET (m$^2$ g$^{-1}$) | Langmuir (m$^2$ g$^{-1}$) |
|---|---|---|---|
| —CH$_3$ | 1.37 | 2640 | 3940 |
| —NH$_2$ | 1.44 | 2720 | 4130 |
| —CH$_2$NHBoc | 0.95 | 2170 | 2720 |
| —CH$_2$NH$_2$ | 1.14 | 2310 | 3270 |
| —CH$_2$NMeBoc | 0.89 | 2220 | 2540 |
| —CH$_2$NHMe | 1.13 | 2250 | 3150 |

Carbon Dioxide Uptake Capacities.

To prepare guest free form of IRMOF-74-III-CH$_2$NH$_2$, the same (and modified) activation procedures of IRMOF-74-III-CH$_3$ were used. However, digestion NMR spectra of activated IRMOF-74-III-CH$_2$NH$_2$ showed presence of small amounts of solvent molecules (larger amount of water compared to the Boc protected compounds, presumably due to the use of water as solvent for the Boc deprotection procedure). This observation implies that these solvent molecules remained in the MOF even after the activation procedure. Due to the employed activation conditions (120° C. and vacuum) it is reasonable to think that the solvent molecules were occupying strong binding sites in the MOF, such as metal coordination sites. Therefore, unlike in IRMOF-74-III-CH$_3$, open magnesium sites are not available in IRMOF-74-III-CH$_2$NH$_2$. This explains why IRMOF-74-III-CH$_2$NH$_2$ did not show a significant improvement compared to IRMOF-74-III-CH$_3$ at 760 Torr, even when new chemisorption sites were created by the introduction of amine functionalities in IRMOF-74-III-CH$_3$.

The total carbon dioxide uptake should be the sum of the uptake at the open magnesium sites and at the chemisorptions sites. If all open metal sites in IRMOF-74-III-CH$_3$ are fully occupied by carbon dioxide at 760 Torr and 25° C., expected uptake based only on the magnesium sites is ca. 100 cm$^3$ g$^{-1}$. Similarly if all amine functionalities in IRMOF-74-III-CH$_2$NH$_2$ form carbamates, expected carbon dioxide uptake based only on the chemisorption sites is ca. 50 cm$^3$ g$^{-1}$.

TABLE 4

Carbon Dioxide uptake capacities of 800 Torr and 25° C. for the IRMOF-74-IIIs of the disclosure:

| IRMOF-74-III | CO$_2$ uptake (cm$^3$ g$^{-1}$) | CO$_2$ uptake (mol f.n.$^{-1}$)* |
|---|---|---|
| —CH$_3$ | 66.1 | 1.2 |
| —NH$_2$ | 71.0 | 1.3 |
| —CH$_2$NHBoc | 46.7 | 1.1 |
| —CH$_2$NH$_2$ | 73.2 | 1.4 |
| —CH$_2$NMeBoc | 42.7 | 1.0 |
| —CH$_2$NHMe | 63.9 | 1.2 |

A number of embodiments have been described herein. Nevertheless, it will be understood that various modifications may be made without departing from the spirit and scope of this disclosure. Accordingly, other embodiments are within the scope of the following claims.

What is claimed is:

1. A Metal-Organic Framework (MOF) comprising a plurality of secondary building units (SBUs) that are linked together by a plurality of organic linking ligands, the MOF selected from the group consisting of:
(a) a plurality of different SBUs, at least two SBUs of the plurality of SBUs comprising different metals or metal ions and a plurality of homogenous organic linking ligands that have been alkyl or amine functionalized; and
(b) a plurality of SBUs and a plurality of organic linking ligands wherein at least two of the organic linking ligands comprise a different number or a different type of functional group(s), wherein the plurality of organic linking ligands comprise a structure of Formula I and/or II:

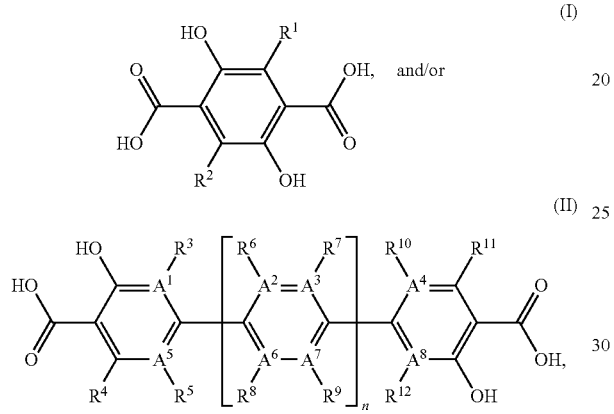

wherein, n is a number from 0 to 10;

$A^1$-$A^8$ are independently a C or N;

$R^1$-$R^{12}$ are independently selected from H, D, optionally substituted ($C_1$-$C_{12}$)alkyl, optionally substituted hetero-($C_1$-$C_{12}$ alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, optionally substituted ($C_1$-$C_{12}$)cycloalkyl, optionally substituted ($C_1$-$C_{12}$)cycloalkenyl, optionally substituted aryl, optionally substituted heterocycle, optionally substituted mixed ring system, —C($R^{13}$)$_3$, —CH($R^{13}$)$_2$, —CH$_2$$R^{13}$, —C($R^{14}$)$_3$, —CH($R^{14}$)$_2$, —CH$_2$$R^{14}$, —OC($R^{13}$)$_3$, OCH($R^{13}$)$_2$, —OCH$_2$$R^{13}$, —OC($R^{14}$)$_3$, —OCH($R^{14}$)$_2$, OCH$_2$$R^{14}$, wherein $R^4$-$R^{11}$ when adjacent can be linked together to form one or more optionally substituted rings selected from the group consisting of cycloalkyl, cycloalkenyl, heterocycle, aryl, and mixed ring system;

$R^{13}$ is selected from optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$) alkynyl, optionally substituted hetero-($C_1$-$C_{12}$)alkynyl, hemiacetal, hemiketal, acetal, ketal, and orthoester; and $R^{14}$ is selected from one or more substituted or unsubstituted rings selected from cycloalkyl, aryl and heterocycle.

2. The MOF of claim 1, wherein the plurality of organic linking ligands comprise a structure of Formula III:

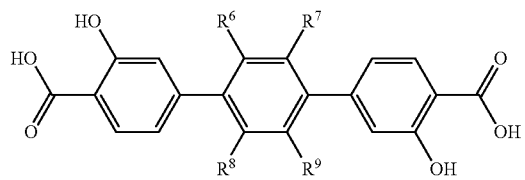

wherein, $R^6$-$R^9$ are independently selected from:

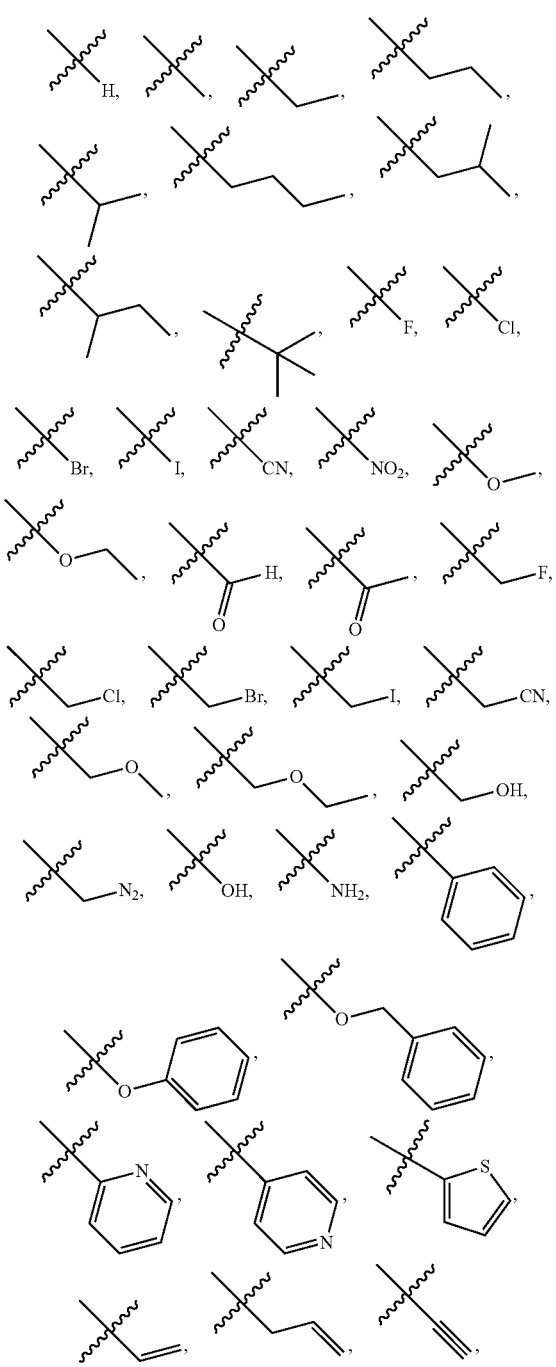

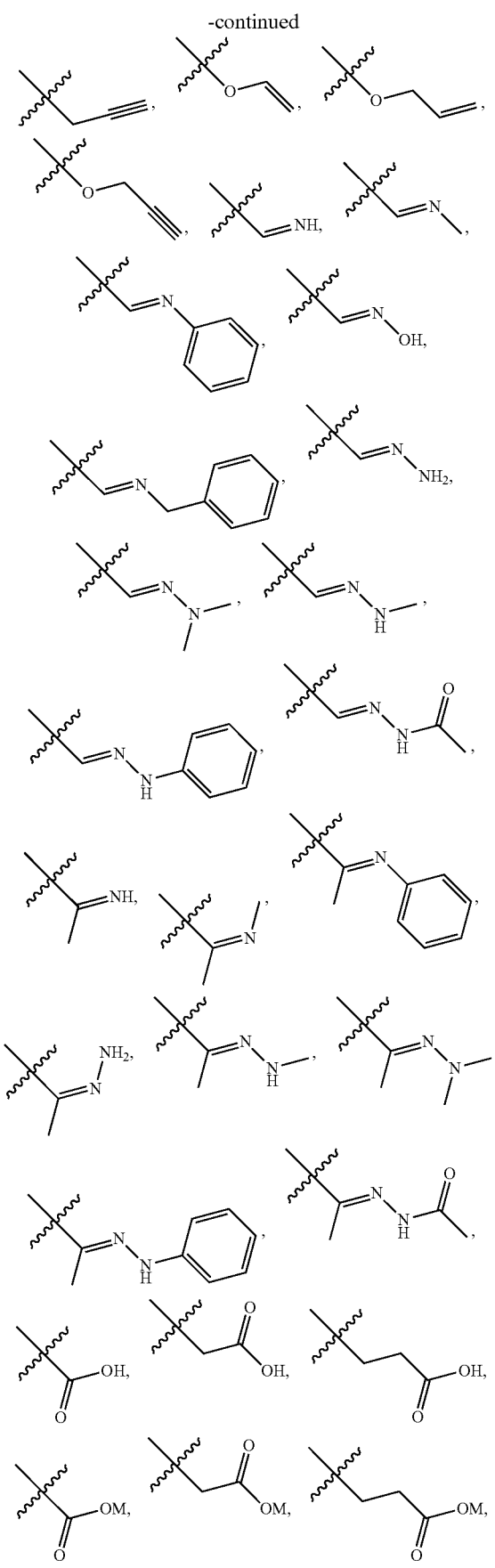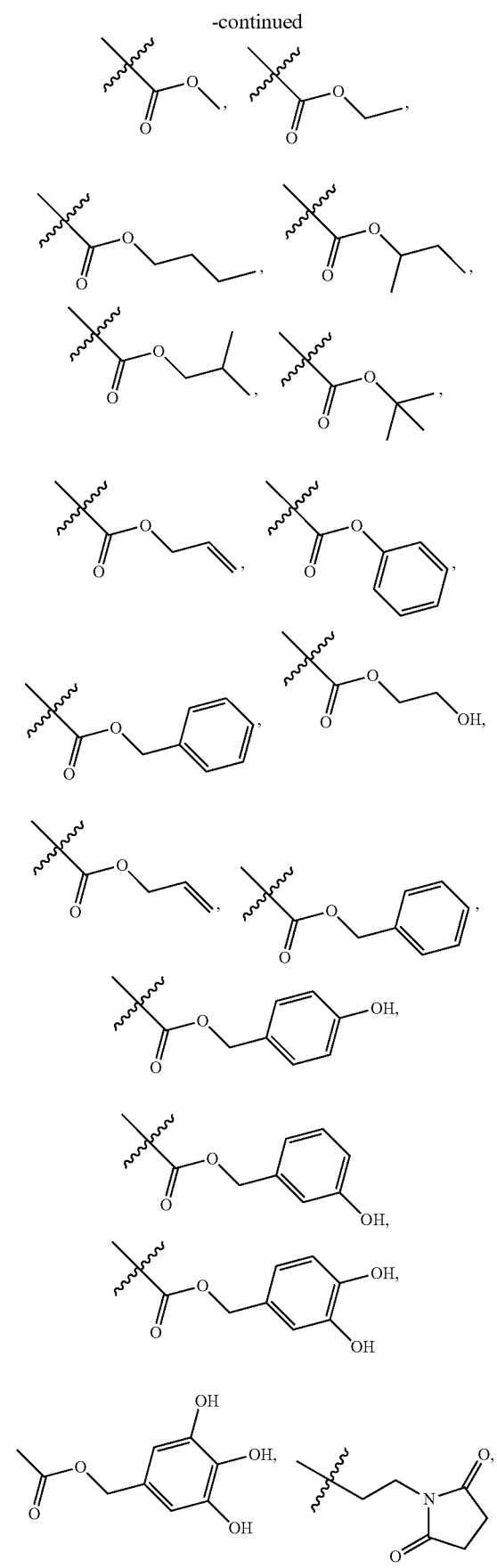

73
-continued
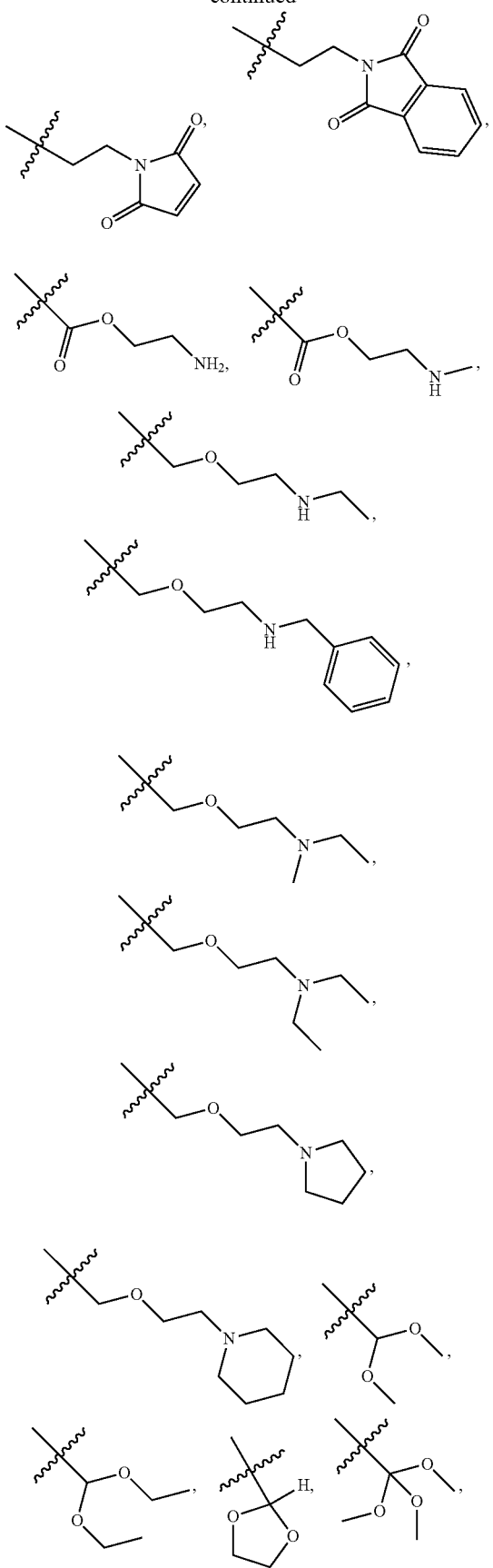
74
-continued
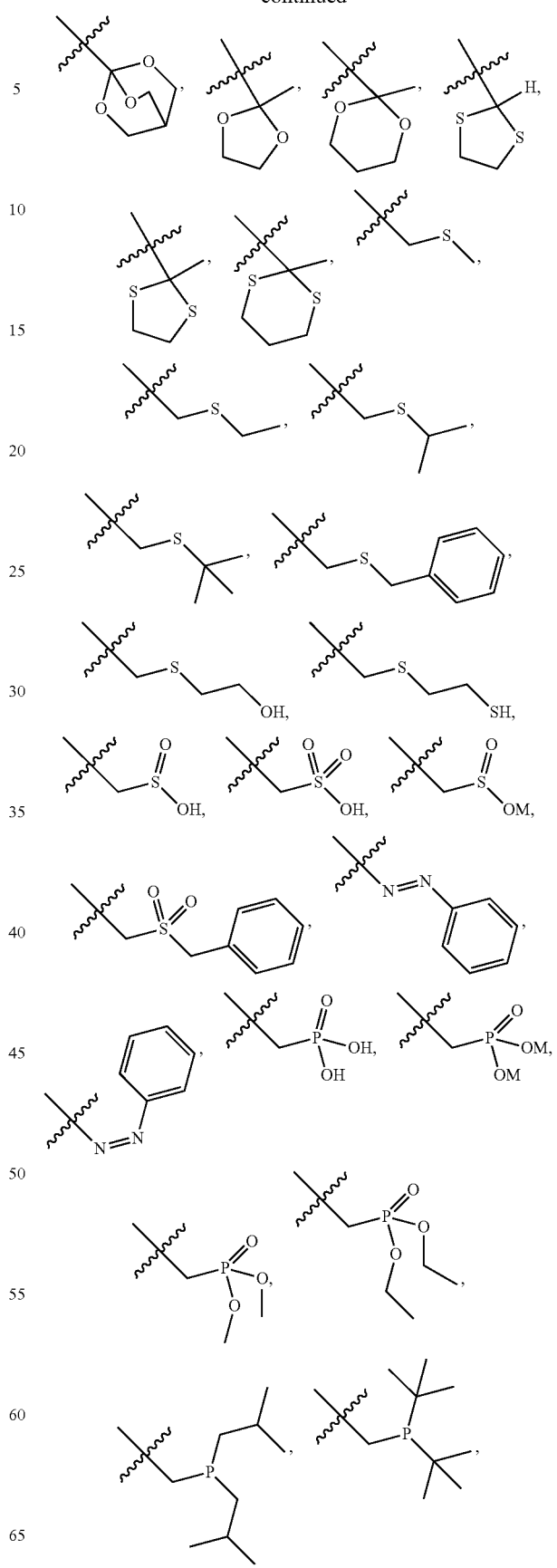

-continued
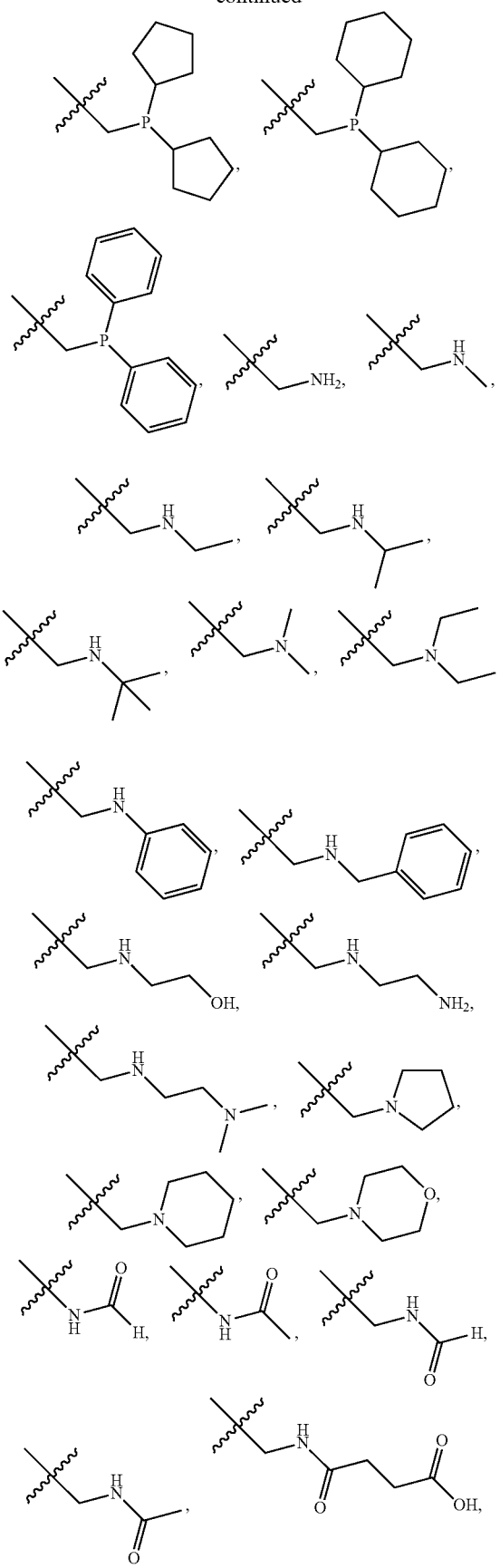
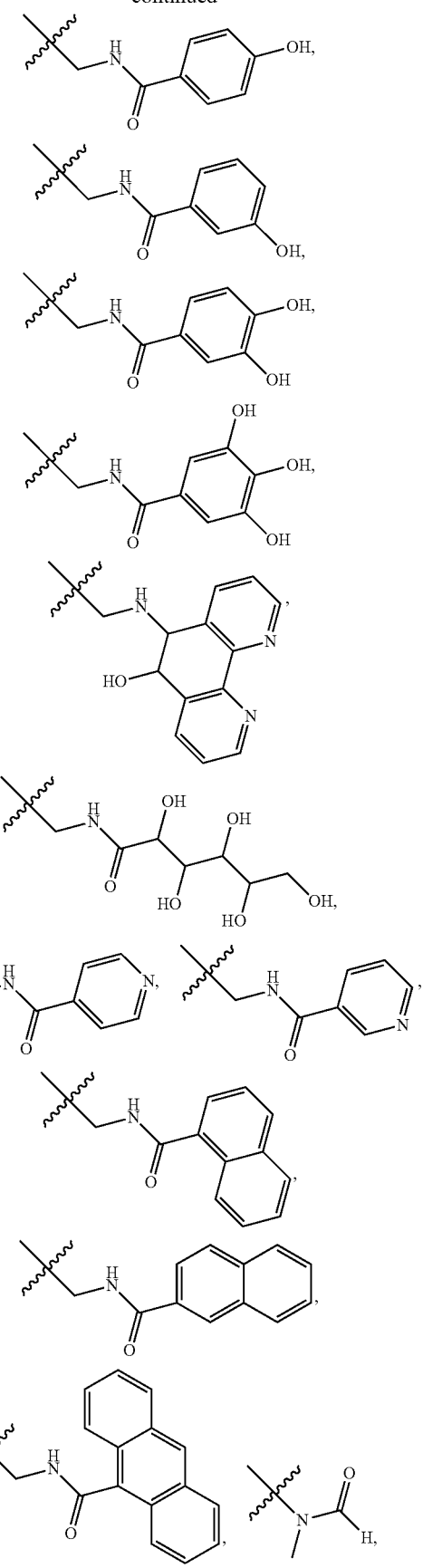

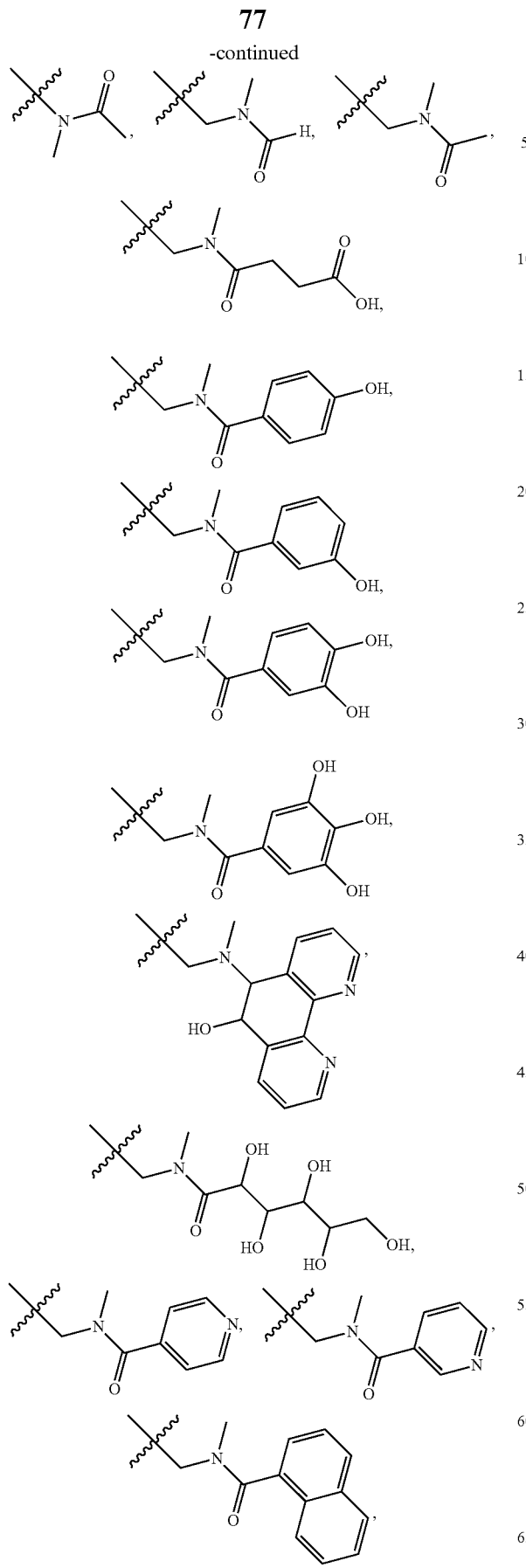
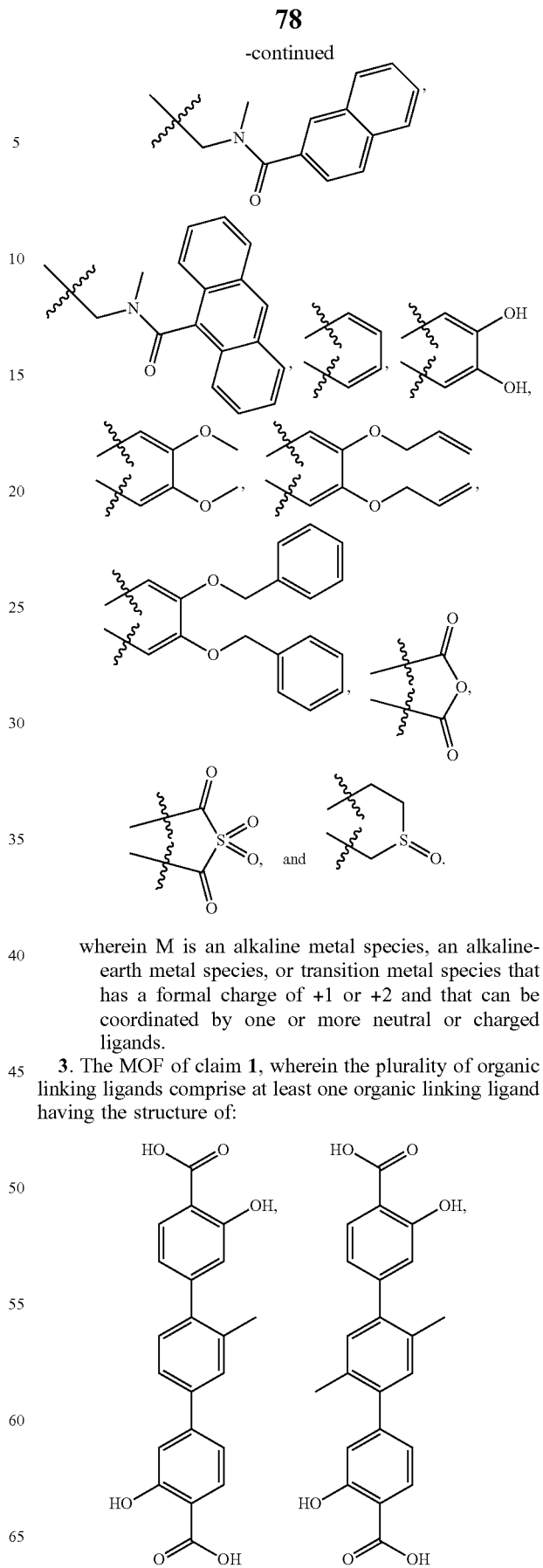
wherein M is an alkaline metal species, an alkaline-earth metal species, or transition metal species that has a formal charge of +1 or +2 and that can be coordinated by one or more neutral or charged ligands.
3. The MOF of claim 1, wherein the plurality of organic linking ligands comprise at least one organic linking ligand having the structure of:

-continued
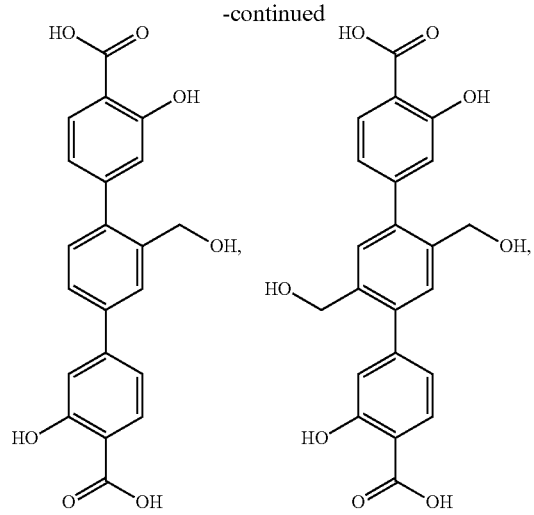
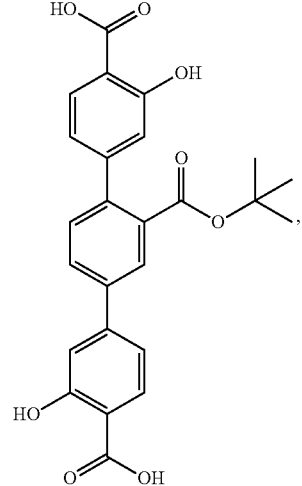
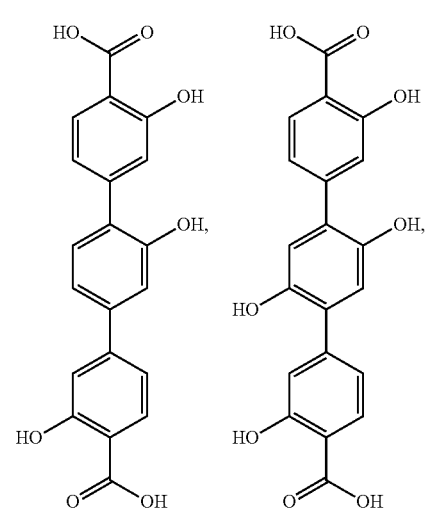
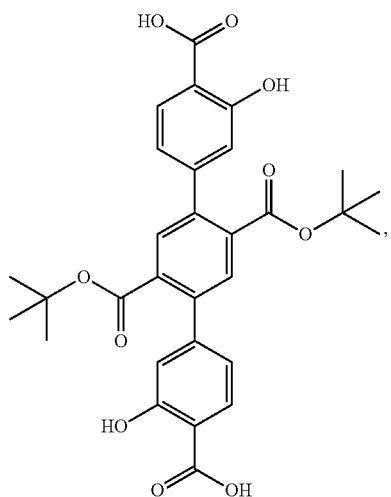
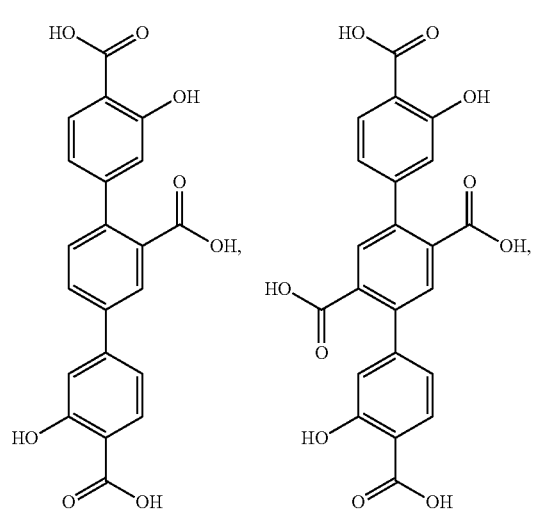
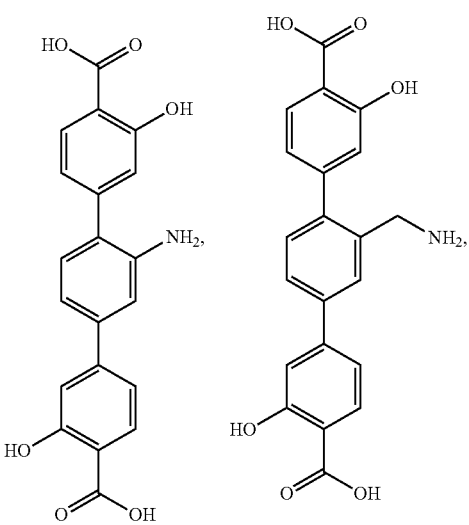

-continued

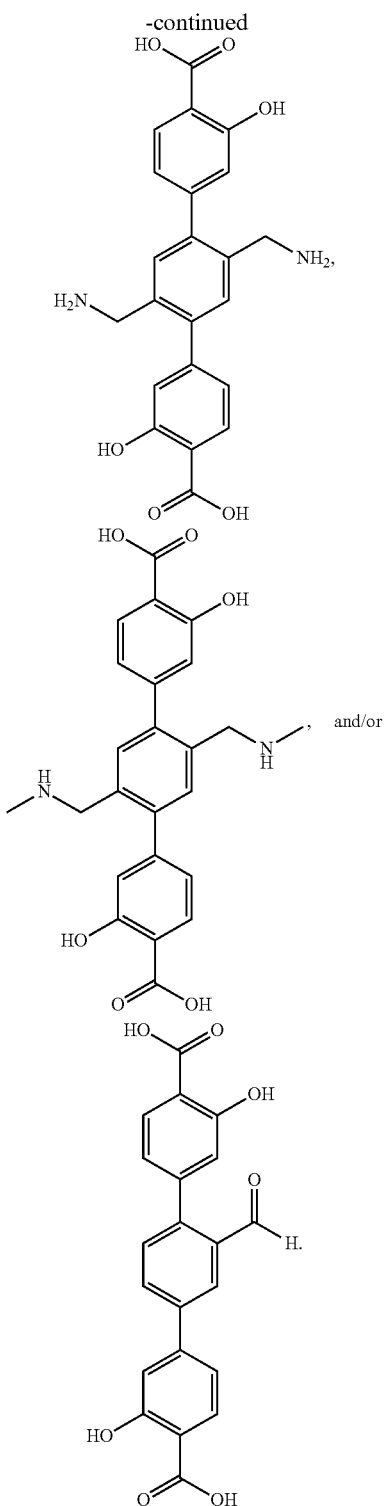

and/or

4. The MOF of claim 1, wherein any hydroxyl group is protected with a hydroxyl protecting group, any amine group is protected with an amine protecting group, and/or any carbonyl is protected with a carbonyl protecting group.

5. The MOF of claim 4, wherein the amine protecting group is a tert-butyl carbamate (Boc) group.

6. The MOF of claim 1, wherein the plurality of SBUs comprise at least three SBUs that differ by being comprised of different metals or metal ions.

7. The MOF of claim 1, wherein the plurality of SBUs comprise at least four SBUs that differ by being comprised of different metals or metal ions.

8. The MOF of claim 1, wherein the plurality of SBUs comprise one or more metals or metal ions selected from: $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, $La^+$, and combinations thereof, including any complexes which contain the metals or metal ions, as well as any corresponding metal salt counter-anions.

9. The MOF of claim 1, wherein the plurality of SBUs comprise one or more divalent metal ions selected from: $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $Db^{2+}$, $Tm^{2+}$, $Yb^{2+}$, and $La^{2+}$, including any complexes which contain the metal ions, as well as any corresponding metal salt counter-anions.

10. The MOF of claim 1, wherein the plurality of SBUs comprise one or more divalent metal ions selected from: $Mg^{2+}$, $Ca^{2+}$, $Sr^{2+}$, $Mn^{2+}$, $Fe^{2+}$, $Co^{2+}$, $Ni^{2+}$, and $Zn^{2+}$, including any complexes which contain the metal ions, as well as any corresponding metal salt counter-anions.

11. The MOF of claim 1, wherein the plurality of SBUs all have the same topology.

12. The MOF of claim 1, wherein the MOF comprises an M2M-MOF-74, and M4M-MOF-74, and M6M-MOF-74, and M8M-MOF-74 or an M10M-MOF-74.

13. A device comprising a MOF of claim 1.

14. A method of separating one or more gases from a gas mixture comprising contacting the gas mixture with a MOF of claim 1.

15. A method of catalyzing the formation of one or more products from one or more reactants by using a one-pot co-catalyst system that comprises contacting the one or more reactants with a MOF of claim 1.

* * * * *